United States Patent [19]

Weinreb et al.

[11] Patent Number: 5,310,674

[45] Date of Patent: * May 10, 1994

[54] APERTURED CELL CARRIER

[75] Inventors: Arye Weinreb, Jerusalem; Mordechai Deutsch, Moshav Olesh, both of Israel

[73] Assignee: Bar-Ilan University, Ramat-Gan, Israel

[*] Notice: The portion of the term of this patent subsequent to Mar. 8, 2005 has been disclaimed.

[21] Appl. No.: 737,920

[22] Filed: Jul. 29, 1991

Related U.S. Application Data

[63] Continuation of Ser. No. 165,070, Mar. 7, 1988, abandoned, which is a continuation-in-part of Ser. No. 550,233, Nov. 8, 1983, Pat. No. 4,729,949, which is a continuation-in-part of Ser. No. 489,605, May 2, 1983, abandoned.

[30] Foreign Application Priority Data

May 10, 1982 [CH] Switzerland ............... 2897/82

[51] Int. Cl.5 ................. C12M 1/32; C12M 1/12
[52] U.S. Cl. .................... 435/293; 435/311; 435/287; 422/101
[58] Field of Search .............. 435/2, 284, 292, 293, 435/296-298, 311, 284-286, 173, 291; 422/101; 210/323.1, 498; 209/38, 43, 397

[56] References Cited

U.S. PATENT DOCUMENTS

| | | |
|---|---|---|
| 1,915,568 | 6/1933 | Gortner et al. |
| 2,910,406 | 10/1959 | Novak. |
| 2,923,669 | 2/1960 | Poitras ............... 435/30 |
| 2,968,555 | 1/1961 | Bendler et al. ........ 430/323 |
| 3,139,392 | 6/1964 | Mears ................. 430/314 |
| 3,177,945 | 4/1965 | Fether ................ 210/498 |
| 3,190,778 | 6/1965 | Dahlberg .............. 430/323 |
| 3,190,827 | 6/1965 | Kok et al. ............ 204/186 |
| 3,207,684 | 9/1965 | Dotts ................. 210/222 |
| 3,303,254 | 2/1967 | Simons ................ 210/498 |
| 3,329,541 | 7/1967 | Mears ................. 156/644 |
| 3,361,612 | 1/1968 | Rowbottom ............. 156/495 |
| 3,368,963 | 2/1968 | Hall .................. 204/302 |
| 3,403,024 | 9/1968 | Luce .................. 430/5 |
| 3,445,152 | 5/1969 | Carter ................ 350/536 |
| 3,482,703 | 12/1969 | Roberts et al. ....... 210/498 |

(List continued on next page.)

FOREIGN PATENT DOCUMENTS

| | | |
|---|---|---|
| 562301 | 11/1983 | Australia. |
| 7447 | 2/1980 | European Pat. Off.. |
| 084631 | 8/1983 | European Pat. Off.. |
| 094193 | 11/1983 | European Pat. Off.. |
| 132064 | 1/1985 | European Pat. Off.. |
| 2928790 | 2/1981 | Fed. Rep. of Germany. |
| 0601101 | 12/1959 | Italy ................. 210/498 |
| 0023993 | 8/1979 | Japan. |
| 60-212330 | 10/1985 | Japan. |
| 7413572 | 4/1975 | Netherlands. |
| 833141 | 1/1984 | South Africa. |
| 522207 | 10/1984 | Spain. |
| 770229 | 3/1957 | United Kingdom. |
| 2028869 | 3/1978 | United Kingdom ....... 435/287 |

OTHER PUBLICATIONS

Sredni et al. "Antigen-Specific Clones of Proliferating T Lymphocytes" The Journal of Immunology, vol. 126, No. 1 (Jan. 1981) pp. 341-347.

(List continued on next page.)

Primary Examiner—Michael G. Wityshyn
Assistant Examiner—William H. Beisner
Attorney, Agent, or Firm—Maurice M. Klee

[57] ABSTRACT

An apertured cell carrier has a configuration defining first and second outer surfaces and comprising an ordered array of holes therethrough, the positions on the carrier of the holes being identifiable and the holes being sized to have the ability to contain individual living cells having a generally spherical shape therewithin, one cell only per hole, in that the holes have (i) a first cross section at the first outer surface of the carrier of such dimensions that living cells can pass through the first cross section without suffering substantial damage, (ii) a second cross section at a level intermediate between said first and second outer surfaces and of such dimensions that said living cells cannot pass through the second cross section, and (iii) a height between the first outer surface and the level of the second cross section such that either such an entire living cell or substantially such an entire living cell is containable within the hole.

13 Claims, 46 Drawing Sheets

U.S. PATENT DOCUMENTS

| | | | |
|---|---|---|---|
| 3,594,261 | 7/1971 | Broerman | 428/85 |
| 3,719,583 | 3/1973 | Ustick | 210/222 |
| 3,726,597 | 4/1973 | Dvorak et al. | 356/244 |
| 3,768,914 | 10/1973 | Kinney et al. | 356/244 |
| 3,776,699 | 12/1973 | Gross | 422/50 |
| 3,806,386 | 4/1974 | Burke et al. | 156/73.1 |
| 3,851,972 | 12/1974 | Smith et al. | 356/72 |
| 3,874,851 | 4/1975 | Wilkins et al. | 435/30 |
| 3,888,770 | 6/1975 | Avital et al. | 210/238 |
| 3,899,610 | 8/1978 | Henry | 427/2 |
| 3,924,947 | 12/1975 | Hogg | 356/39 |
| 3,929,583 | 12/1975 | Sharpe et al. | 195/127 |
| 3,947,121 | 3/1976 | Cotter et al. | 356/38 |
| 3,947,126 | 3/1976 | Mendez | 356/150 |
| 3,974,016 | 8/1976 | Bondybey et al. | 156/272.8 |
| 3,997,385 | 12/1976 | Osborne | 156/272.8 |
| 4,009,435 | 2/1977 | Hogg | 356/38 |
| 4,025,306 | 5/1977 | Studer | 435/311 |
| 4,029,535 | 6/1977 | Cannon et al. | 156/272.8 |
| 4,052,163 | 10/1977 | Patzner | 422/101 |
| 4,055,799 | 10/1977 | Coster et al. | 435/173 |
| 4,058,432 | 11/1977 | Schuster-Woldan et al. | 156/659 |
| 4,066,359 | 1/1978 | Bucalo | 356/36 |
| 4,069,080 | 1/1978 | Osborne | 156/272.8 |
| 4,089,765 | 5/1978 | Dudley | 204/108 R |
| 4,131,800 | 12/1978 | Bruck et al. | 250/461.2 |
| 4,162,850 | 7/1979 | Warren | 356/38 |
| 4,224,096 | 9/1980 | Osborne | 156/380.9 |
| 4,231,660 | 11/1980 | Remy et al. | 356/244 |
| 4,288,330 | 9/1981 | Strub | 210/777 |
| 4,317,726 | 3/1982 | Shepel | 422/101 |
| 4,326,934 | 4/1982 | Pohl | 204/180 R |
| 4,362,389 | 12/1982 | Koizumi et al. | 356/401 |
| 4,374,644 | 2/1983 | Armstrong | 436/63 |
| 4,388,351 | 6/1983 | Sawyer | 427/304 |
| 4,395,397 | 7/1983 | Shapiro | 424/101 |
| 4,415,405 | 11/1983 | Ruddle et al. | 156/645 |
| 4,418,906 | 12/1983 | Scott | 271/99 |
| 4,423,959 | 1/1984 | Nakazawa et al. | 356/400 |
| 4,441,809 | 4/1984 | Dudley et al. | 356/1 |
| 4,441,972 | 4/1984 | Pohl | 204/180 R |
| 4,461,945 | 7/1984 | O'Cheskey | 219/121 |
| 4,461,947 | 7/1984 | Ward | 219/121.84 |
| 4,497,884 | 2/1985 | Schmidt et al. | 430/5 |
| 4,498,778 | 2/1985 | White | 356/376 |
| 4,531,060 | 7/1985 | Suwa et al. | 250/548 |
| 4,534,819 | 8/1985 | Payet | 156/515 |
| 4,662,754 | 5/1987 | Mayer | 356/401 |
| 4,729,949 | 3/1988 | Weinreb et al. | 435/311 |
| 4,894,343 | 1/1990 | Tanaka et al. | 435/311 |

OTHER PUBLICATIONS

Deutsch, M. and Weinreb, A., *E.J.C.*, (Feb., 1983) 19:187–193.

Fejes G. and Tarjan G., "Machinery and processes in the Chemical Industry" ed. Tankonyvkiado, Budapest, 1979, pp. 276–277.

*Laboratory Equipment Digest*, vol. 18, No. 10, Oct. 1980, pp. 91–93.

Pritchard, J., et al., *Br. J. Cancer*, (1978) 38:339–343.

Balding, P., et al., *Br. J. Cancer*, (1980) 41:73–85.

Cerek, L., et al., *Biophysik 10*, (1973) 187–194.

Cerek, L., et al., *Br. J. Cancer*, (1974) 29:345–352.

Cerek, L., et al., *Br. J. Cancer*, (1975) 31:252–253.

Cerek, L., et al., *Immunology*, (1975) 29:885–891.

Cerek, L., et al., *Br. J. Cancer*, (1976) 33:539–543.

Cerek, L., et al., *Rad. and Environm. Biophys.*, (1976) 13:9–12.

Cerek, L., et al. *Eur. J. Cancer*, (1977) 13:903–915.

Cerek, L., et al., *Eur. J. Cancer*, (1981) 17:167–171.

Hocking, G., et al., *J.N.C.I.*, (1982) 68:579–583.

Mitchell, H. et al., *Br. J. Cancer*, (1980) 41:772–777.

Orjaseter, H., et al., *Br. J. Cancer*, (1979) 40:628–633.

Pritchard, J., et al., *Eur. J. Cancer*, (1982) 18:651–659.

Sakamoto, S., et al., *Eur. J. Cancer Clin. Oncol.*, (1981) 17:1105–1115.

Schnuda, N., *Cancer*, (1980) 46:1164–1173.

Tsuda, H., et al., *Br. J. Cancer*, (1981) 43:793–803.

Schildkraut et al., *Journal of Histochemistry and Cytochemistry*, vol. 27, No. 1, pp. 289–292, 1979.

Shapiro, H. M., Practical Flow Cytometry, Alan R. Liss, Inc., NY pp. xv–xvi by L. Kamentsky, xviii, 5, 17, and 78–79, 1984.

Kanz, et al., *Cytometry*, vol. 7, pp. 491–494, 1986.

Tamasi A. and Schvartz S., Szures (Filtration) ed. by Muszaki Konyvkiado, Budapest, 1968, pp. 34–35.

Shortman, K. "Methods of Cell Separation", vol. 1 1977 pp. 229–249 chapter 6, Plenum Press, New York.

Cercek, L. Biophysical Journal, vol. 23, No. 1, 1978, pp. 395–405, Biophysical Society.

Rutishauser et al. "Methods of cell separation", vol. 1, 1977, pp. 193–223, chapter 5, Plenum Press, New York.

Matveev, "Handbook for Microbiological Diagnosis of Infectious Diseases" Meditsina publishers, 1973, pp. 117–118.

Maes, J. J., "Microelectronics & Reliability" vol. 17 No. 2, 1978, pp. 325–332, Pergamon Press, Oxford GB.

DuPont's brochure, Riston Image Transfer Systems, DuPont Photoproducts Dept., Wilmington, Del. Nov. 1981.

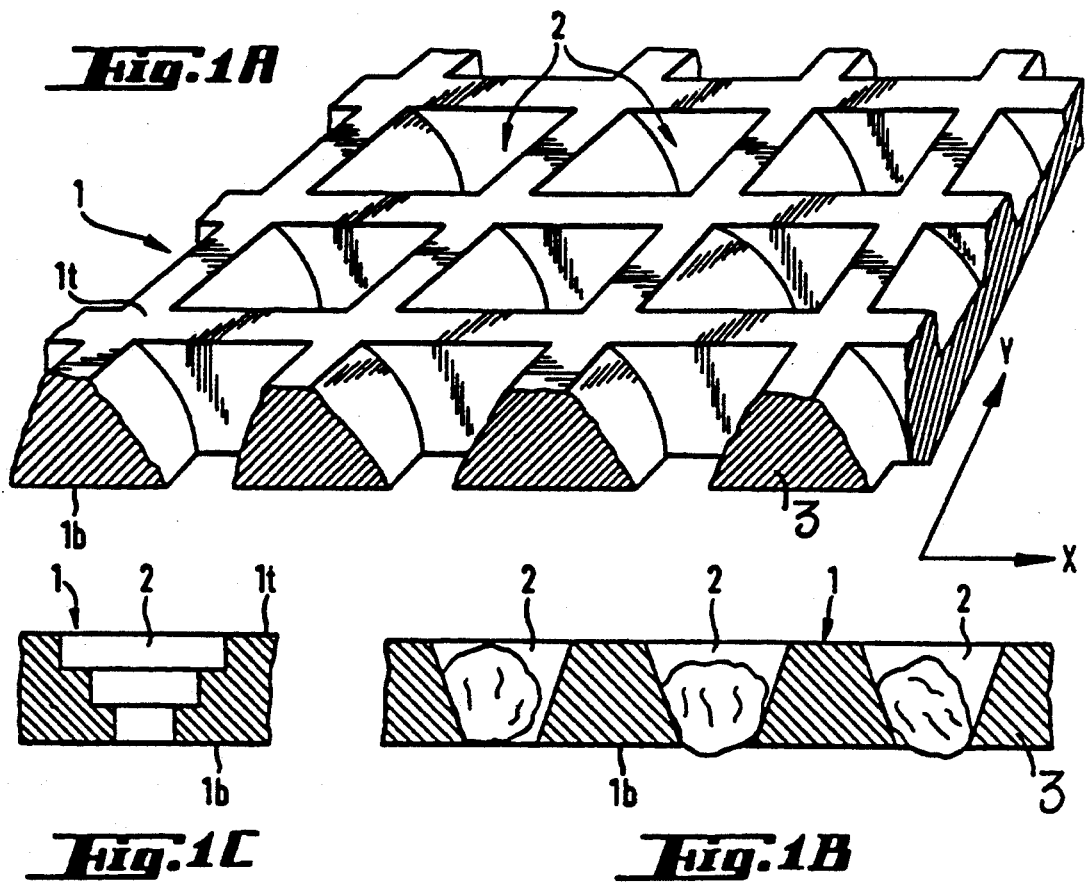
Fig. 1A
Fig. 1C
Fig. 1B
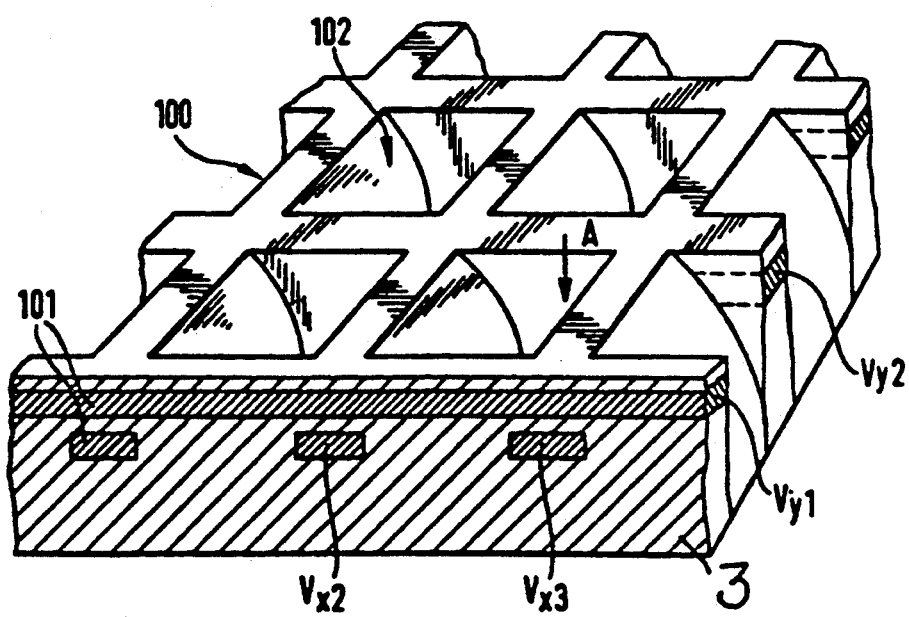
Fig. 17

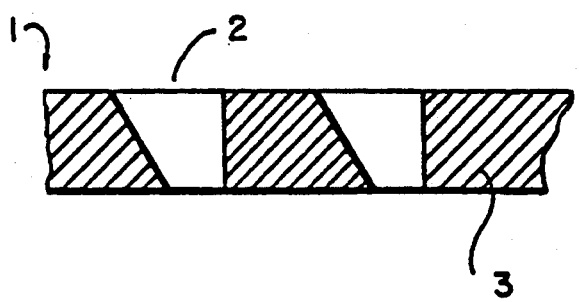
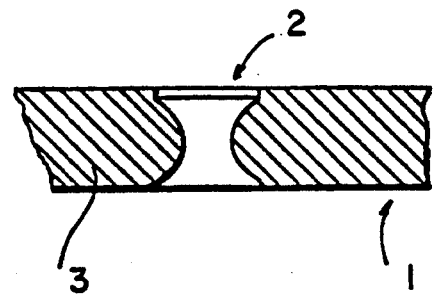
Fig. 1D  Fig. 1E
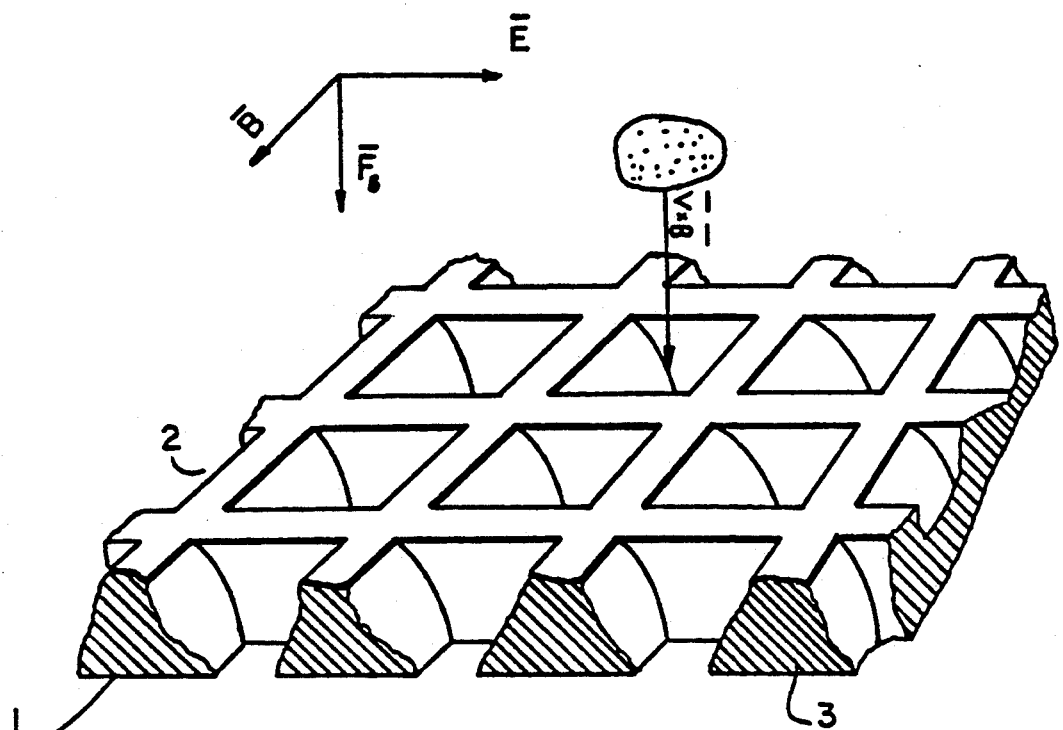
Fig. 48
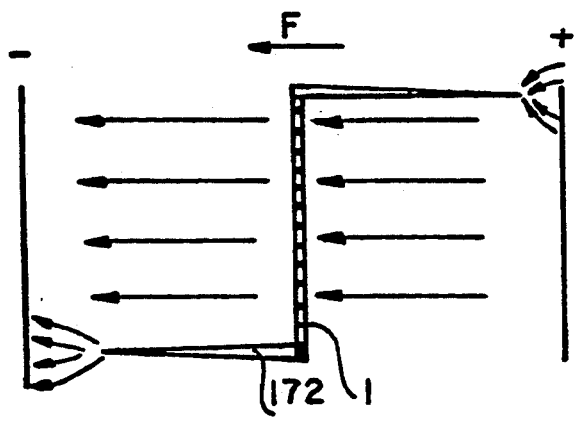
Fig. 47

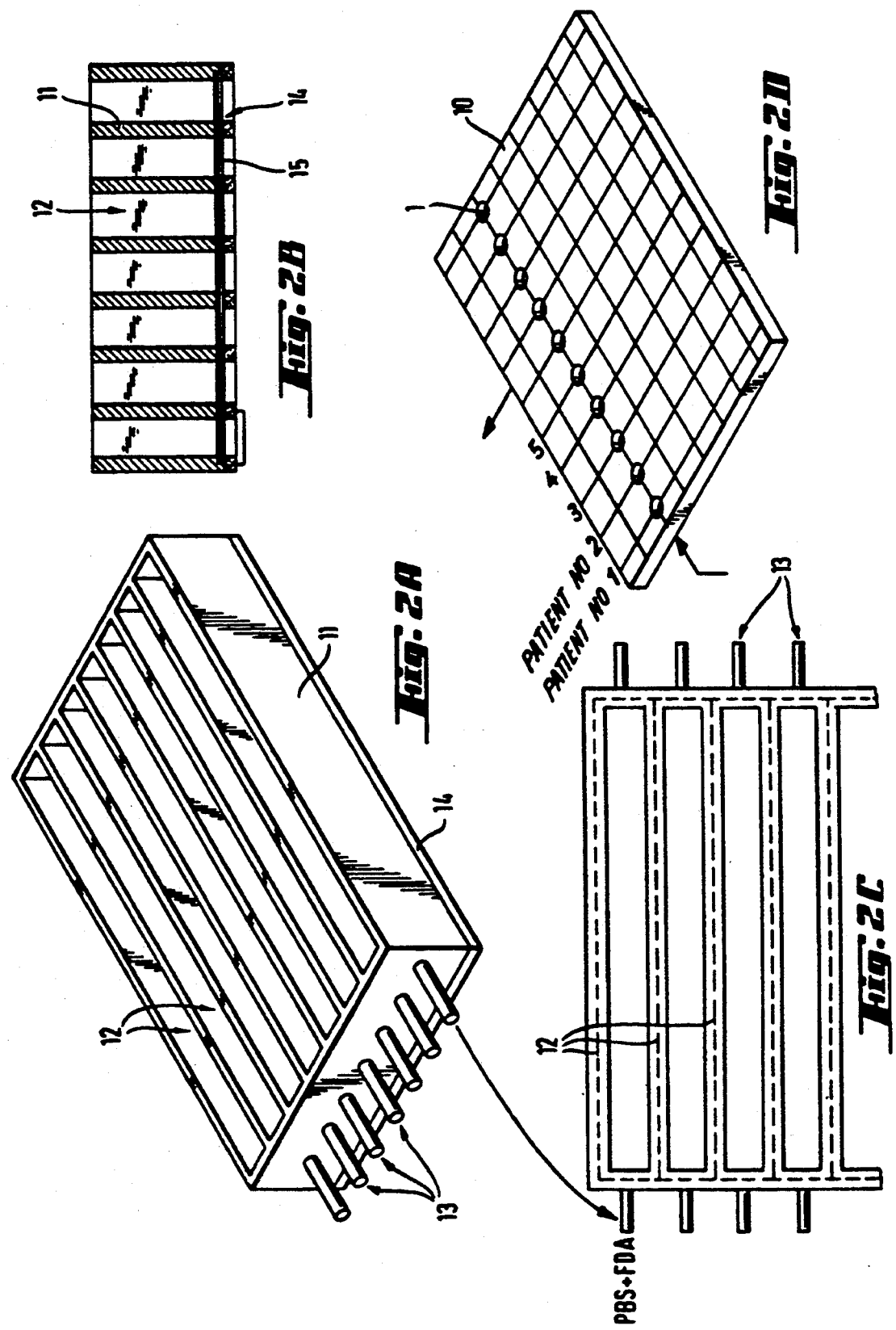

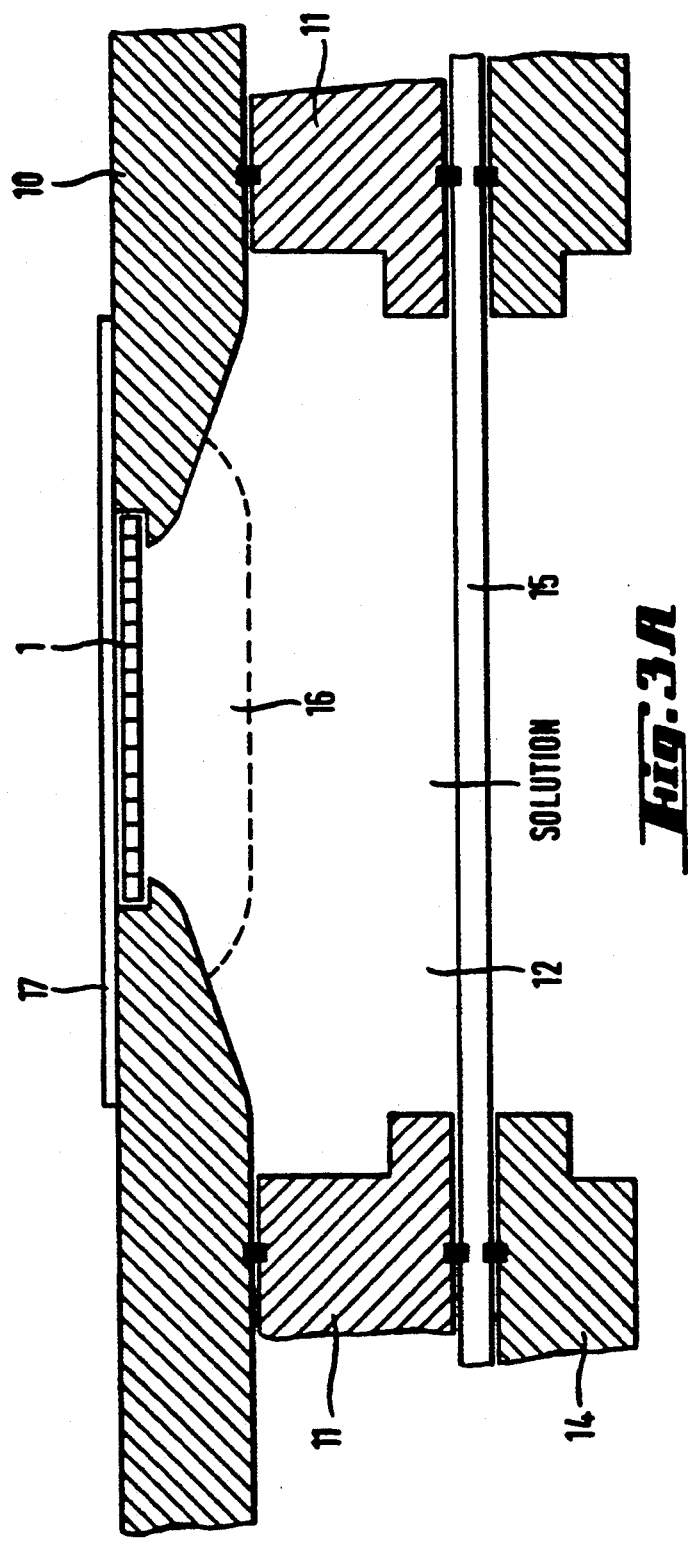
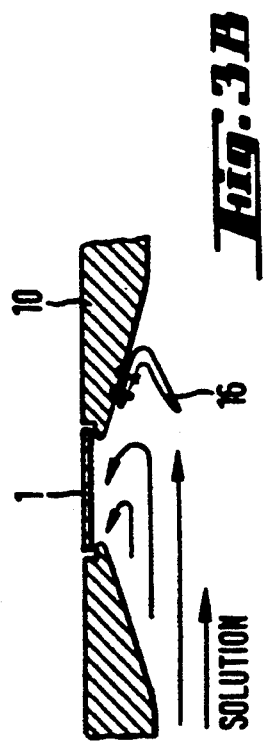
Fig. 3A
Fig. 3B

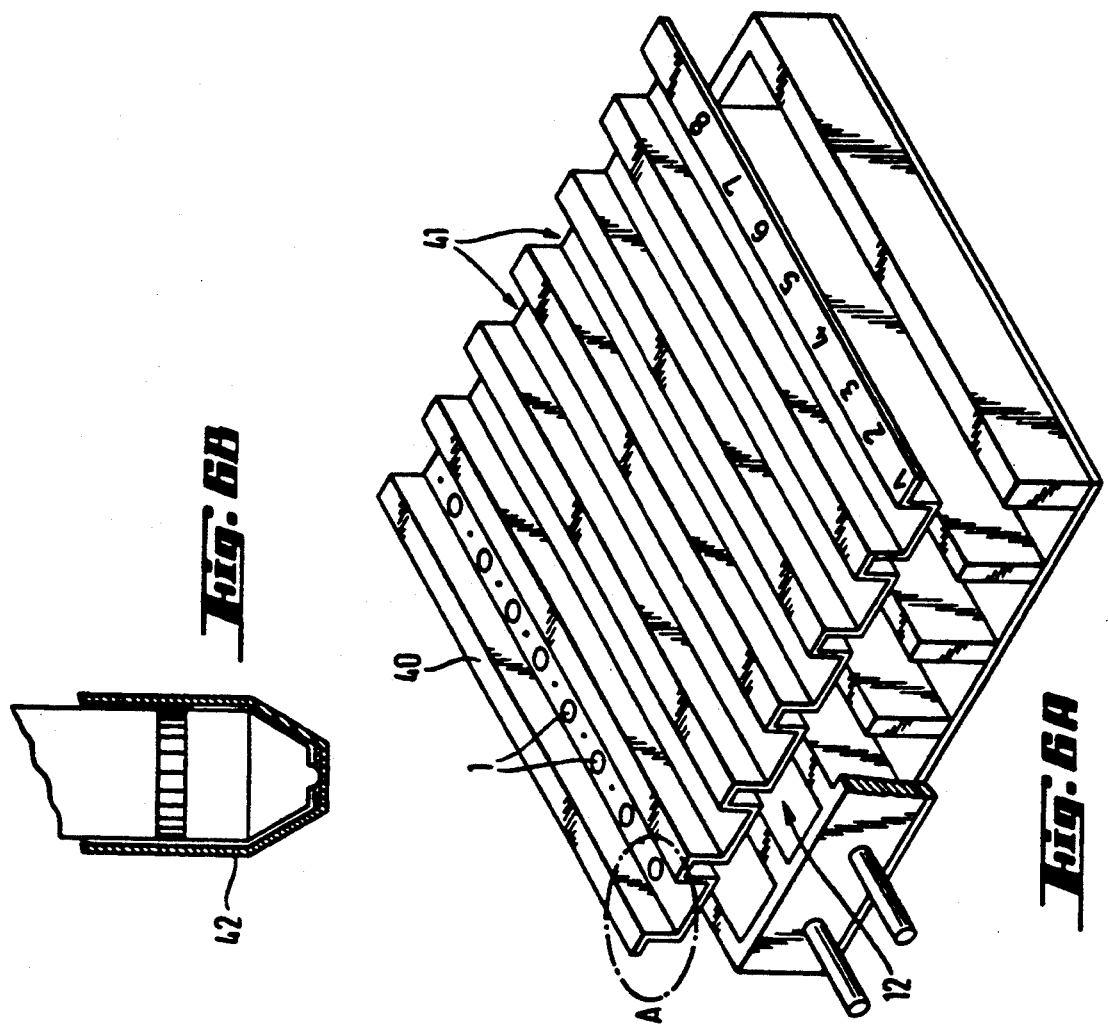
Fig. 6B
Fig. 6A
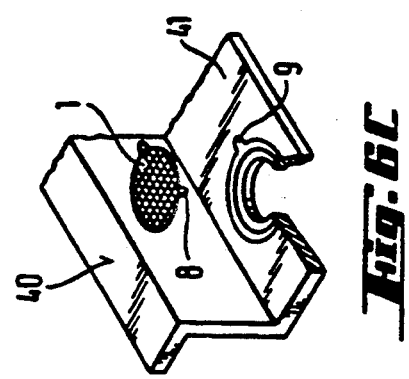
Fig. 6C

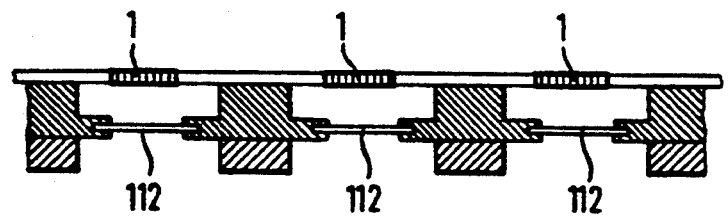
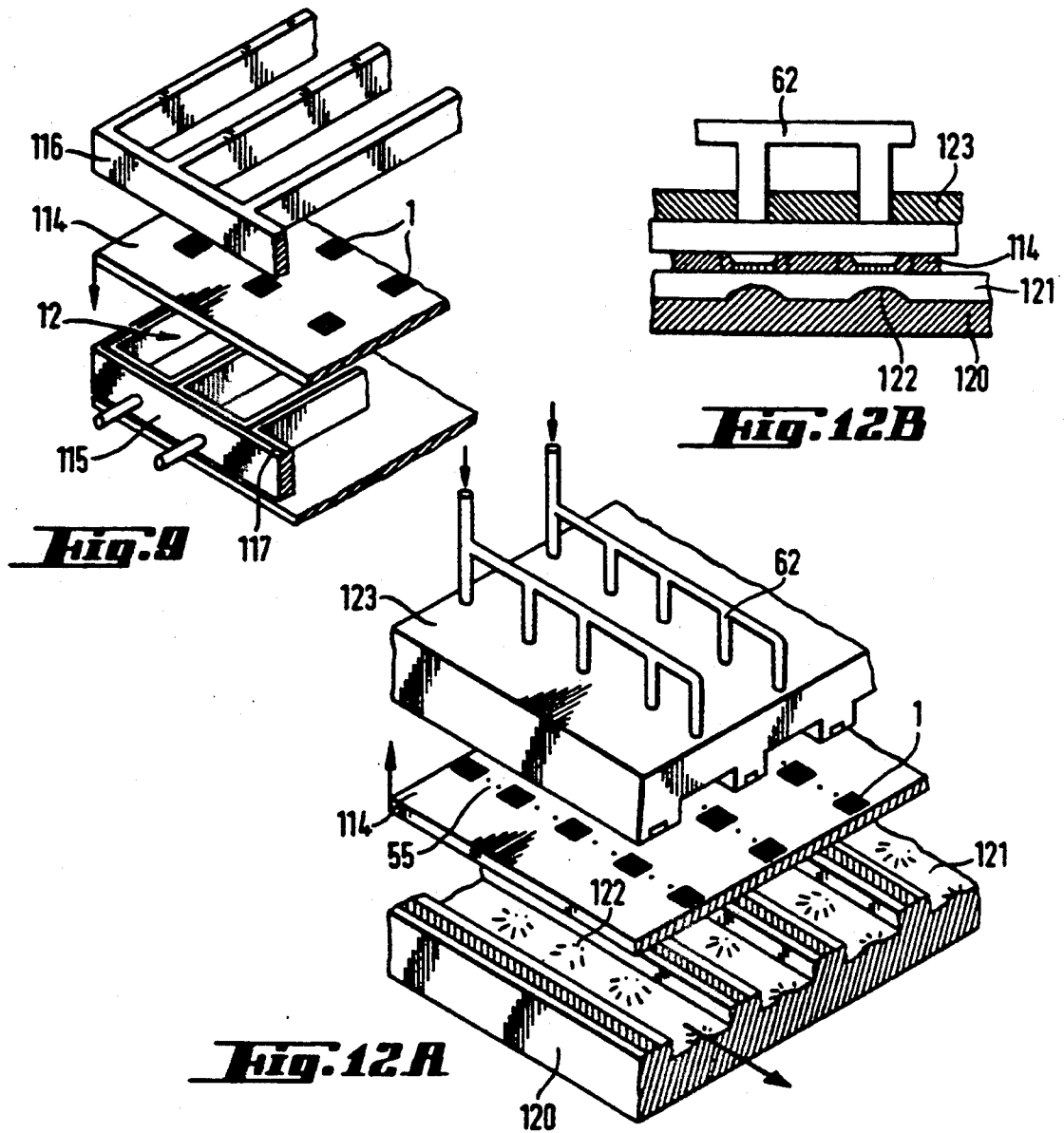

Fig. 4.3

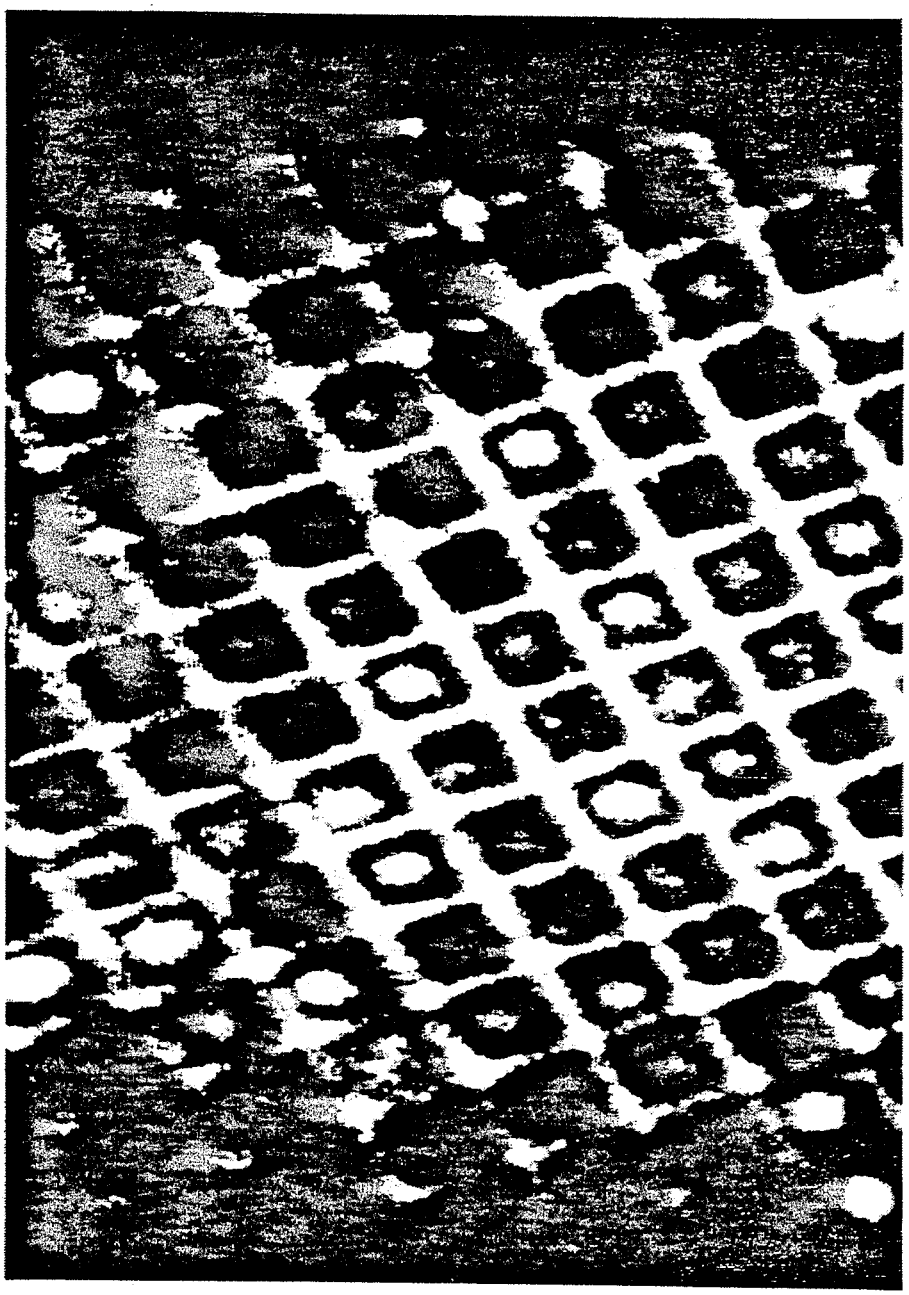
Fig. 4.5

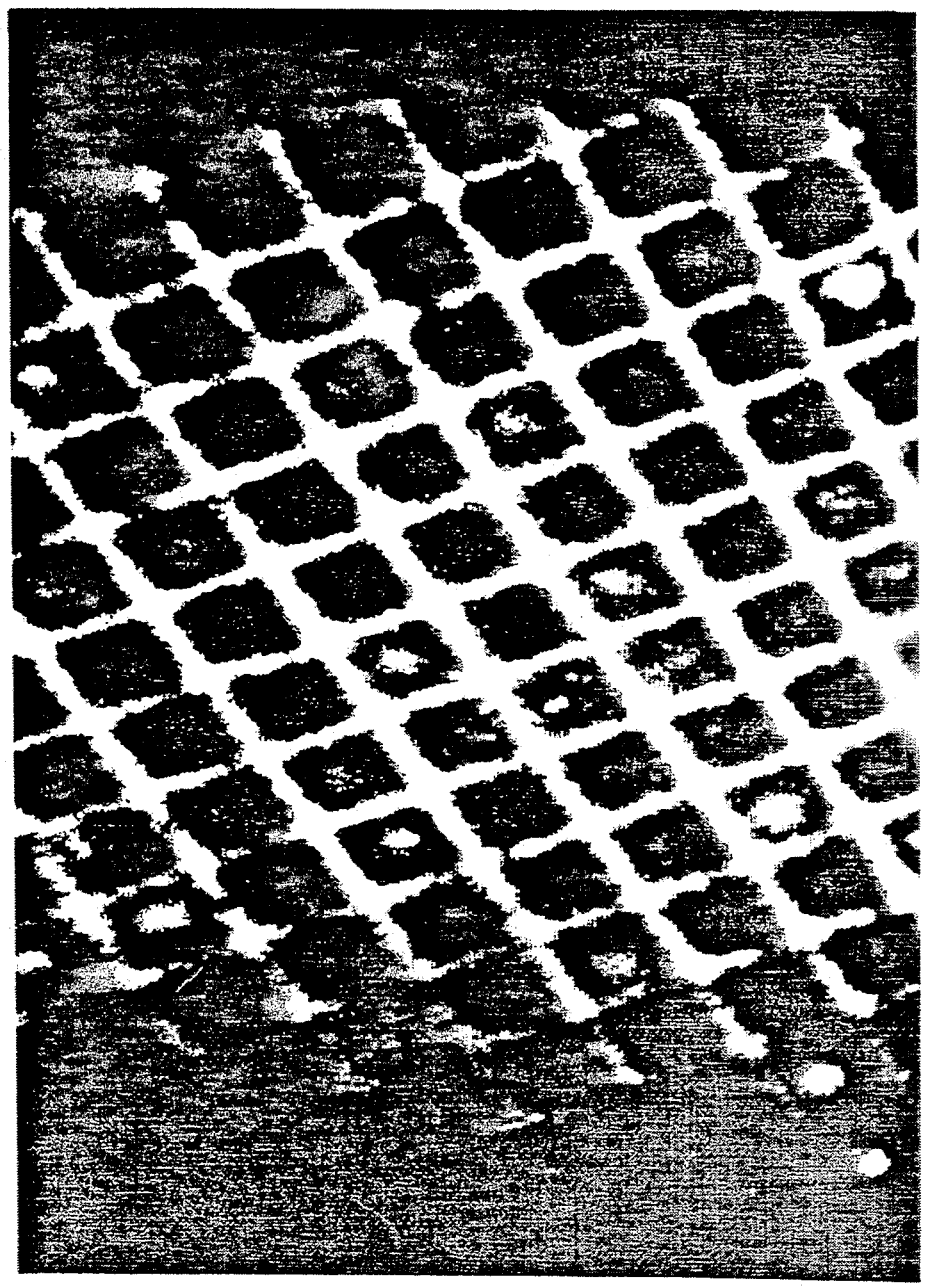
Fig. 4.6

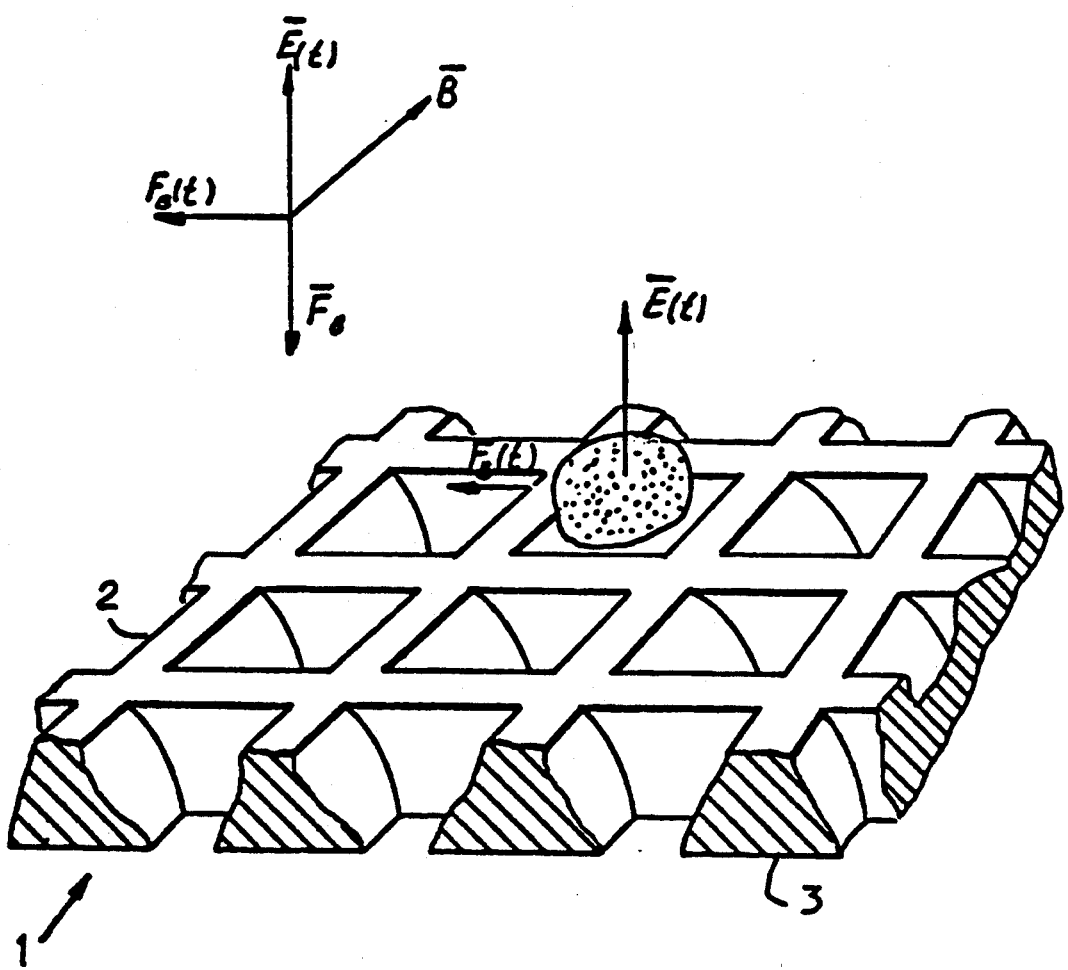

APERTURED CELL CARRIER

This is a continuation of copending application Ser. No. 07/165,070, filed on Mar. 7, 1988, now abandoned, which is a continuation-in-part of application Ser. No. 06/550,233, filed Nov. 8, 1983, now U.S. Pat. No. 4,729,949, which is a continuation-in-part of application Ser. No. 06/489,605, filed May 2, 1983, now abandoned.

FIELD OF THE INVENTION

The present invention relates to an apertured cell carrier which has the capability of containing individual living cells at identifiable locations. This cell carrier may accordingly be utilized for trapping individual cells at known locations, thereby enabling at least one sub-population of cells to be selected from a more general cell population, using defined parameters common to the sub-population, and also enabling the simultaneous study of large groups of living cells, e.g. 10,000 or more living cells, on a cell-by-cell basis. The invention also relates to such a carrier which contains living cells contained within individual holes therein, as well as to a process for increasing the number of such cells.

BACKGROUND OF THE INVENTION

Equipment and methods for selecting, observing and separating sub-populations of biological cells, e.g., those contained in the blood, are known. Several methods which are considered to be important and indicative of the state of the art will now be described and commented on.

Separation based on cell adhesion. This method is not very efficient and is not suited for separation of different cells which have the same membrane characteristics, e.g., between cells that stick to glass.

Immunofluorescence separation. This method is based on known binding characteristics of sub-populations of cells to certain antigens and/or antibodies. The selective binding of these particular types of cells allows sub-populations of cells to be identified. However, this method is quite limited because it cannot distinguish subgroups within a group of cells based on specific biological activities and functions.

Electrophoresis. This method achieves cell-separation based on the relative rates of movement of different types of cells in an electric field. Thus, the method cannot be used to separate different groups of cells which respond to an electric field in the same manner.

Radio assay including radio immunoassay, radio incorporation assay, radio enzymological assay. In this method one cannot separate groups of cells from one another, nor distinguish a sub-group within a group based on specific biological activities and functions.

Morphology. Distinction between cells is based on their physical appearance. This method is quick but the coarsest of all.

Cell separation according to specific density (gradient technique). In this method cells float upon an isotonic solution of known density, osmolarity and viscosity. This configuration is subjected to acceleration forces by centrifugation at a given temperature and acceleration. The cells, having a specific weight greater than that of the solution sink. Those having the specific density of the solution are suspended in it, and those with a specific density less than that of the solution float above it. The main problem with this method is the cells' compartmentalization within the density gradient, which is influenced by ambient conditions such as temperature, osmolality, acceleration, e.g., the distance of the interface between the blood and the gradient from the spinning axis.

In addition to the above-stated shortcomings of the various prior art methods, a disadvantage common to all of them is due to the fact that the separated cells nearly always include cells belonging to other than the group or subgroup of interest. Therefore, the diagnosis which is based on the cell of interest is necessarily coarse, even if all the procedures have been carried out with the utmost precision.

For example, L. Cercek et al describe a SCM-test (Structuredness of Cytoplastic Matrix) in Biophys. J., July 1978, Vol. 23, No. 1. p. 395 ff. In said article the authors admit that by the above described gradient method, separated cells contain about 50% of undesired cells, in spite of the great care with which the test was conducted.

The inability to totally separate a particular group of cells from all others greatly affects diagnosis accuracy. Furthermore, and most significantly, in the above described methods, cell separation and the subsequent tests conducted thereon are on a macro or batch basis, rather than on a micro basis, i.e. one in which the selected cells are separated from one another and each cell can be separately tested and examined. Any system and method for separating selected cells of interest from other cells and further separating selected cells from one another, so that each can be separately tested and/or examined, would be of great significance in diagnosing various biological conditions and for other purposes. Testing and examining individual selected cells would eliminate errors, presently existing in many diagnoses, based on inexact statistical criteria.

A major object of the invention of U.S. Pat. No. 4,729,949 is to provide a method and equipment for selecting a group of cells from other cells and further separate the selected cells from one another. Each of the selected cells, separated from one another, is at a precisely known location. All of the selected cells are subjectable to common tests, yet the effect on each individual cell is determinable, thereby enabling more accurate diagnosis. The tests and the effects on each cell are performed automatically in order to reduce the testing time and to permit the task to be performed by relatively unskilled personnel.

Thus, U.S. Pat. No. 4,729,949 discloses and claims a method for placing individual cells at identifiable addresses within the holes of a carrier, and for performing on a cell-by-cell basis one or more of the operations of (i) observing or measuring a property of a living cell, (ii) moving a living cell, or (iii) killing a living cell, comprising the steps of:

(a) providing a carrier defining first and second outer surfaces and comprising an ordered array of holes therethrough, the positions on the carrier of the holes being identifiable and the holes being sized to contain individual living cells therewithin that the holes have (i) a first cross section at the first outer surface of the carrier of such dimensions that the living cell can pass through the first cross section without suffering substantial damage, (ii) a second cross section at a level spaced from the first outer surface of such dimensions that the living cell cannot pass through the second cross section, and (iii) a height between the first outer surface and the level of the second cross section such that either the entire living cell or substantially the entire living cell is contained within the hole so that the living cell is not washed out of the hole by the passage of a fluid across the first outer surface of the carrier;

(b) applying a fluid containing living cells to the first outer surface of the carrier;

(c) applying a force to the living cells to move the living cells into the holes; and where desired (d) performing on an individual, first living cell located at a first hole having a first position on the carrier one or more of the operations of (i) observing or measuring a property of the first living cell, (ii) moving the first living cell, or (iii) killing the first living cell; and (e) performing on an individual, second living cell located at a second hole having a second position on the carrier one or more of the operations of (i) observing or measuring a property of the second living cell, (ii) moving the second living cell, or (iii) killing the second living cell.

U.S. Pat. No. 4,729,949 also discloses and claims an apparatus for selecting particular living cells from among other living cells and for performing on a cell-by-cell basis one or more of the operations of (i) observing or measuring a property of a living cell, (ii) moving a living cell, or (iii) killing a living cell, comprising: (a) a carrier as defined in paragraph (a), above; (b) means for applying a fluid containing living cells to the first outer surface of the carrier; (c) means for applying a force to the living cells to move the living cells into the holes; and (d) means for performing on an individual, living cell located in one of the holes in the carrier one or more of the operations of (i) observing or measuring a property of the living cell, (ii) moving the living cell, or (iii) killing the living cell; and where (d) constitutes observing or measuring means, the apparatus optionally includes (e) means associated with such means, for recording the addresses on the carrier of particular living cells based on the results of observing or measuring the one or more properties.

SUMMARY OF THE INVENTION

It is an important object of the present invention to provide a novel apertured cell carrier which enables the method of U.S. Pat. No. 4,729,949 to be carried out.

It is also an important object of the present invention to provide a novel apertured cell carrier which may form part of the apparatus claimed in U.S. Pat. No. 4,729,949.

Another object of the invention is to provide a novel apertured cell carrier including cells in the holes of the carrier.

Yet another object of the invention is to provide a process for multiplying cells located within the holes of such novel apertured carrier.

Still a further object of the invention is to provide a novel apertured carrier wherein the holes, and thus any cells located within particular holes, are at identifiable addresses on the carrier. Other objects of the invention will be apparent from the description which follows.

According to an embodiment of the present invention there is provided an apertured cell carrier defining first and second outer surfaces and comprising an ordered array of holes therethrough, the positions on the carrier of the holes being identifiable and the holes being sized to contain individual living cells therewithin in that the holes have (i) a first cross section at the first outer surface of the carrier of such dimensions that living cells can pass through the first cross section without suffering substantial damage, (ii) a second cross section at a level spaced from the first outer surface of such dimensions that such living cells cannot pass through the second cross section, and (iii) a height between the first outer surface and the level of the second cross section such that either such an entire living cell or substantially such an entire living cell is containable within the hole. According to a particular embodiment, the level of the second cross section may be intermediate between the first and second outer surfaces of the carrier. According to another particular embodiment, the said ordered array comprises a plurality of uniformly shaped holes sized to accommodate individual living cells of the same size therewithin.

In the apertured cell carrier of the invention, the location of each hole in the array is known and identifiable. The holes extend between the two outer surfaces of the carrier, they have preselected configurations so that when a batch of cells is passed over the first outer surface of the carrier, only preselected cells, based on their particular size, enter and become supported in the holes. Cells of sizes smaller than those of the selected cells pass through the holes, while much larger cells cannot enter the holes. Once the carrier is rinsed, only selected cells are located in its holes, one cell per hole at a fixed address.

The cells in the carrier holes may be multiplied, as will be described below. They may also be subjected to biological tests and particular properties thereof may be measured on a cell-by-cell basis, to determine which of the cells belong to a particular subgroup, based on their particular properties and their measured parameters. Once a subgroup of cells has been identified, since each cell thereof is at a known address, the addresses of all the subgroup cells are known. Thus, one can subject all the cells to one or more tests, but examine the properties of only each cell in the subgroup by directing the particular measuring and/or diagnosing instruments to the cell's unique address.

The cells which may be separated and multiplied by use of the apertured cell carrier of the invention represent a unique composition of matter, because they are of a uniform type and size, either 100% pure or substantially 100% pure, which degree of purity has not to the inventors' knowledge been realized before.

Thus there are made available for purposes of (e.g.) research, manufacture, medicine, diagnosis or further processing, cells in viable quantity and which are either 100% pure or substantially 100% pure; cells in such viable quantities and degree of purity which would not be available at all were it not for the apertured cell carriers provided by the present invention.

BRIEF DESCRIPTION OF THE DRAWINGS

Further objects and features of the present invention will become more apparent from the following description of several embodiments of the invention, and of the utility thereof, with especial reference to the accompanying drawings [in which the term "cell carrier(s)" means such carrier(s) according to the invention unless the context requires otherwise], wherein:

FIGS. 1A–1E are schematic illustrations, partly in sectional view, of embodiments of cell carriers;

FIGS. 2A–2D illustrate one embodiment of a multiple cell carrier holder for carrying out measuring cycles at a plurality of cell carriers;

FIGS. 3A and 3B are enlarged sectional views showing placement of the carriers in the apparatus of FIG. 2;

FIGS. 6A–6C show modified holders of the embodiment of FIG. 3;

FIG. 8 shows a modified version of the embodiment of FIG. 7;

FIG. 9 shows another embodiment of a holder and a flow chamber for an advanced analyzing system;

FIGS. 12A and 12B show a separation unit adapted to receive the holder of FIG. 9 for providing the cell carriers with cells;

FIG. 17 shows a cell carrier adapted for selectively attracting or releasing desired cells;

FIGS. 42–46 are a sequence of still videotape photographs showing that substances can be applied (42–44) and removed (45–46) from cells held in the apertures of a carrier;

FIG. 47 shows the use of an electric field to drive cells into the apertures of a carrier;

FIG. 48 shows the use of crossed electric and magnetic fields to drive cells into the apertures of a carrier;

FIG. 51 shows the use of a time varying E field crossed with a constant B field to select a sub-population of cells captured in a carrier based on their charge to mass ratio.

DETAILED DESCRIPTION OF THE INVENTION

Figure 4:
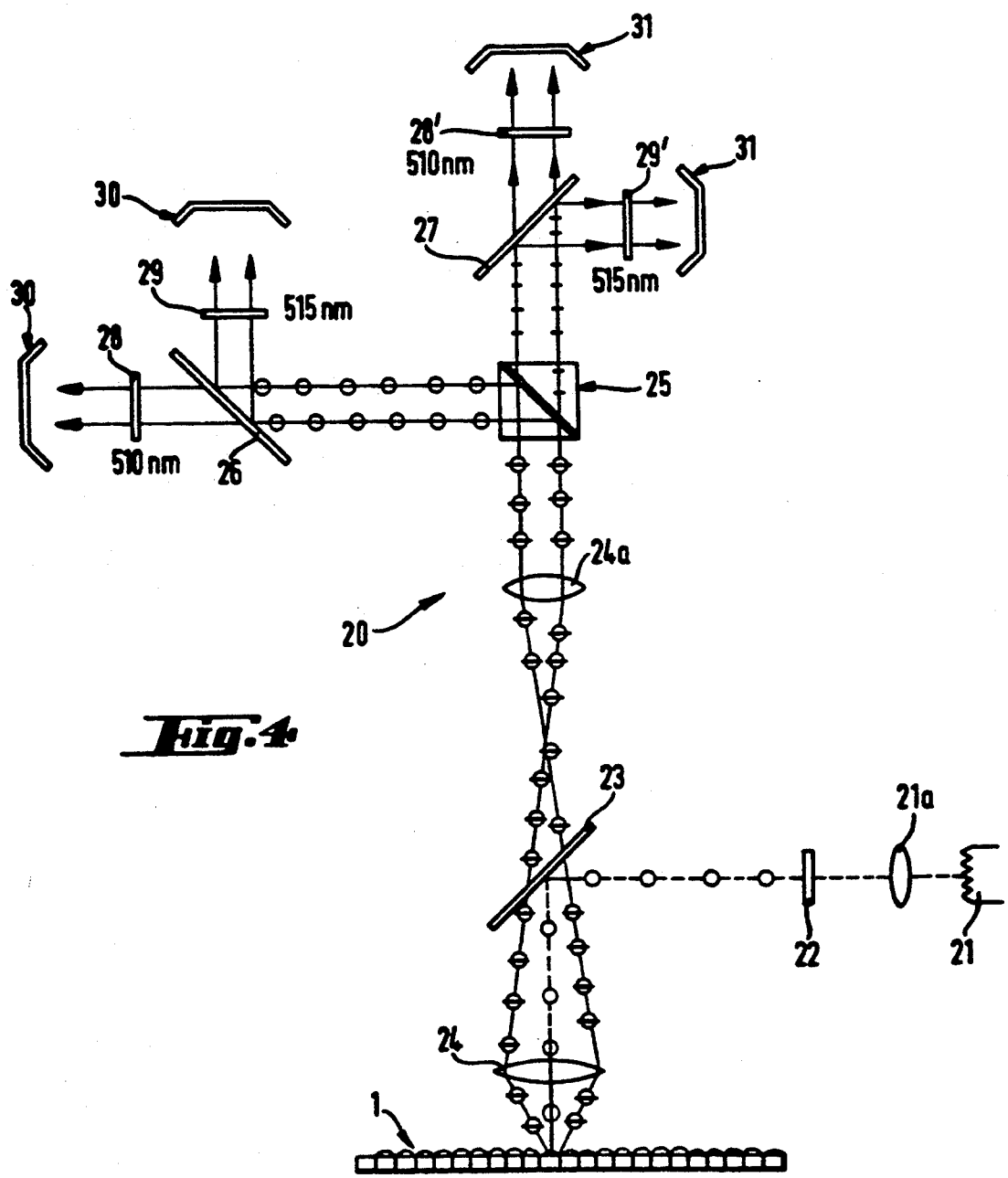
FIG. 4 illustrates schematically an optical analyzer for scanning individually the cells of the population contained in a cell carrier.

There will first be described, in a non-limiting way, employment of the carriers of the invention for selecting and analyzing a particular population of cells of a given type contained in a biological fluid from other populations of cells. In addition, a further selection of a special sub-population may be made from the particular population selected initially. More specifically, there will be described selecting and analyzing a particular sub-population of lymphocytes, which are present in human blood, by first separating the lymphocytes from other types of cells, and then testing the lymphocytes to identify a sub-population of a group within the lymphocyte group. It will be appreciated that the apertured cell carriers of the present invention thus uniquely make available populations and sub-populations of cells (e.g. lymphocytes) according to their dimensions and other parameters, in viable quantities and having an extraordinary degree of purity.

L. Cercek and B. Cercek in articles published in European Journal of Cancer, 13: 903–915 (1977) and 17: 167–171 (1981), and in Biophys. J. 23: 395–405 (1978), discuss the excitation and emission-polarization spectra of fluorescein in living cells in relation to the application of the phenomenon of changes in the Structuredness of the Cytoplastic Matrix (SCM) in the diagnosis of malignant disorders. Briefly, the Cerceks perform the so-called SCM test after first trying to separate a particular sub-group of lymphocytes from other lymphocytes, as well as other types of cells by the density gradient technique.

This technique as previously pointed out is very unsatisfactory. First, it is very time consuming, as is appreciated by those familiar with the art, and as is clearly apparent from the articles by the Cerceks. Secondly, as the Cerceks acknowledge, the finally separated cells do not belong to only the subgroup of interest, but include a large number, on the order of 50%, of other lymphocytes. Thus, the analysis of their response to stimulation of the separated cells is very limited. Thirdly, and most significantly, all of the stimulations and response measurements, performed by the Cerceks on the separated cells, are done on all the cells in a batch, rather than on a cell-by-cell basis. However, it is clear that a cell-by-cell analysis provides far more information for the understanding of biological implications of the phenomena under study.

The present invention makes it possible to realize such analyses very quickly, and accurately. In this particular case, both speed and accuracy are very important, considering the potential number of cancer diagnosis tests that one may wish to perform. Equally important, the novel invention, both in terms of the system and method, provides capabilities for separating biological cells from one another by placing each separated cell at a known address, to which one can return, for repeated cell observation and/or repeated stimulations followed by subsequent analysis.

Briefly, in accordance with the present invention a large number of cells, e.g., lymphocytes in the blood, which can be thought of as representing a group or population of cells, are first separated from all other cells, i.e., from different groups or populations of cells. After the separation process, the separated lymphocytes are subjected simultaneously to selected tests and thereafter each cell is separately investigated to determine whether or not, as a result of the test, or stimulation, it exhibits a particular property. The address of every cell exhibiting said property is recorded. Thus, after all the separated cells have been investigated the addresses of all the cells which exhibited the particular property are known. These cells represent a particular subgroup of lymphocytes within the larger entire group of lymphocytes. Once the cells in the subgroup have been identified, they together with the rest of the lymphocytes may be subjected to one or more additional tests. However, as to investigating the properties of the cells as a result of these additional test(s) it can be limited to only the cells in the subgroup. Each cell in the subgroup is individually investigated by directing the investigative instrumentation to the cell's unique known location or address. Thus, once the cells in the subgroup have been identified only they are subsequently investigated, while all other cells, through belonging to the same group, but not being part of the subgroup, are ignored in that they are not subjected to any investigation. Consequently once the subgroup has been identified only its cells are investigated, thereby limiting investigation time only to the subgroup cells which are of interest. Also, since the investigation is done on a cell-by-cell basis, more precise data is obtainable for increased diagnosis accuracy. Other advantages of being able to identify cells of a subgroup and investigate each one individually will be discussed hereinafter.

As previously pointed out, in a first step the lymphocytes are separated from the other cells contained in the blood. The separation is performed by means of a perforated cell carrier 1 as shown in FIG. 1A. The carrier includes base 3 in which are formed apertures or holes 2.

The cell carrier 1 may have various configuration of apertures of holes 2, as well as the manner in which they are arranged. In FIG. 1A they are assumed to be arranged in rows and columns along axes X and Y, respectively. The holes are shown as having larger openings at the tops than at the bottom thereof, as shown in FIG. 1B. The side walls of the apertures may converge continuously or in steps, as shown in FIG. 1C, towards the opening at the bottom side 1b of the cell carrier. Also, as shown in FIG. 1D, not all sides of the aperature need slope inwardly, Rather, a portion of the walls of the aperture can be essentially vertical so as to help capture and retain the cells in the apertures, especially when the cells are introduced into the carrier by being flowed across the top of the carrier in a direction substantially perpendicular to the apertures' vertical walls.

The shape of the apertures 2 enables the cells to be effectively held to the carrier by applying means, such as a pressure difference between the upper and the bottom side of the carrier, or electromagnetic forces. Briefly, to first separate a particular group of cells from cells of other groups, since the cells in each group are of known size or sizes, which typically differ from those in other groups, the carrier 1 is chosen to have holes of sizes so that when the matter, e.g., blood, containing the various cell groups is placed on the carrier 1, effectively most of not all of the holes are occupied by cells of the group of interest, one cell per hole.

In the specific examples described herein, the holes are sized to be suited for receiving lymphocytes, among which there are two main sizes of about 7 $\mu$m and about 10–15 $\mu$m, the 7 $\mu$m lymphocytes being the cells of interest. To capture and retain this population of cells, it has been found that at the upper surface of side 1t of carrier 1, the apertures should have a cross-sectional dimension of approximately 10 $\mu$m and that at the bottom surface or side 1b, they should have a cross-sectional dimension of approximately 5 $\mu$m. In this way, the desired population of cells can easily enter the aperture without suffering substantial damage and yet, once in the aperture, the cells cannot pass out of the bottom of the carrier.

In general the aperture should be shaped so that either at its bottom side or at a cross-section intermediate sides 1t and 1b the cross-sectional dimension is less than at the top side, so that a desired cell entering an aperture does not pass through the aperture, but rather is held therein. FIG. 1E illustrates an aperture configuration wherein the minimum cross-section is located in a plane intermediate between the top and bottom of the carrier. In addition to properly selecting the aperture's entering and exiting dimensions, it is also important to choose the carrier thickness between the top and the level of the minimum cross-sectional dimension so that the size of the aperture is related to the size of the desired cells so that when a desired cell enters an aperture practically the entire cell is within the aperture, thus preventing it from being washed out during a washing step, as will be described.

The carrier 1 is made of any appropriate matter, e.g., metals such as copper, gold, nickel, silver or others, or of plastic, which may be provided with electrically conducting portions, extending between the holes 2 as shown in FIG. 17. By using these conducting portions, as described below, the electric field at any cell-containing hole can be influenced to produce an interaction with the cell's electrical charge. By controlling the potential at various holes the cells therein can be electrically bonded to the carrier as well as be released therefrom.

In addition to using pure metal or plastic carriers, in some cases it is desirable to coat the carrier with various materials in order to change either or both of its chemical and mechanical surface characteristics. Examples of suitable coating materials include silicon, silicon dioxide and various inorganic glasses. When using such coating materials, or for that matter, when choosing a material from which to make an uncoated carrier, it is important to determine that the material does not interact with the cells in a way which will interfere with the test or tests to be performed.

For example, with regard to the Cercek SCM test described above, it has been found that a coating of $SiO_2$ on the carrier leads to activation of the cells (lymphocytes) which masks the response of these cells to stimulating agents. A similar activation is found with a mixture of silicon and $Si_2O_3$. Pure silicon, on the other hand, does not lead to activation of the cells. Accordingly, for the SCM test, a carrier coating of a silicon is appropriate, while a coating of silicon dioxide or silicon plus Si₂O₃ is not. Similar selections of coating materials can be readily made by persons skilled in the art for other types of diagnostic tests.

Figure 18:
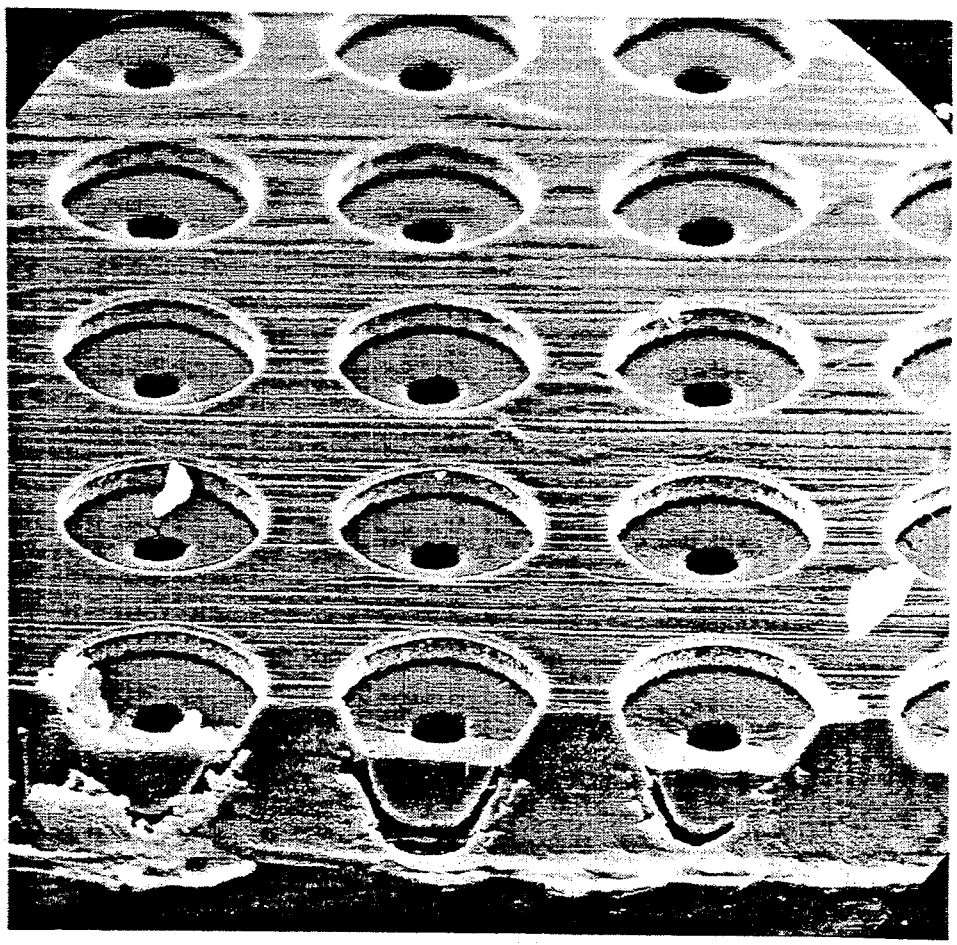
FIGS. 18–20 are scanning electron microgram of copper carriers.
Figure 19:
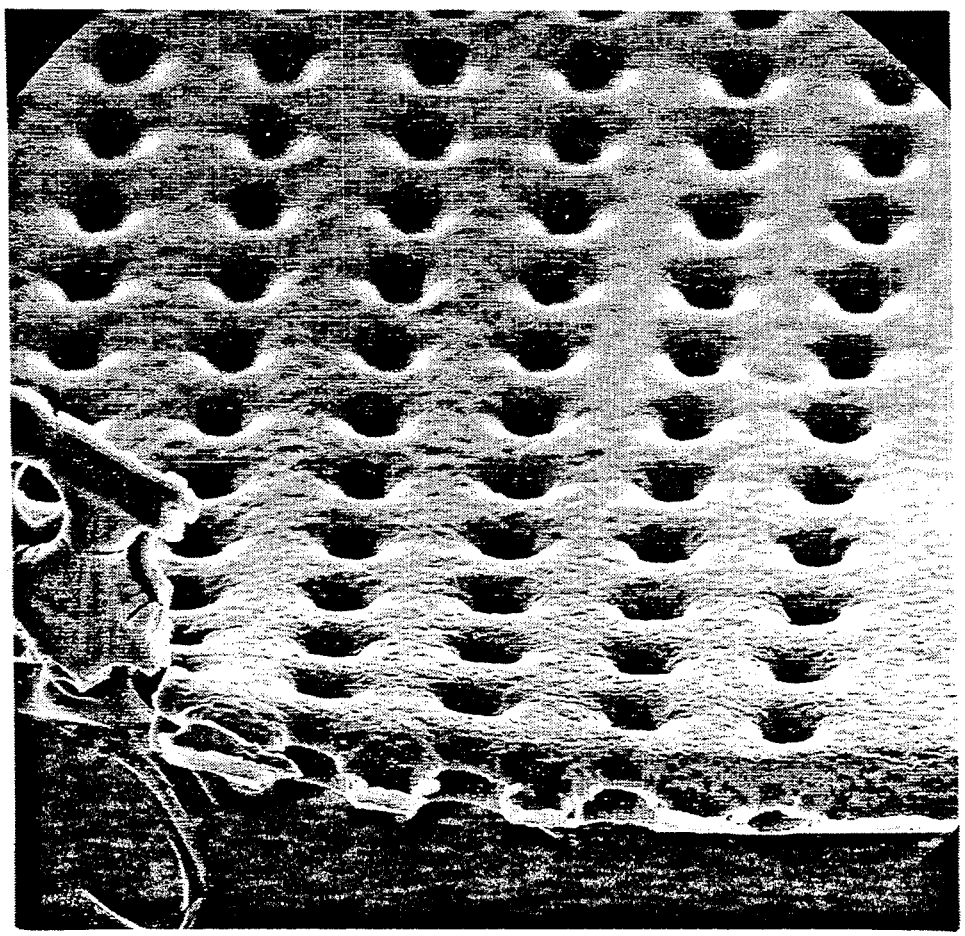
Figure 20:
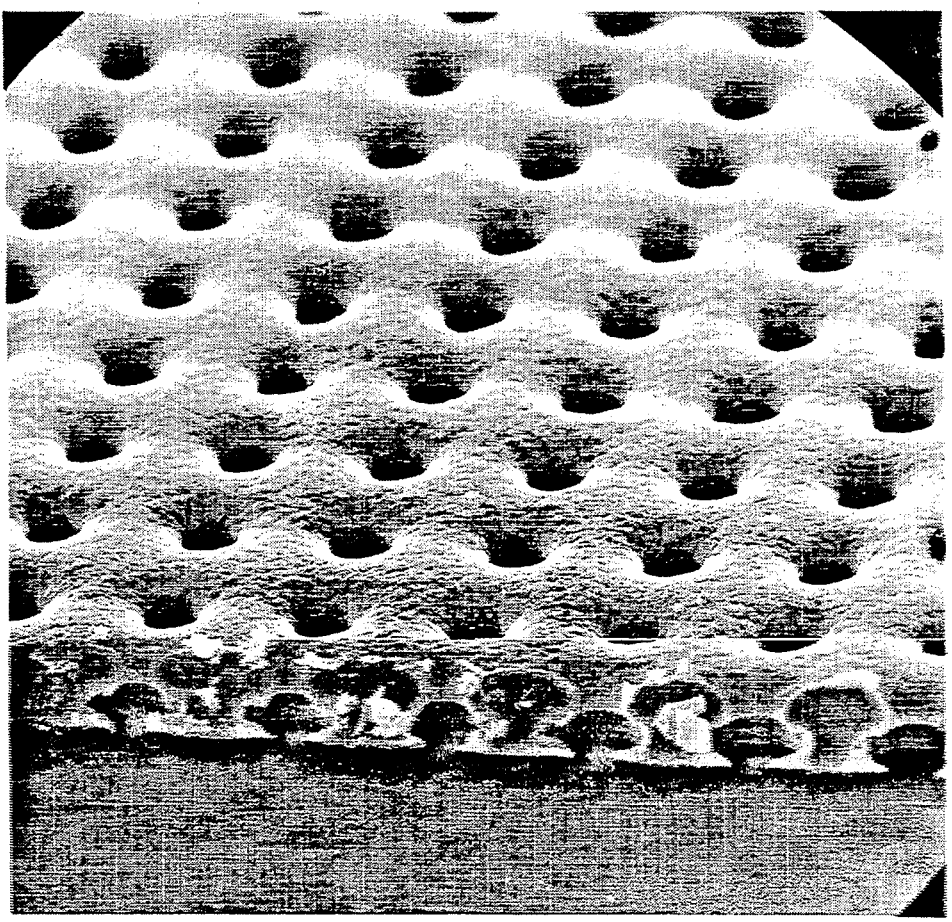

Scanning electron micrographs of a copper carrier for use with the present invention are shown in FIGS. 18, 19 and 20. FIG. 18 shows the top surface of the carrier at a magnification of 1000 X. At the level of this surface, the apertures have a cross-sectional dimension (diameter) of approximately 11 microns. The minimum cross-sectional dimension for these apertures is located in a plane intermediate the carrier's top and bottom surfaces and has a magnitude of approximately 4 microns. The spacing between this intermediate plane and the top surface of the carrier is approximately 6 microns. The spacing between apertures is approximately 15 microns. In general, the inter-aperture spacing should be kept as small as possible so as to maximize the chances that cells will come to rest inside apertures rather than on the portions of the carrier between apertures.

FIGS. 19 and 20 show the bottom surface of the carrier of FIG. 18 at a magnification of 1000 X. FIG. 19 also shows a turned-up corner of the carrier. Examining the edges of the carriers of FIGS. 18–20 reveals that the apertures have a vertical cross-sectional configuration of the type shown in FIG. 1E.

The carrier shown in FIGS. 18–20 was prepared using a standard photo-etching technique of the type commercially employed to make transmission electron microscope grids. As is known in the art, that process, in its last stages, involves the deposition of metal on one side of a preformed grid so as to increase the strength of the grid. When a transmission electron microscope grid is to be formed, the deposition step is carried on only for a short time so as to keep the size of the apertures as large as possible, i.e., to minimize the width of grid members which in turn minimizes the interference of the grid with the transmission of electrons through the specimen and to the electron detector. To form the carrier of FIGS. 18≧20, the deposition step, rather than being short, was continued for a relatively long period of time until enough metal was deposited on the back surface of the grid to fill in the apertures to the extent shown in the figures. As shown most clearly in FIG. 20, the deposited metal (copper) built up on the solid parts of the grid and overlapped into the apertures to close off the apertures and thus form the desired minimum cross-sectional dimension of the apertures.

Rather than using a deposition process to form carrier apertures of the desired configuration, other processes, in particular ion bombardment processes through masks of different thicknesses and the like, can be used. Such processes are particularly useful in preparing asymmetric apertures, such as those shown in FIG. 1 D.

Figure 21:
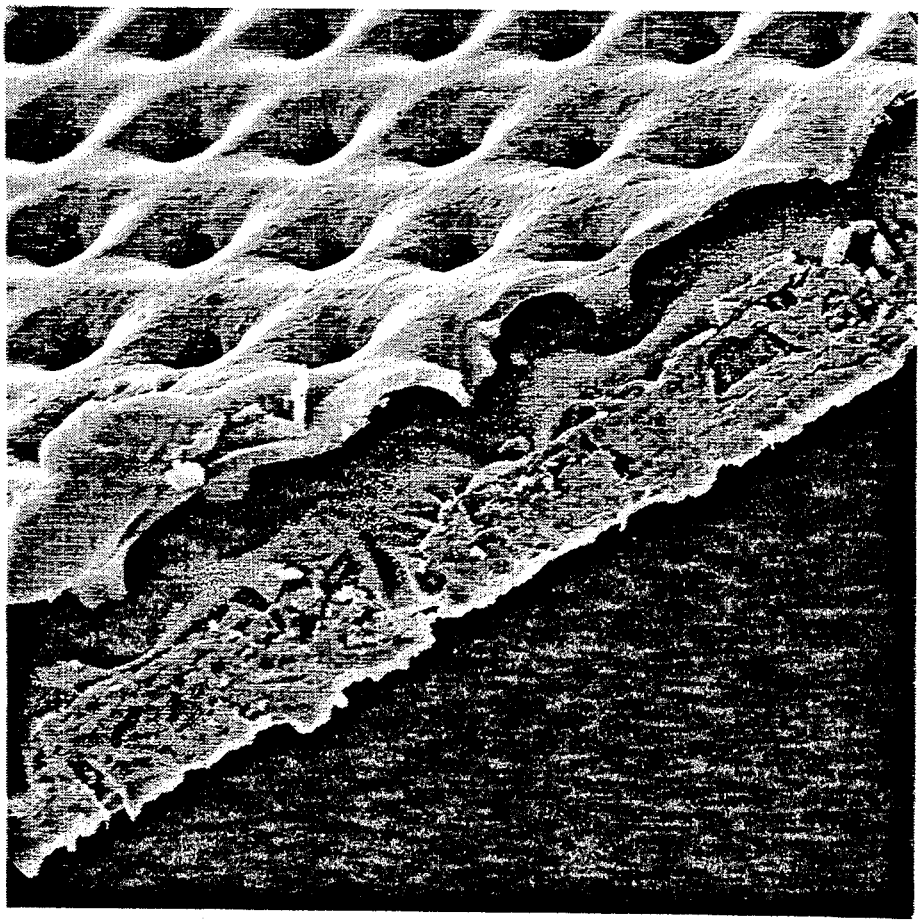
FIG. 21 is a scanning electron micrograph showing a copper carrier coated with silicon.

FIG. 21 is a scanning electron micrograph at a magnification of 720 x illustrating a coated carrier. The base carrier in this example was formed from copper and the coating is pure silicon which was deposited on the carrier by vapor deposition. As can be seen in FIG. 21, coatings can be used to change (reduce) the cross-sectional dimensions of the apertures, as well as to provide an especially smooth and/or inert surface for contacting the cells.

Figure 22:
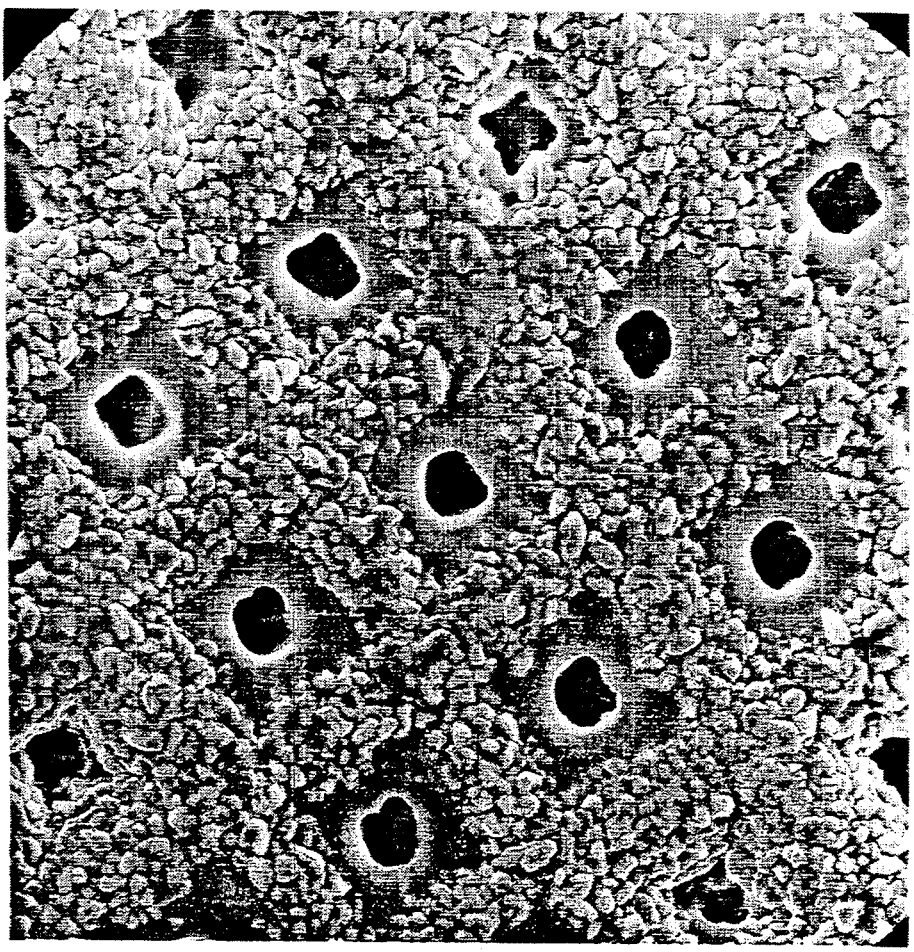
FIG. 22 is a scanning electron micrograph showing a copper carrier having square-shaped apertures which are sized to hold and retain lymphocytes having a cross-sectional dimension of approximately 7 $\mu m$.

FIG. 22 shows an uncoated copper carrier, in this case having square rather than circular apertures. The cross-sectional dimension of the apertures at the top surface of this carrier is approximately 10 microns and the minimum cross-sectional dimension (which lies in a plane 7–8 microns below the top surface of the carrier) is approximately 5 microns. The spacing between apertures is approximately 12 microns.

The holes in the carriers of FIGS. 18–20 and 22 are sized to be particularly well-suited to capturing and retaining lymphocytes having a cross-sectional size of approximately 7 μm. From the disclosure herein, it will be evident to persons skilled in the art that other carriers having different aperture configurations can be constructed for capturing and retaining cells of different types and sizes.

It will be apparent from the disclosure herein that the ordered array which characterizes the carriers of the invention preferably comprises at least one sub-group of uniformly shaped holes of such cross sectional dimensions that individual living cells of a particular identical size may be accommodated and held therewithin. Such preferred carriers may, in a particular embodiment, comprise at least first and second sub-groups of respectively uniformly shaped holes, wherein the cross sectional dimensions of the first sub-group are different from the cross sectional dimensions of at least the second sub group, whereby the holes in said first sub-group are dimensioned to hold individual living cells of a preselected first size therewithin, and the holes in at least the second sub-group are dimensioned to hold individual living cells of a preselected second size therewithin, which cells are different from the cells of said preselected first size. In other words, a carrier of the invention may be so constructed that it contains two or more sub-groups of holes which are identically dimensioned within each sub-group, but differ in dimensions from one sub-group to another. The dimensions of the holes in each sub-group may be such that each sub-group is capable of accommodating a particular size of cell in its holes, differing in size from the size of cells which may be accommodated in at least one other sub-group.

A carrier according to the invention which contains e.g. two sub-groups of hole sizes may be prepared in a non-limitative manner as follows. A sketch approximately 20 cm×20 cm. is prepared of white spots on a black background. Each white spot has one of two standard diameters which on photoreduction will give micro-spots of the desired preselected two sizes. The size of the sketch is reduced 40× photographically, and the reduced photograph is used as a mask. The mask is placed on a highly polished copper plate of approximately 0.5 mm. thickness, the plate having been previously coated with polymerizable photoresist material to a desired height, e.g. 7 microns. The masked plate is exposed to light, the latent image in the photoresist layer is developed and fixed, and unpolymerized photoresist is washed away. There remain on the plate columns of photoresist of two sets of diameters corresponding to the maximum respective diameters of the two sets of holes desired in the carrier. The plate is now electroplated, e.g. with nickel, which deposits on those portions of the copper containing no residual photoresist. In the course of the electroplating process, once the deposited metal such as nickel reaches the height of the photoresist columns, it will then deposit not only on the surface of the previously deposited metal parallel to the plate, but slowly, though progressively, on the inside of the holes above the level of the photoresist columns. In the nickel foil which is formed by electroplating, there will exist two sets of holes; in each set of holes the largest hole diameter will be that of the photoresist column, but there will also be a smaller hole diameter less than that of the photoresist column. The electroplating process is stopped when the smaller hole diameters have reached the desired size, and the foil is carefully peeled from the plate.

Other methods may of course be used and will suggest themselves to those skilled in the art. For example, a metal carrier with a set of holes of uniform size may first be prepared as described herein, a limited area of the carrier is then masked, the surface of the unmasked area is coated with a film of peelable material (while avoiding coating over the holes) to prevent deposition of metal other than in the holes, and the masked and coated carrier is subjected to a metal vapor deposition process; the resultant product, after removing the mask and peeling off the film, contains holes of the original size, where the mask was applied, and holes of restricted size in the unmasked area where metal has been vapor deposited.

It will be apparent that the methods which may be used to make a carrier according to the invention having two sets of hole sizes may readily be adapted to make holes containing three or more sets of hole sizes, if desired.

As previously pointed out, the holes 2 in carrier 1 are regularly arranged over or in the carrier, e.g. in rows and columns, to enable a clear identification of the position of every hole 2, for example, by its X and Y coordinates in the plane of the carrier. In the described embodiment the holes are disposed in rows and columns, extending perpendicularly to each other, thereby forming a matrix-like structure. The number of holes is chosen depending on the number of cells to be carried. For example, with 100 holes per row and column there is a total of 10,000 holes to carry 10,000 cells on the carrier of the described embodiment, each with its unique position in X and Y. The carrier 1 itself may have a circular circumference, as can be seen from FIG. 6C. As shown therein the carrier has a plurality of ears 8, to align the carrier in a holder structure 40 which has a pair of indentations 9 extending from a top recess in which the carrier is supported. A hole extends axially about said recess in holder 40. Other aligning means such as pins or particularly shaped, e.g. triangular shaped, carriers are also within the scope of the present invention.

It will therefore be appreciated that in general terms the apertured cell carrier of the present invention may be supported on a holder, in which case the carrier is preferably constructed to include a device for aligning it with a complementary device on the holder (e.g. as described above), whereby the individual addresses of holes in the carrier are identifiable by a set of x and y coordinates, as for example when the carrier is viewed through a microscope.

In a particular embodiment, the carrier may be integral with a holder. Thus, for example, there is described and claimed (inter alia) in European Patent Application No. 0213902, published Mar. 11, 1987 (which derives priority from U.S. Ser. No. 771315 filed Aug. 30, 1985, now U.S. Pat. No. 4,772,540, in which the Applicant is the present Assignee, a microsieve integral with a supporting frame, and methods for making such. By utilizing one or more methods disclosed in this published European Patent Application, for example, the present carriers may be manufactured integral with a holder. In an alternative procedure, the present carriers may first be manufactured as described elsewhere herein, and then mounted on a support so as to be integral therewith, e.g. as described and claimed in commonly assigned U.S. Pat. No. 4,675,065, which issued Jun. 23, 1987 to Gordon. The disclosures in published European Patent Application No. 0213902 and in U.S. Pat. No. 4,675,065 are incorporated herein by reference.

A few drops of a solution containing cells to be separated by employing the carriers of the invention, e.g. blood containing the desired lymphocytes, may be dripped onto the carrier. A force such as a pressure differential may be applied across the carrier to move the cells into the apertures. The liquid passes through the holes in the carrier, while the cells are retained thereby. Since the sizes of holes 2 are preselected to accommodate lymphocytes only, they enter the holes, one lymphocyte occupying one hole. Cells in excess of the number of holes, and different cells e.g. of a size too big for the holes, may be washed from the surface of the carrier. Thereafter, in order to prevent cells leaving the holes in the carrier, they may be fixed therein by various means, e.g. by applying a continuous pressure differential across the holes, by changing the osmolarity of the bathing solution to cause the cells to swell, by covering the carrier by an adhesive, colloidable matter, and by electrically charging the carrier, as well as by external electric and/or magnetic fields. Another combined method for isolating said population and simultaneously applying it to the carrier will be discussed later in connection with FIGS. 10, 11, 12A and 12B.

Figure 23:
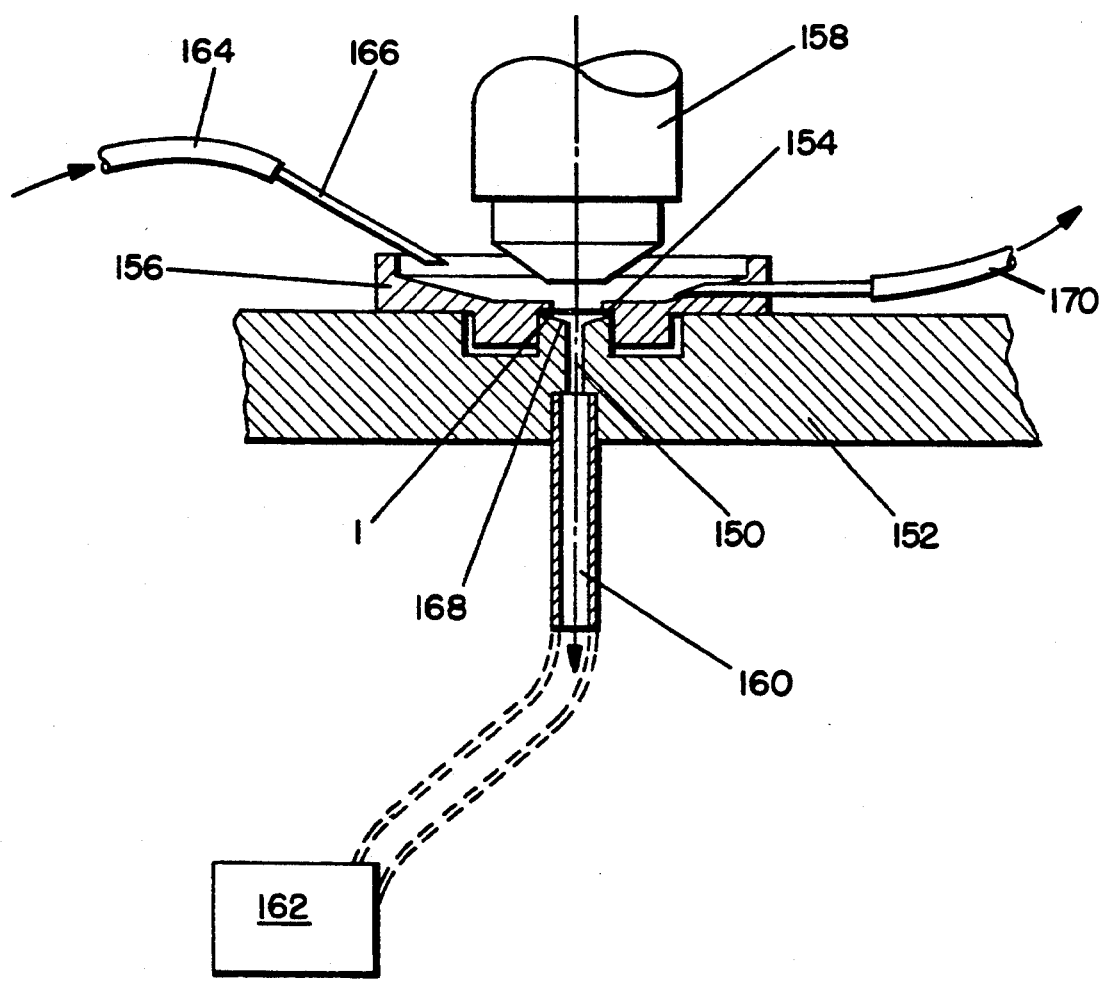
FIG. 23 shows a typical experimental arrangement for loading cells into carriers of the types shown in FIGS. 18–22.

FIG. 23 illustrates a typical experimental arrangement which has been used to load cells into carriers of the types shown in FIGS. 18-22.

Carrier 1 is held in place above orifice 150 in plate 152 by means of collar 154 of solution basin 156. The collar presses the carrier against the portion of plate 152 which surrounds orifice 150 and creates a seal between that portion and the carrier. This seal prevents substantial numbers of cells from passing around the edges of the carrier, rather than being captured in the apertures.

Orifice 150 is connected by outflow tube 160 to pump 162. The pump serves to produce a pressure differential across carrier 1 which pulls the cells into the apertures in the carrier. It has been found that a more uniform filling of carrier 1 can be achieved by providing a shallow taper 168 at the mouth of orifice 150. This taper reduces the amount of time required to fill the apertures at the perimeter of the carrier.

Basin 156 is configured so as to allow microscope objective 158 to be brought close enough to carrier 1 so that the apertures in in the carrier can be brought into focus. Solutions are provided to basin 156 by one or more inflow tubes 164 which are conveniently connected to syringe needles 166. The inflow tubes are used to introduce various bathing and reagent solutions to basin 156. The inflow tubes are also used to wash excess cells off the top surface of carrier 1. In this case, fluid is removed from basin 156 by means of drain tube 170. Cells are applied to carrier 1 using a standard syringe. During this operation microscope objective 158 and basin 156 are moved apart to allow ready access to carrier 1. The level of fluid in basin 156 is monitored during the testing of cells and, as necessary, fluid is added to the basin to keep the cells captured in carrier 1 continuously submerged in liquid.

A typical procedure used to capture and retain human lymphocytes in a carrier using the apparatus of FIG. 23 was as follows. First, a sample of human whole blood was obtained in the standard way. A plasma fraction of this blood was then obtained by either centrifuging the sample at approximately 100 g for approximately 6 minutes or by incubating the sample at 37° C. for approximately a half an hour. In either case, the plasma fraction had a pinkish cast indicating the presence of red blood cells. The red blood cell/white blood cell ratio of the plasma fractions used to fill carriers was estimated to be approximately 30/1.

Once obtained, the plasma fractions were diluted with phosphate buffered saline until a cell concentration of either approximately $6 \times 10^6$ cells/cc or $12 \times 10^6$ cells/cc was reached. So that the cells would fluoresce and thus be easily seen under the microscope during loading onto the carrier, fluorescein diacetate (FDA) was added to the cell suspension at a concentration of approximately 2.5 $\mu$M and the cells were incubated with the FDA for approximately 10–30 seconds prior to being applied to the carrier.

To make sure that the carrier was free from contamination, phosphate buffered saline was added to basin 154 with carrier 1 in place and pumped through carrier 1 by means of pump 162. Pump 162 was adjusted to produce a pressure differential across carrier 1 in the range of 0.5–5.0 cm of water.

The cells were applied to carrier 1 by bringing a standard syringe containing the cell suspension into the vicinity of the carrier. For the $6 \times 10^6$ cells/cc concentration it was found that three drops of the cell suspension applied near to, but not directly on, the carrier were adequate to essentially fill all of the aperatures in a carrier having approximately 7500 holes, while for the $12 \times 10^6$ cells/cc concentration level and the same size carrier, one drop applied directly to the carrier was found to be sufficient. In either case, essentially complete filling of the carrier occurred within a period of seconds to minutes, depending on how well collar 154 sealed the carrier to plate 152.

Figure 24:
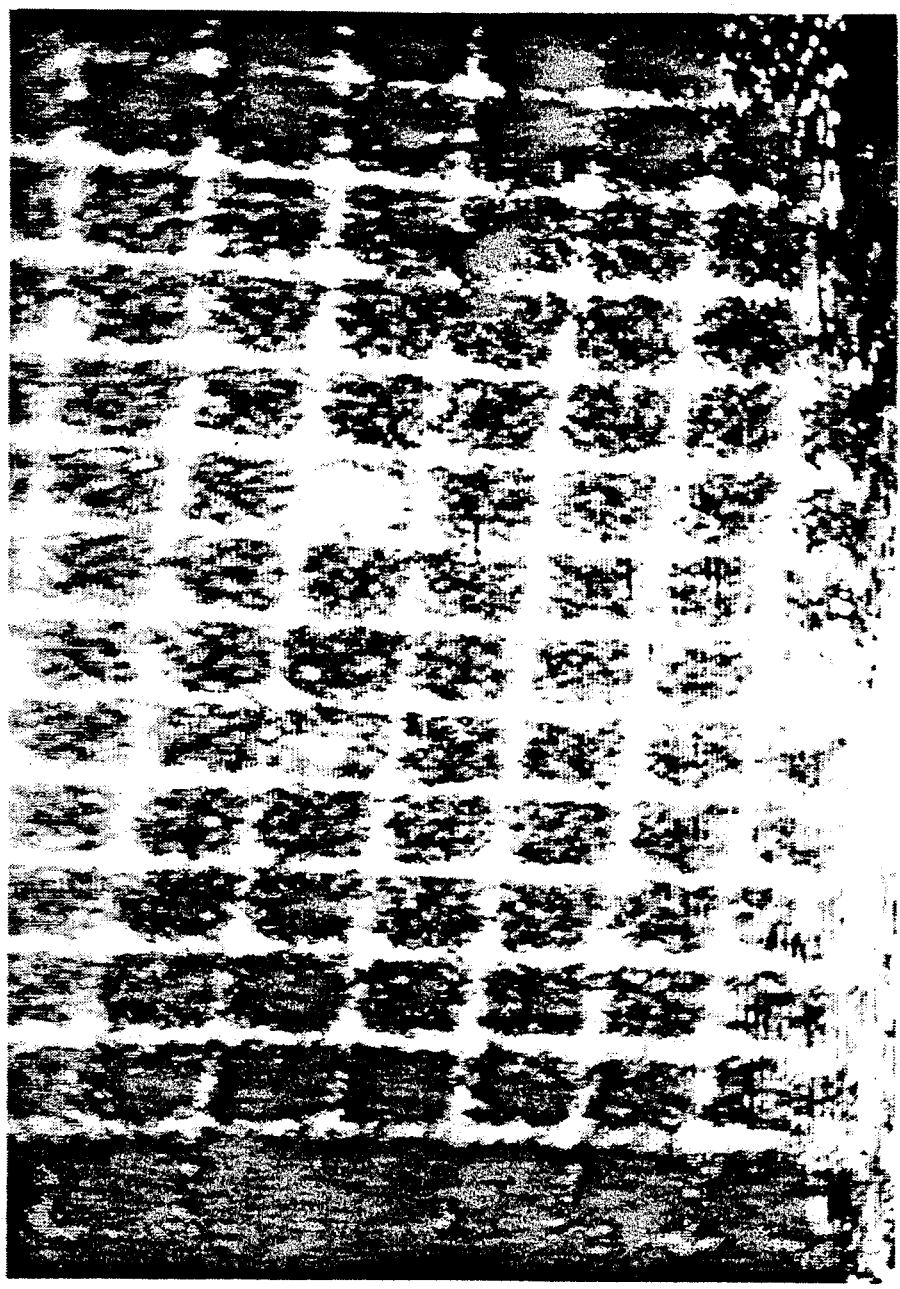
FIGS. 24–26 illustrate the process of filling a carrier with cells.
Figure 25:
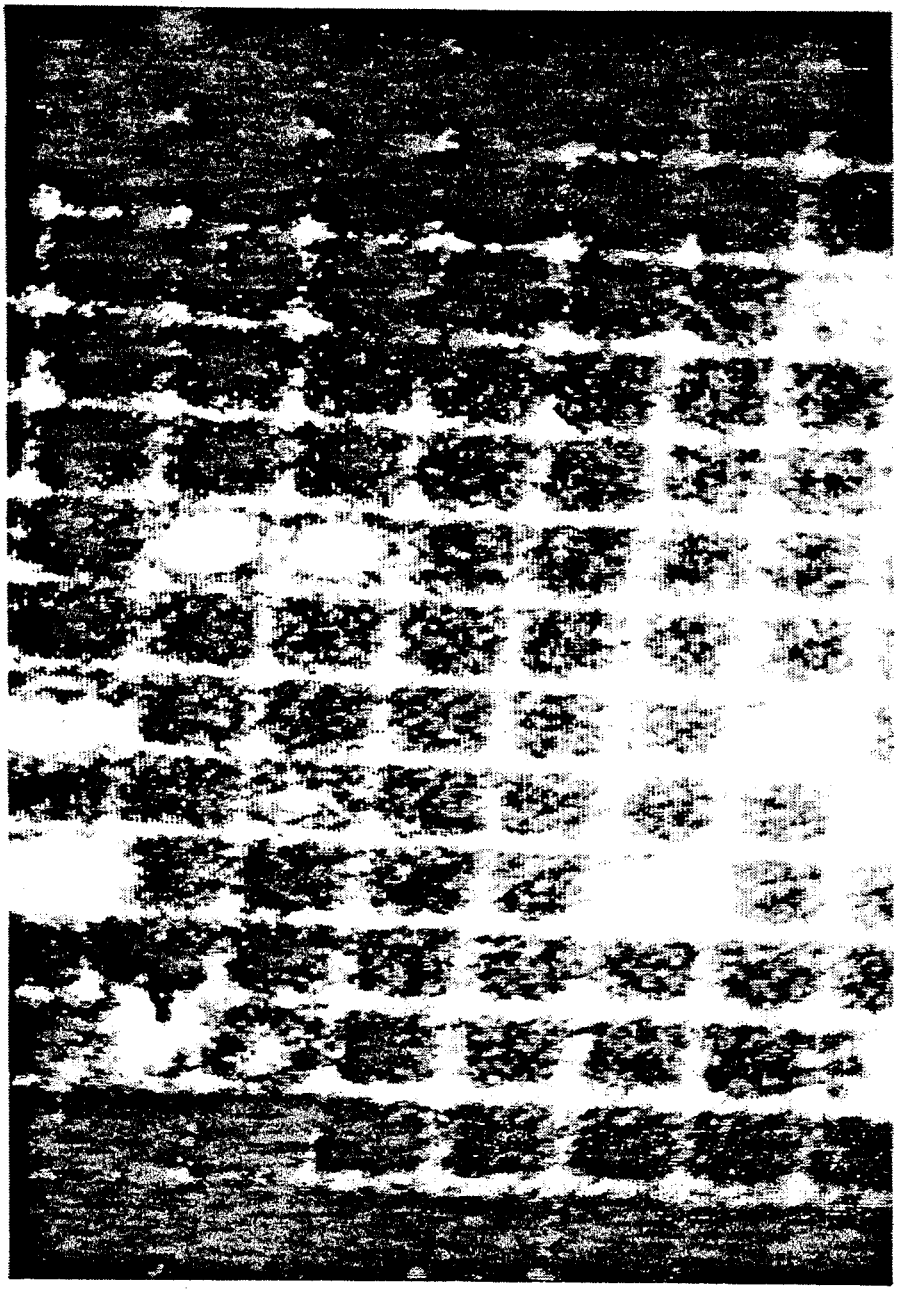
Figure 26:
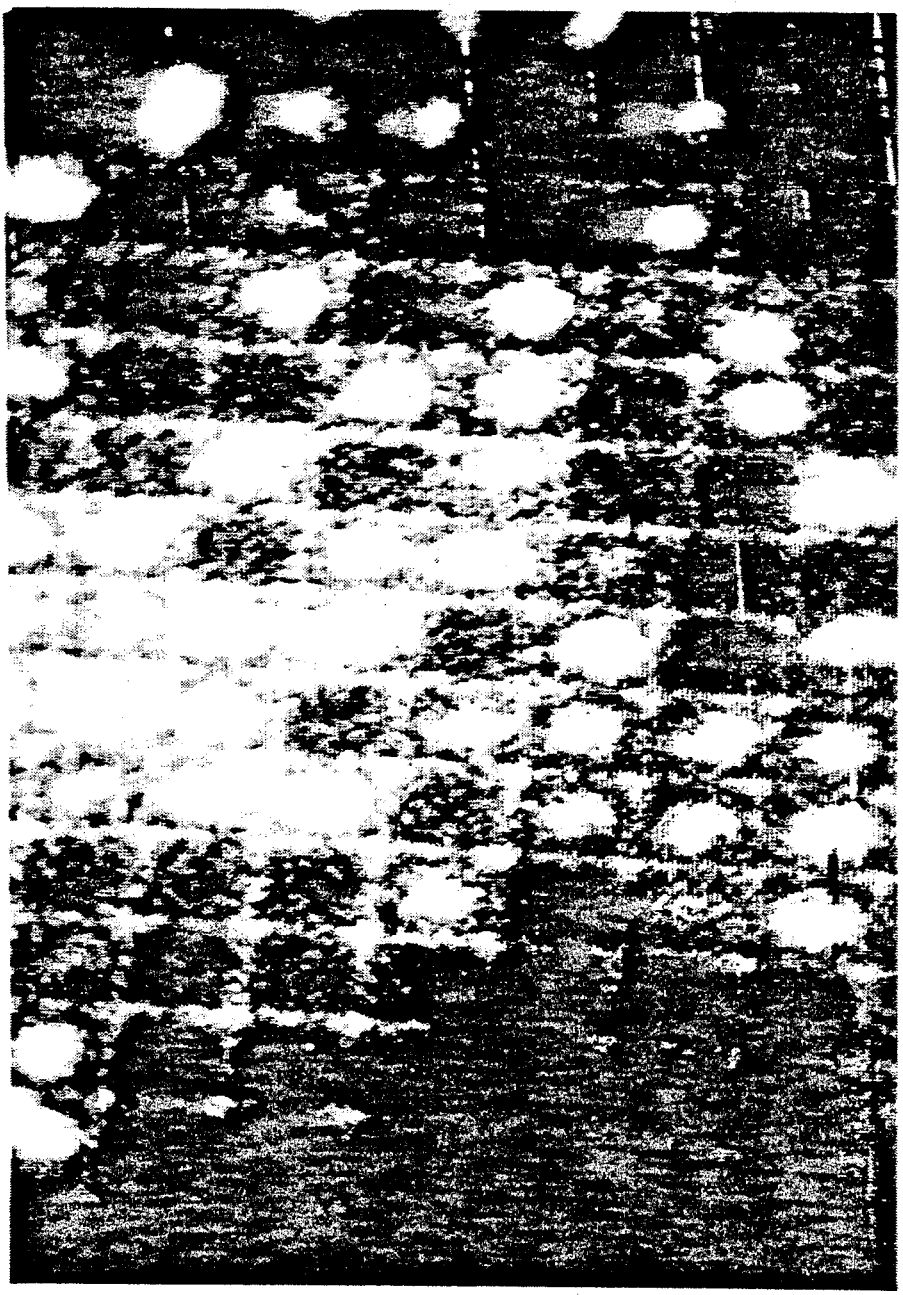

FIGS. 24–26 illustrate the filling process. Each of these figures is a still photograph of a videotape prepared during the filling of apertures using the apparatus of FIG. 23 and a carrier of the type shown in FIG. 22. FIG. 24 shows an essentially empty carrier at the beginning of the filling process. FIG. 25 shows the carrier partially full, and FIG. 26 shows a late stage of the filling process. The elapsed time between FIGS. 24 and 26 was on the order of a few seconds.

Figure 27:
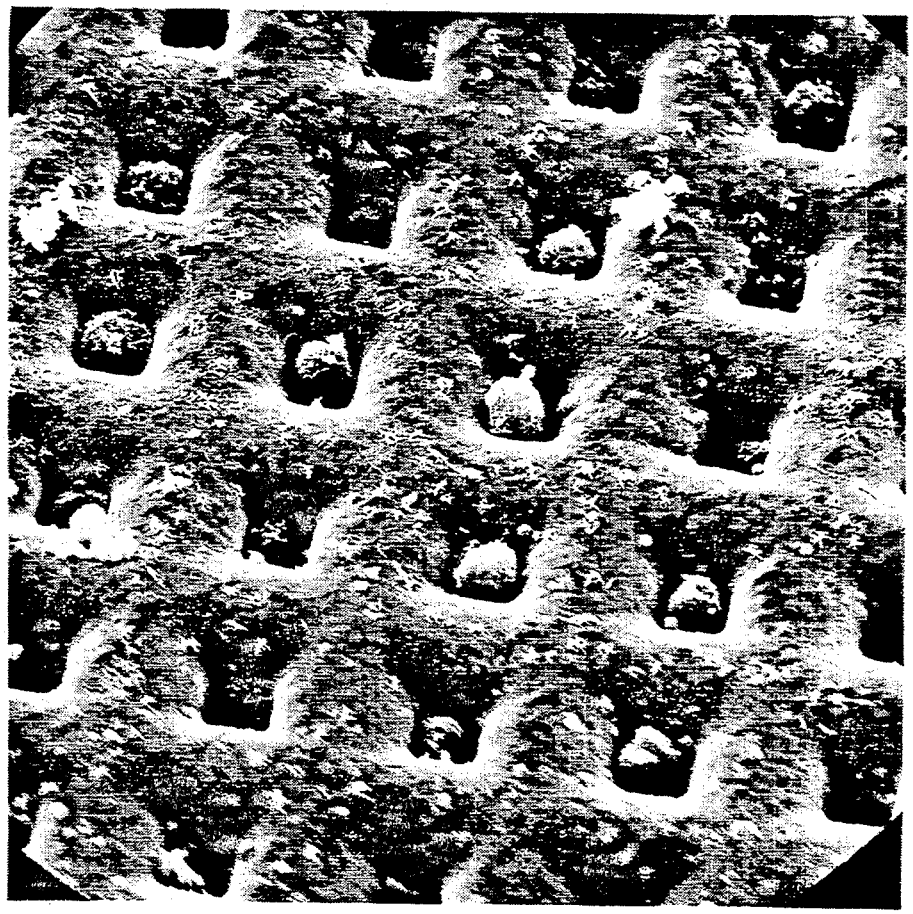
FIGS. 27–28 are scanning electron micrographs showing a carrier filled with lymphocytes.
Figure 28:
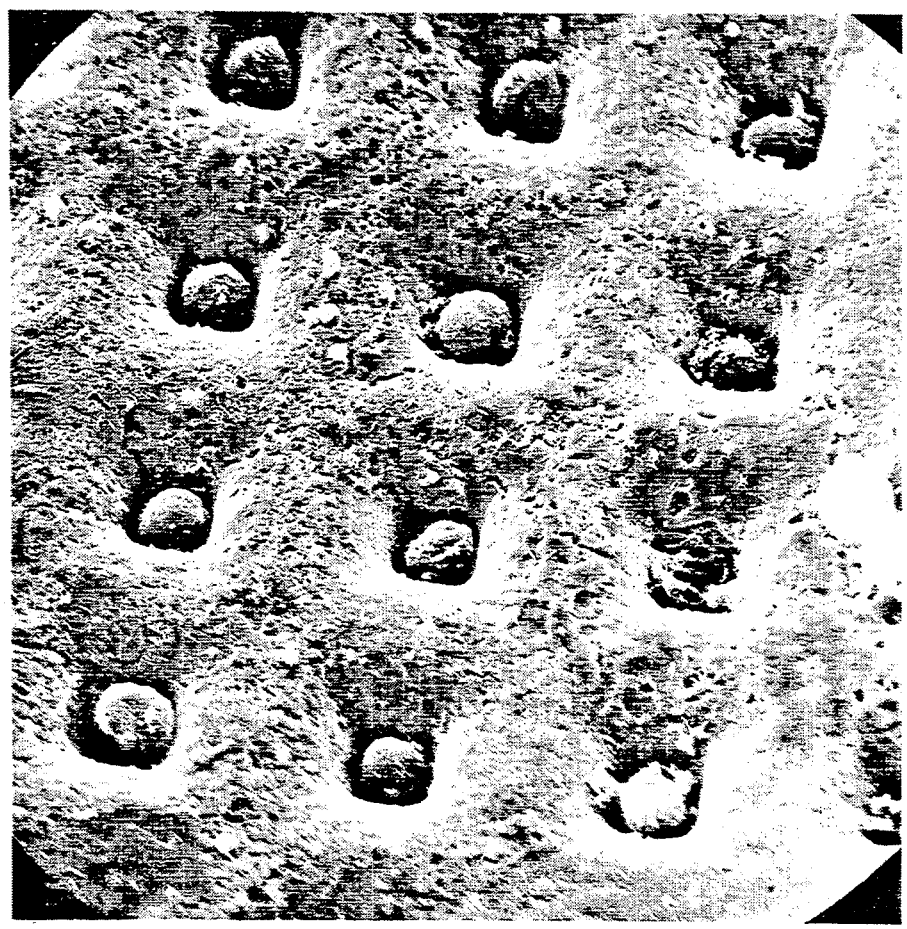

FIGS. 27 and 28 are scanning electron micrographs at magnifications of 780 X and 1000 X respectively, showing the carrier filled with lymphocytes. The fixation process used to prepare these micrographs causes the cells to contract. The makes them appear somewhat smaller than the apertures. When the cells were alive, they essentially filled the whole aperture with their tops at or just below the top surface of the carrier.

Figure 29:
FIGS. 29–32 are scanning electron micrographs showing individual cells in individual apertures of a carrier.
Figure 30:
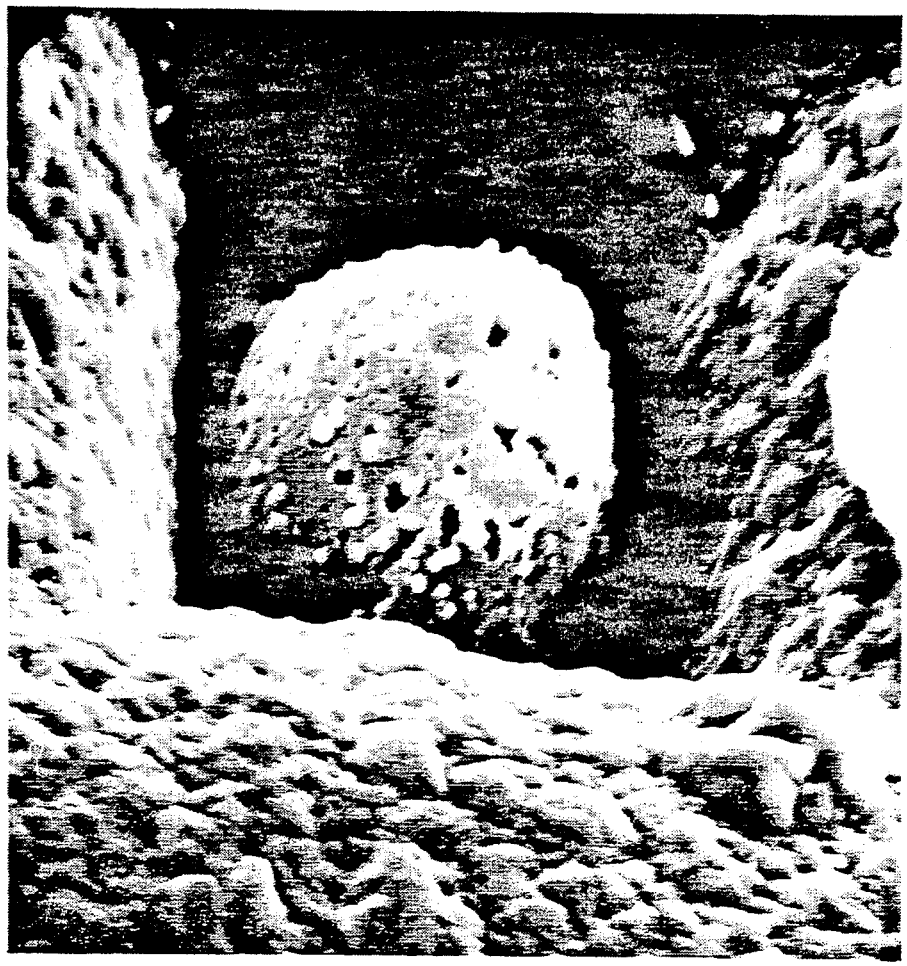
Figure 31:
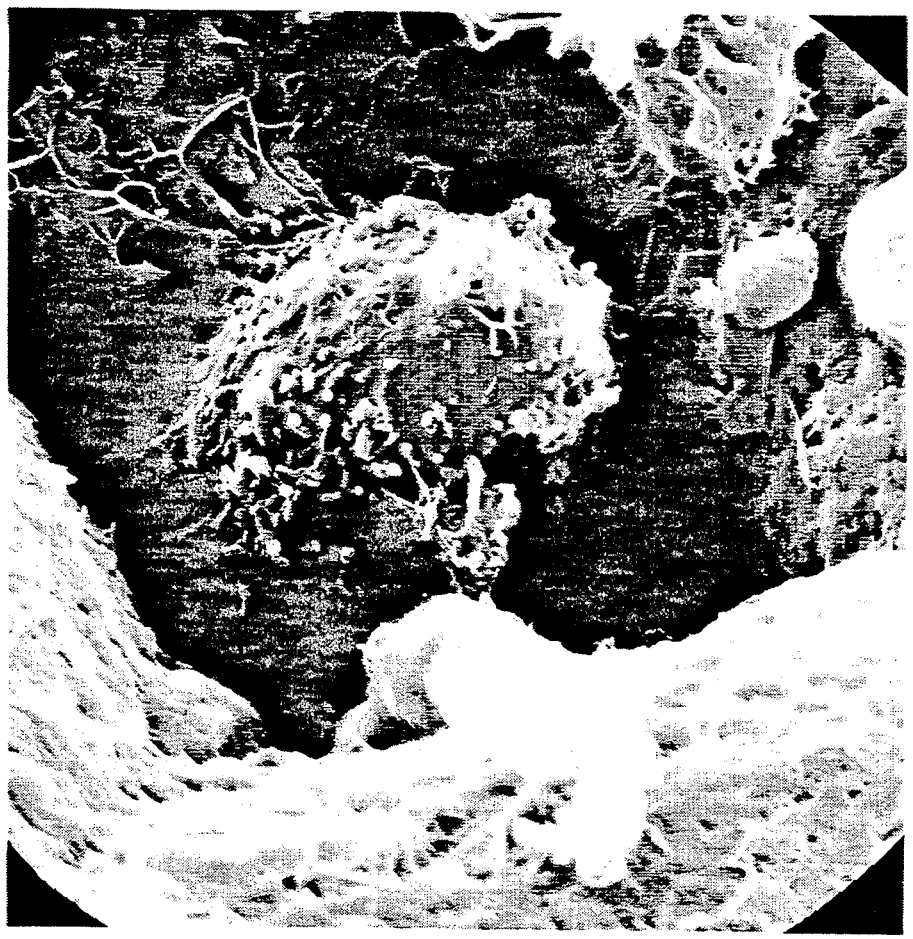
Figure 32:
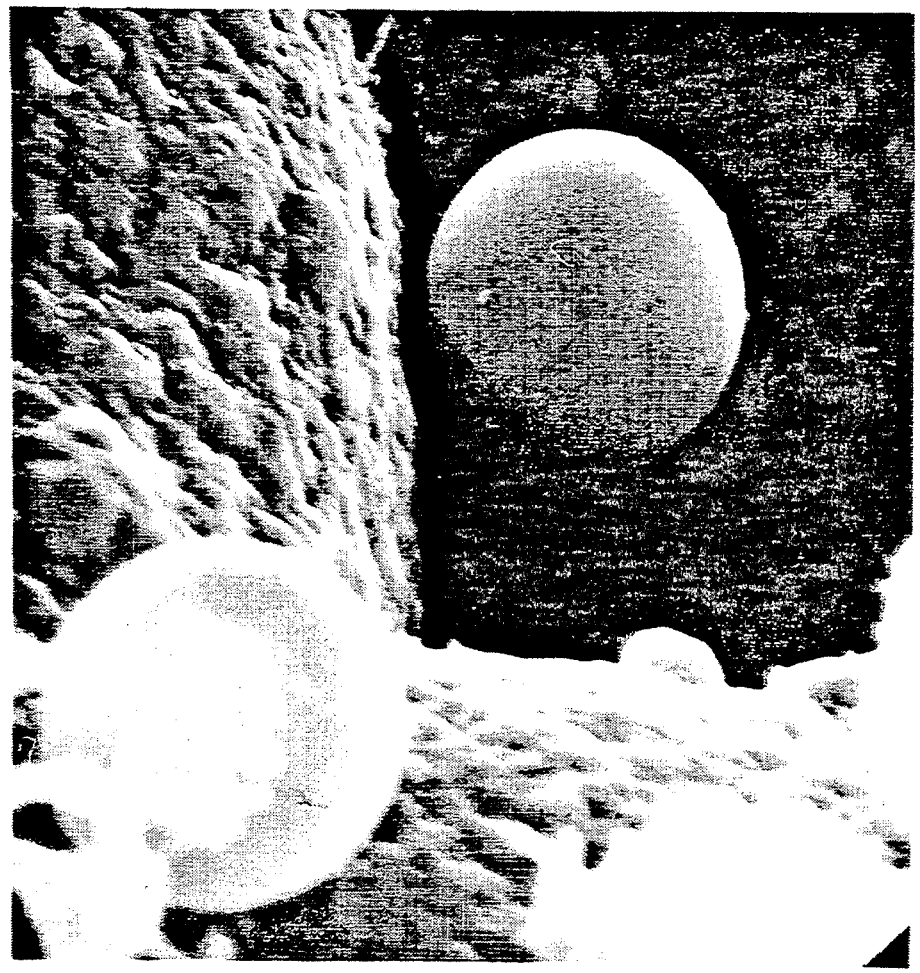

FIGS. 29–32 are scanning electron micrographs at magnifications of 4400 X, 5400 X, 6600 X and 6600 X, respectively, showing individual cells in individual apertures. The cells shown in FIGS. 29–31 are lymphocytes, while the cell in the aperture in FIG. 32 is an erythrocyte. Because erythrocytes are smaller than lymphocytes and are relatively flexible, if pressure had continued to be applied across the carrier, the erythrocyte shown in FIG. 32 would have passed down and out of the aperture.

Figure 33:
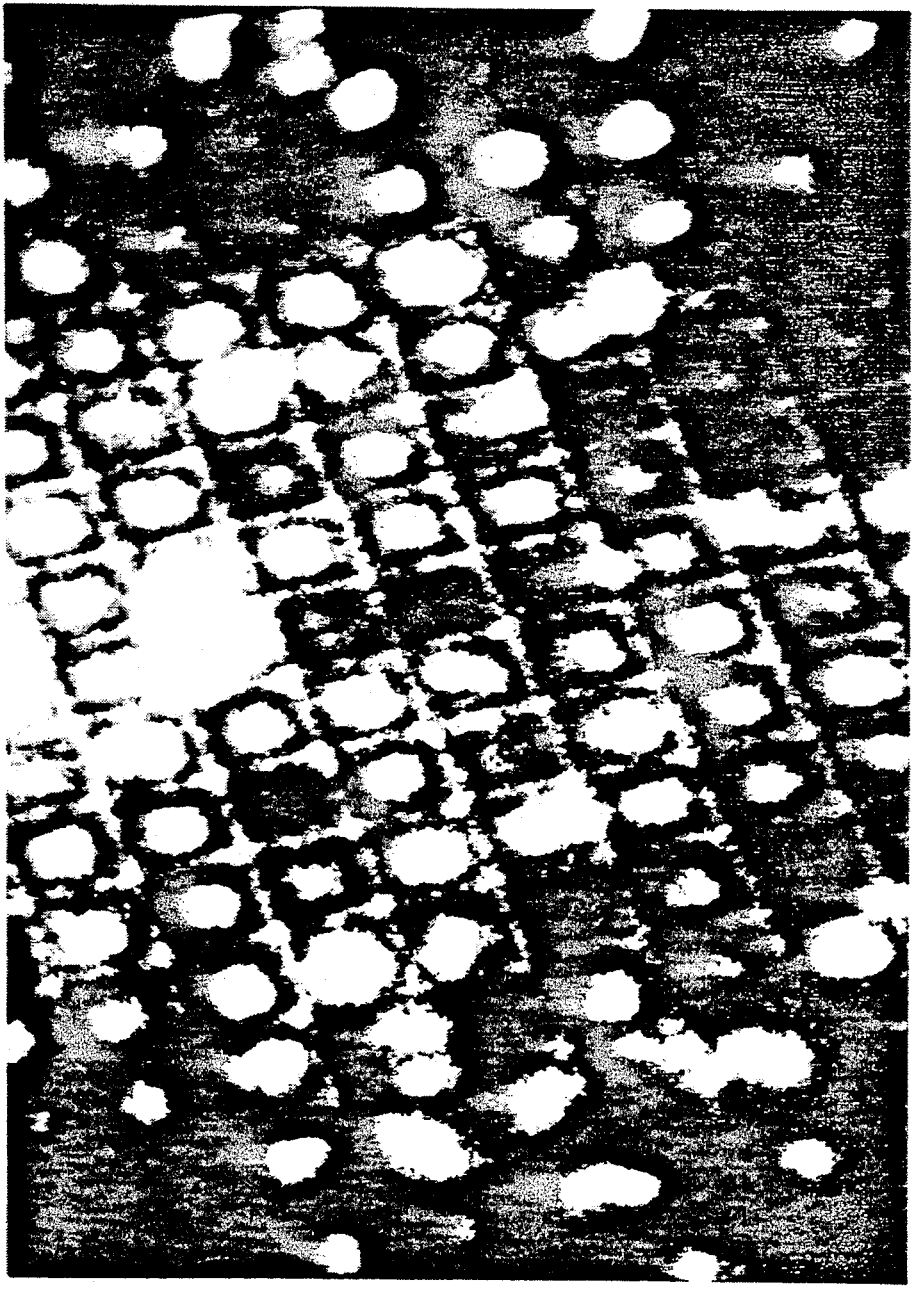
FIGS. 33–34 illustrate the process of washing the carrier to remove excess cells and debris.
Figure 34:

FIGS. 33–34 are a sequence of still photographs of a videotape illustrating the effect of washing the carrier to remove excess cells and debris, using inflow tube 164 and drain tube 170 of FIG. 23. FIG. 33 shows the surface of the carrier after filling, but before washing. As can be seen, the apertures have been filled with cells, but there still remain additional cells and other matter on the top surface of the carrier. FIG. 34 shows the clean carrier after one wash has been applied to the carrier. The cells are still in their apertures, but the top surface of the carrier is now nearly free of excess cells and debris. Note that the pressure differential created by pump 162, as well as the configuration of the apertures, serves to hold the cells in their apertures during the washing process.

Figure 35:
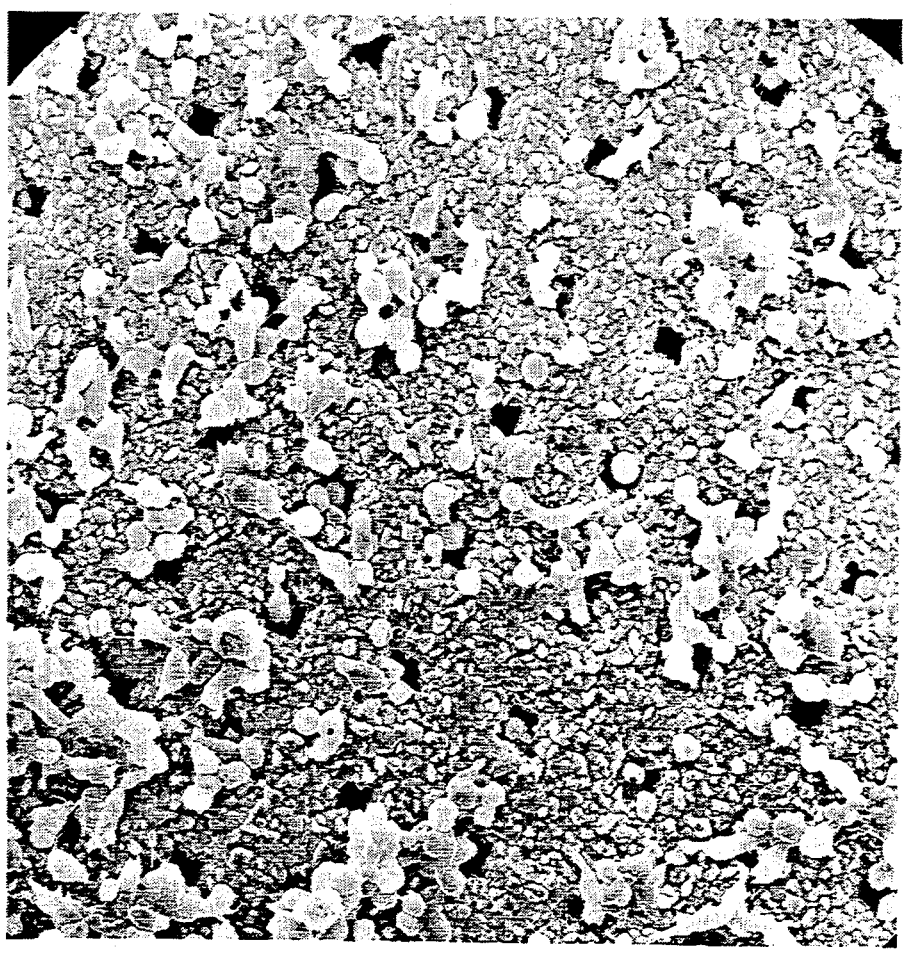
FIGS. 35–36 are scanning electron micrographs showing the surface of the carrier prior to washing.
Figure 36:
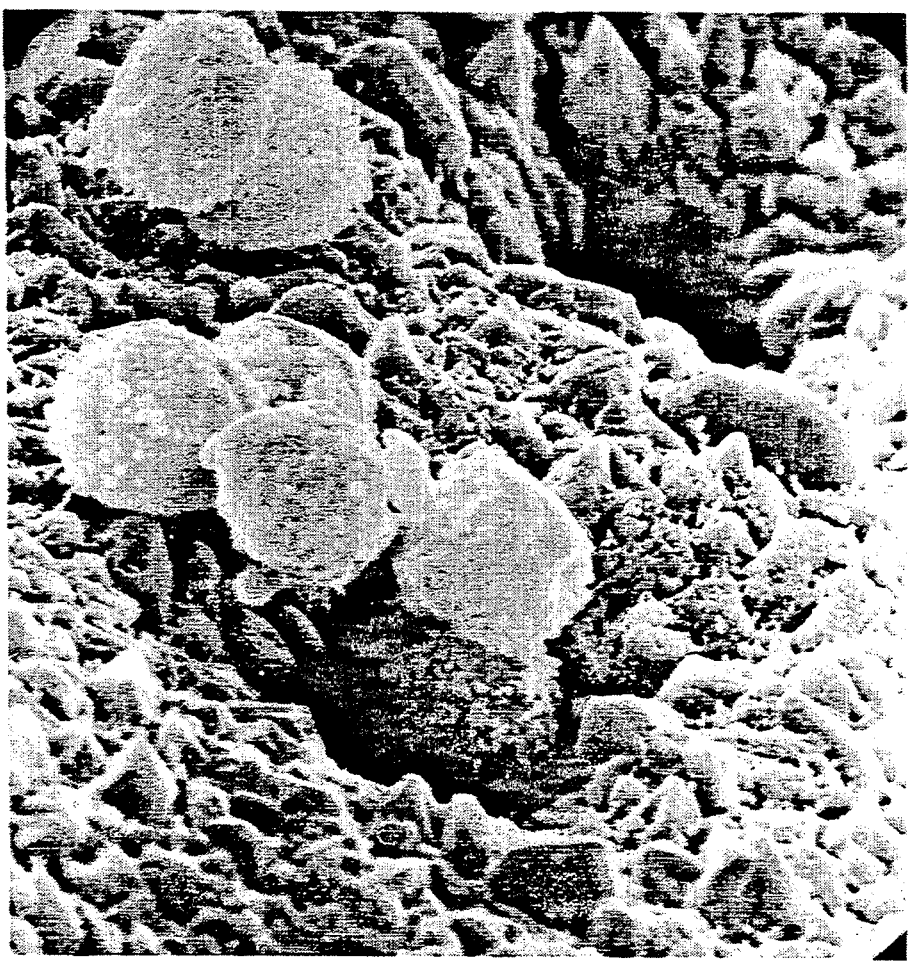
Figure 37:
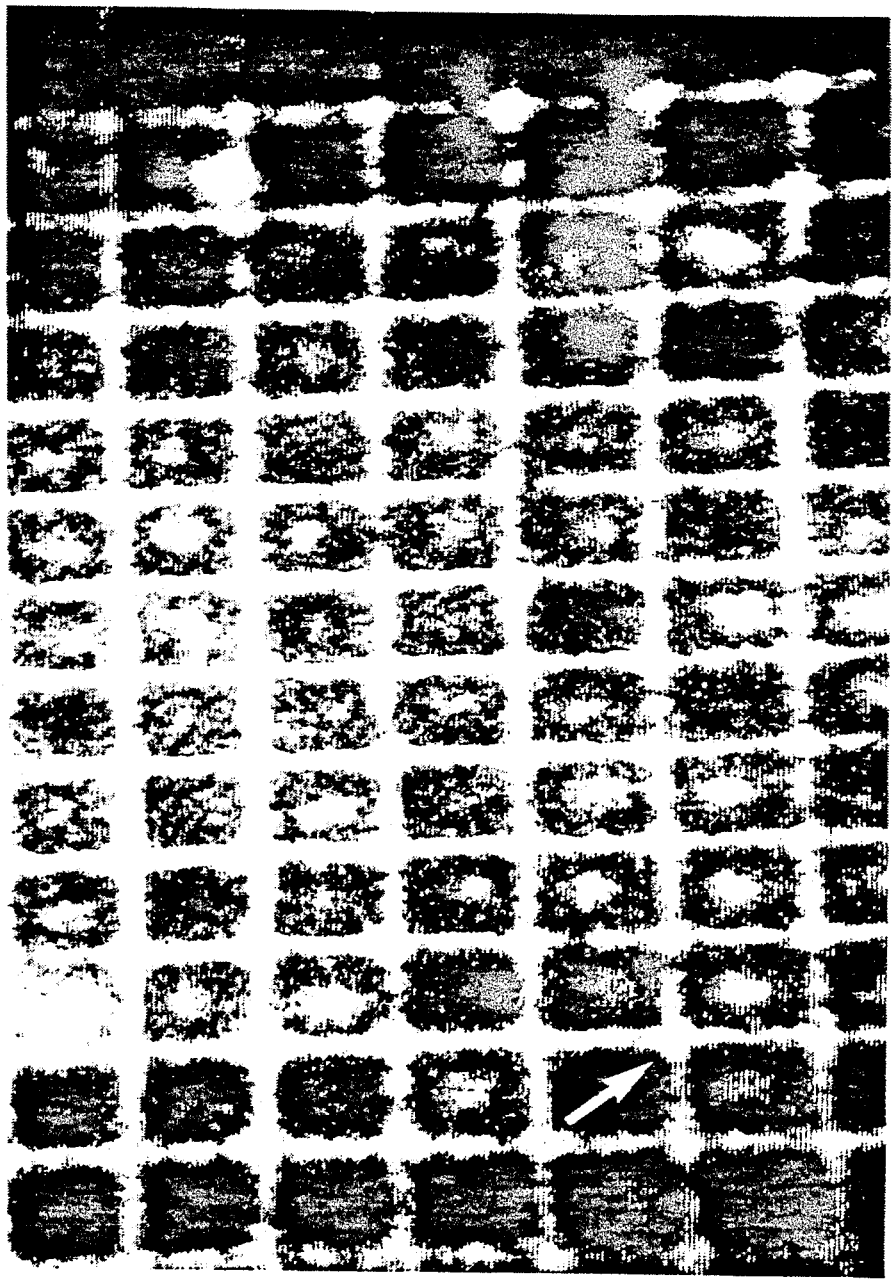
FIGS. 37–41 are a sequence of still videotape photographs showing that cells are not permanently bound to the carrier.
Figure 38:
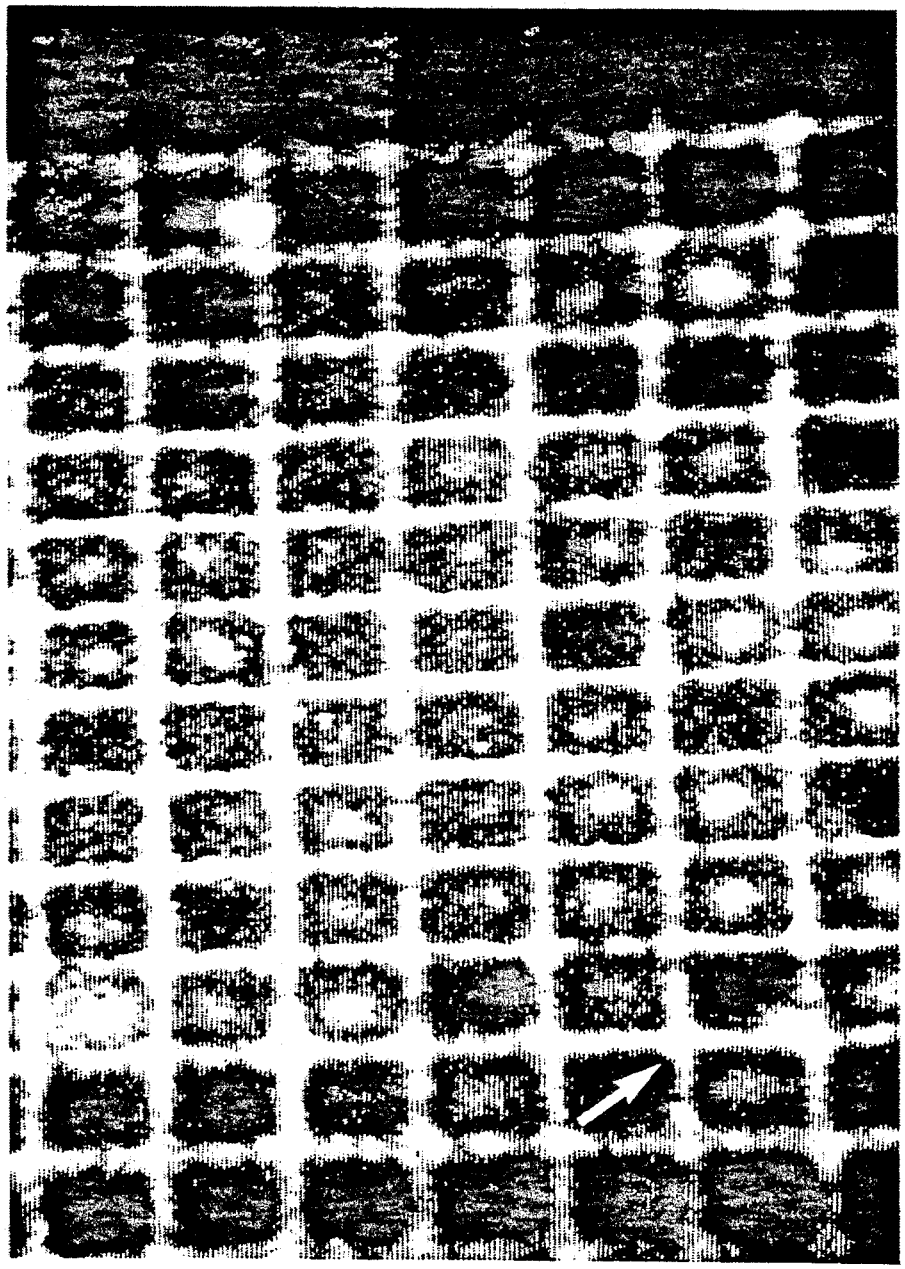

FIGS. 35–36 are scanning electron micrographs at magnifications of 480X and 320X, respectively, showing the carrier surface prior to washing. As can be seen in FIG. 35, there are individual lymphocytes in individual apertures, but the top of the carrier is covered with both excess lymphocytes and erythrocytes, as well as other cell types and debris. FIG. 36 shows an individual aperture holding an individual lymphocyte with other lymphocytes surrounding the captured lymphocyte. Comparing FIGS. 35–36 with FIGS. 27–28, which show the carrier surface after washing, clearly demonstrates the effectiveness of the washing process in removing excess cells and debris.

Figure 39:
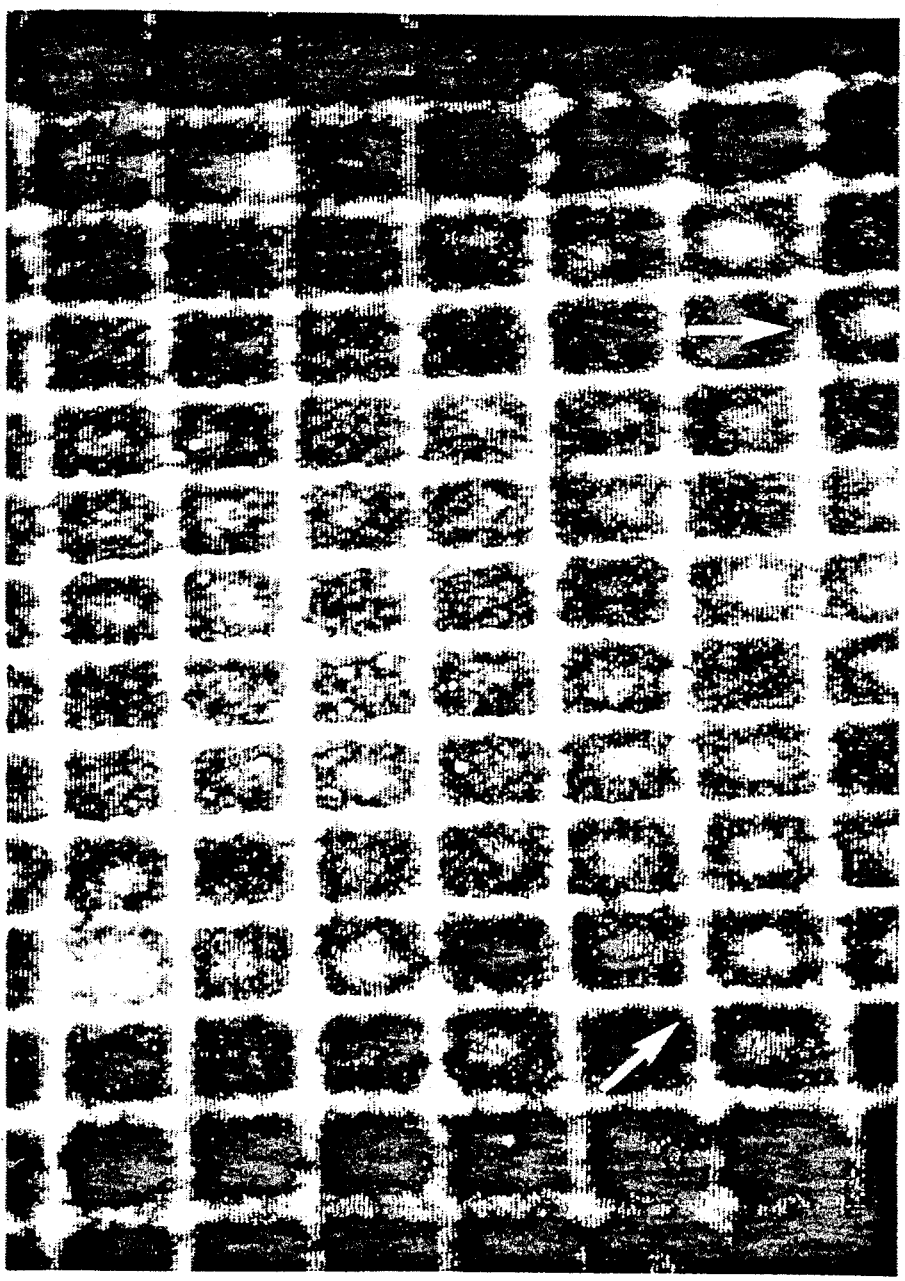
Figure 40:
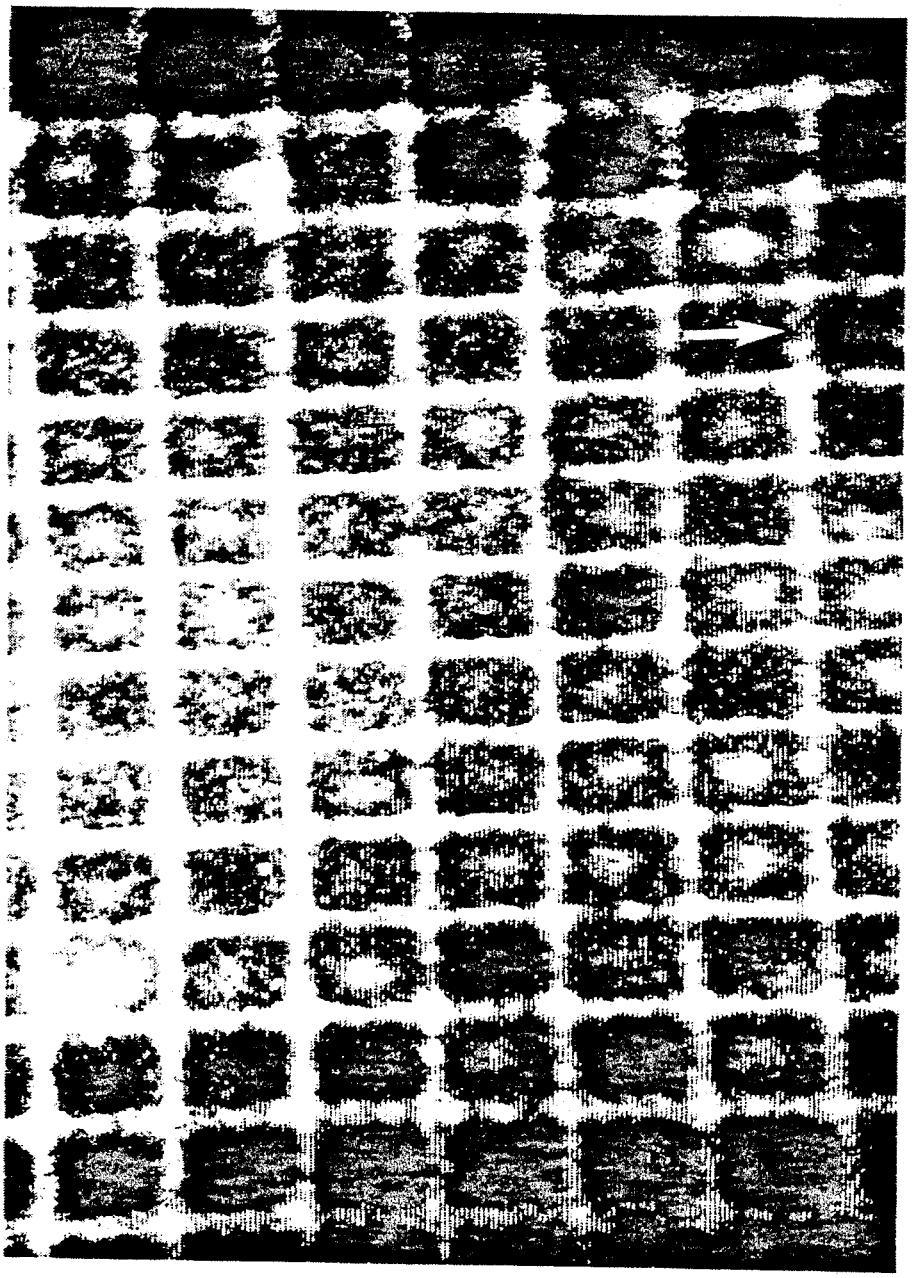
Figure 41:
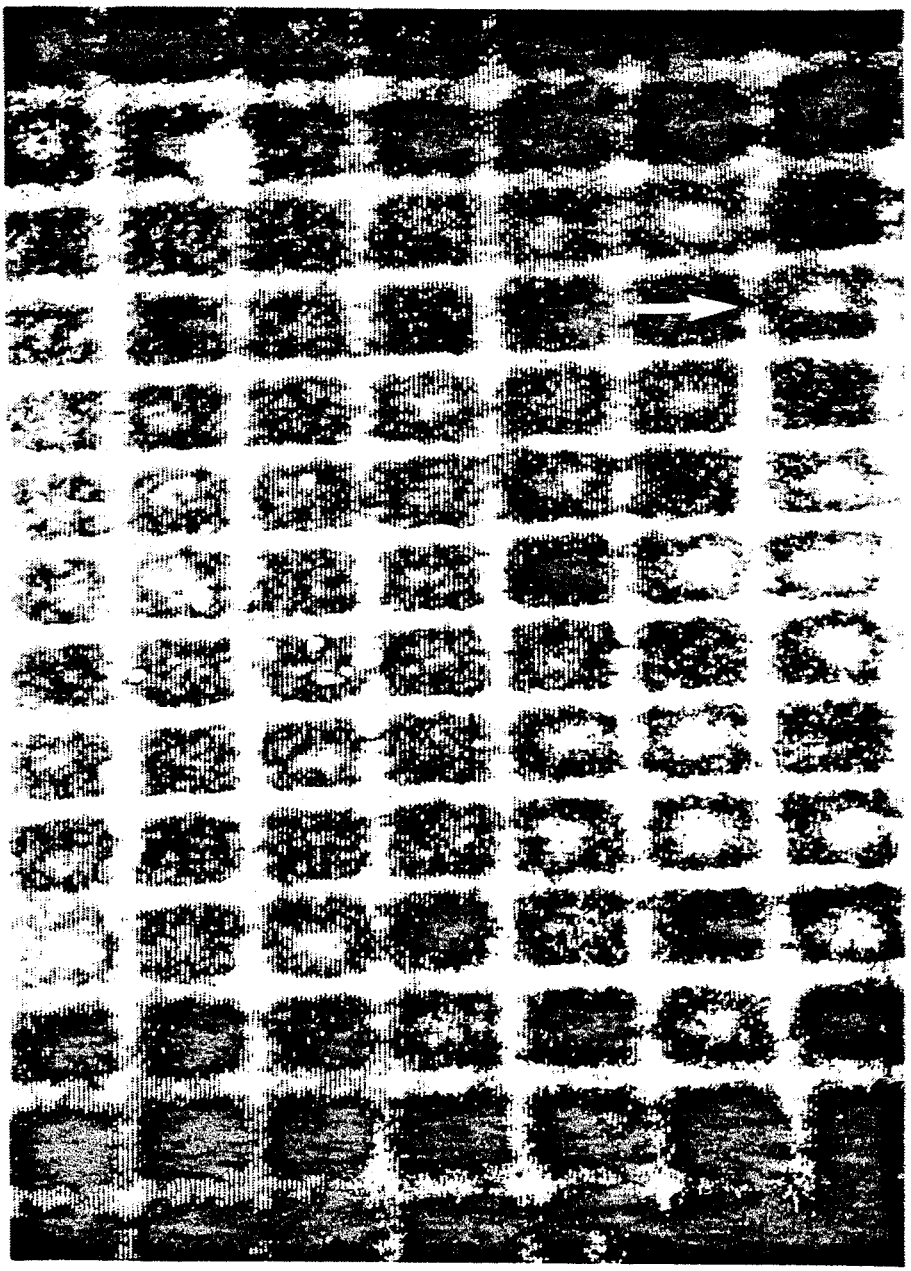

FIGS. 37–41 are a sequence of still photographs of a videotape showing that the cells are not permanently bound to the carrier but can be moved out of their apertures by the application of suitable forces. An ejecting force on the cells was created by squeezing tube 160 leading from orifice 150 to pump 162. Movement of the cells can be seen most clearly in FIGS. 37–41 by looking at the apertures marked by arrows. For the marked aperture in the lower left hand portions of the figures, the cell can be seen in its aperture in FIG. 37, out of its aperture in FIG. 38, and back in its aperture in FIG. 39, while for the aperture in the lower right hand corner, FIG. 39 shows the cell in, FIG. 40 out, and FIG. 41 back in the aperture. Although not clearly shown on these still photographs, the videotape revealed numerous smaller movements of the great majority of the cells on the carrier. As discussed below, the ability to remove cells from the carrier is of value once a particular population or sub-population has been identified.

Figure 42:
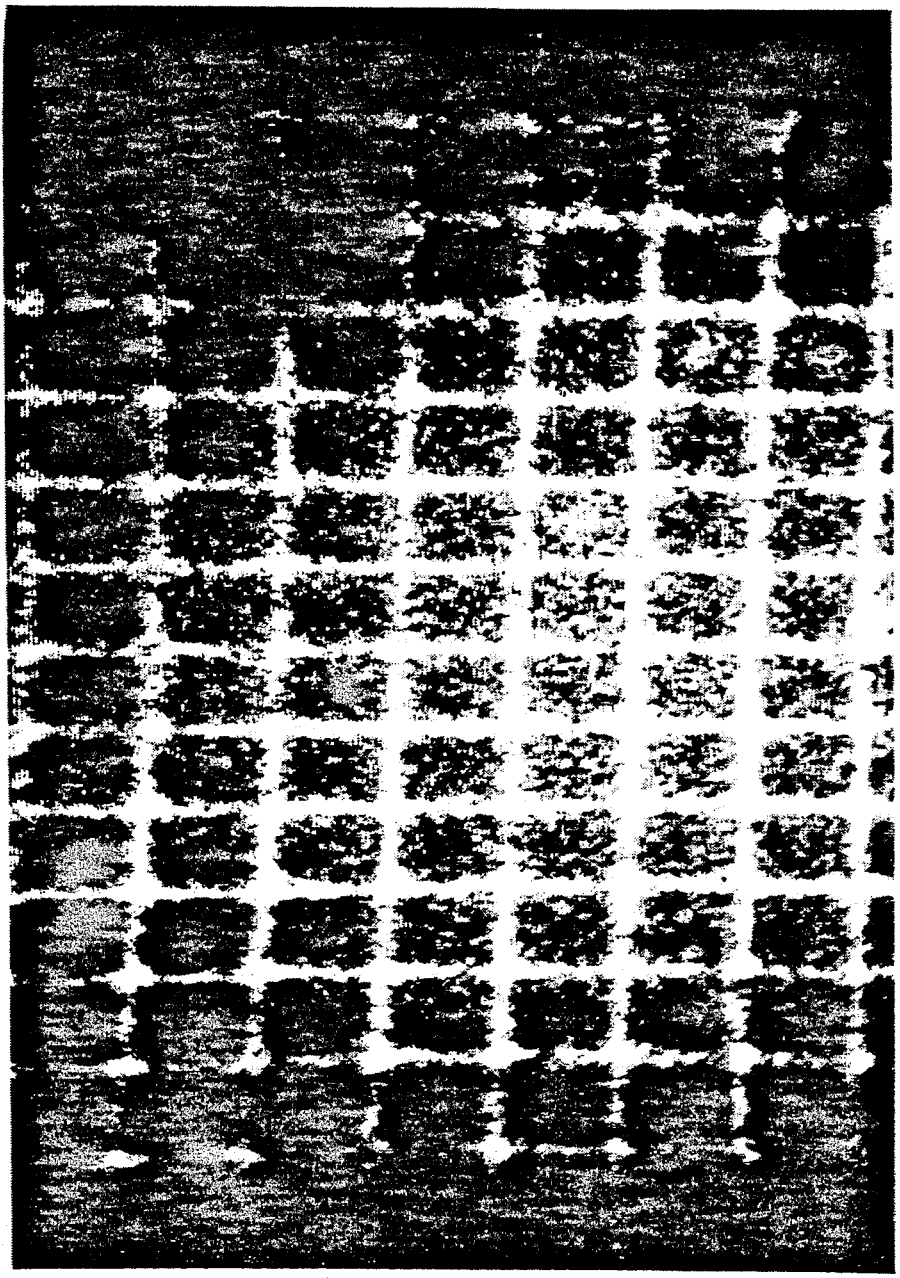
Figure 43:
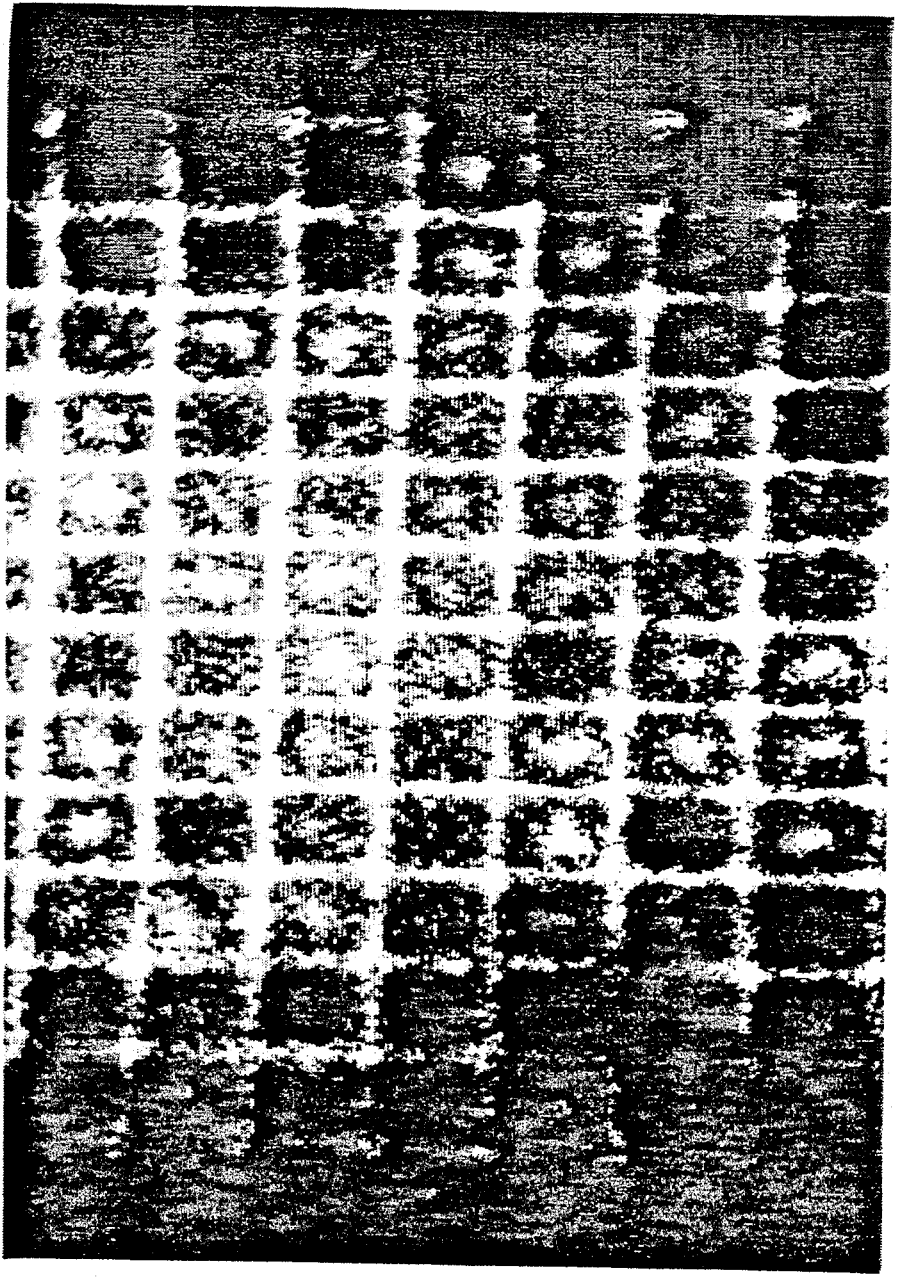
Figure 44:
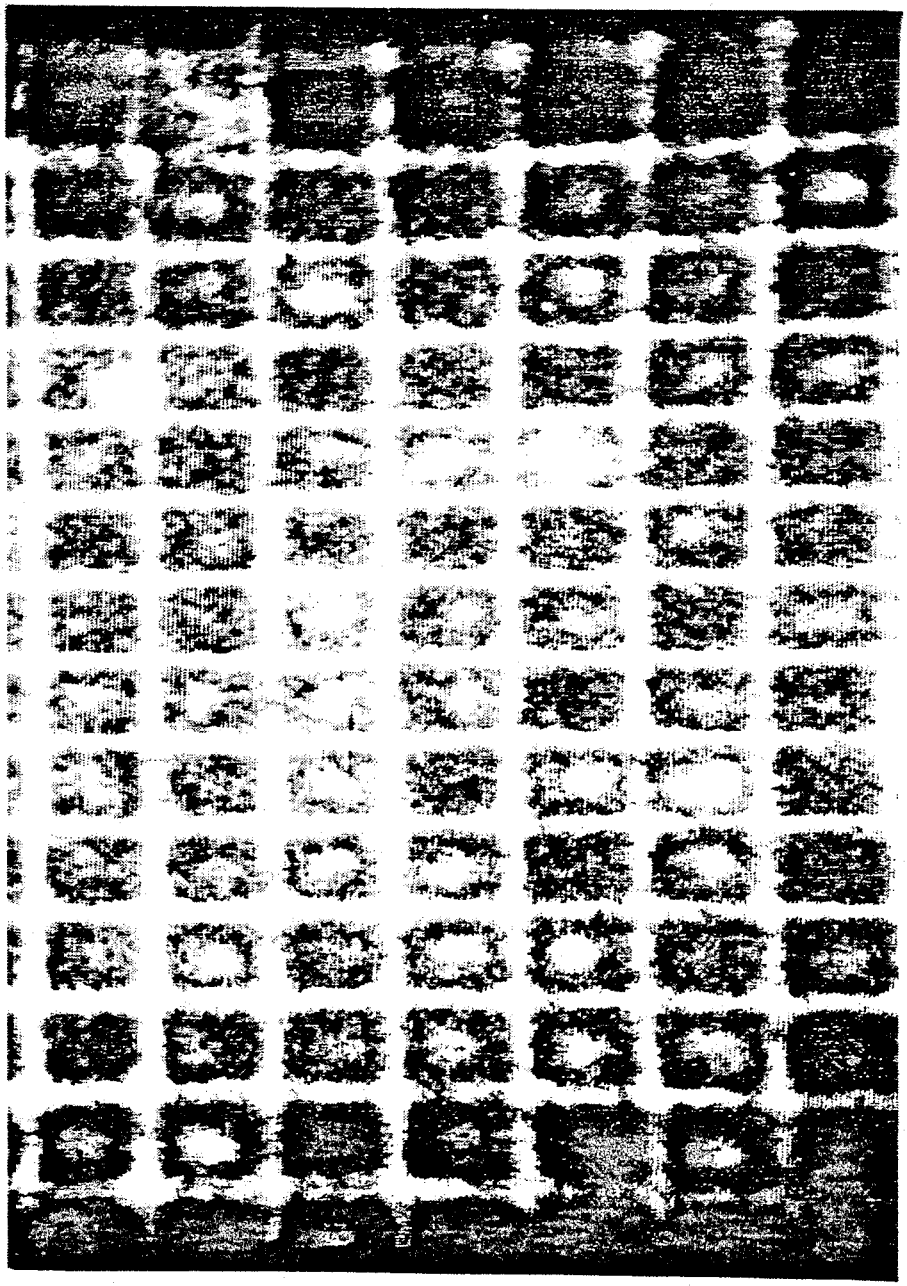

FIGS. 42–46 are a sequence of still photographs of a videotape demonstrating that substances can be applied (FIGS. 42–44) and removed (FIGS. 45–46) from cells held in the carrier by changing the bathing fluid by means of inflow tube 164 in FIG. 23. In FIG. 42, the cells were placed in the carrier in a suspension which did not contain FDA. As a result, the cells did not fluoresce and thus are essentially not visible in FIG. 42. A bathing solution containing FDA at a concentration of approximately 2.5 $\mu$M was then applied to the carrier through inflow tube 164. In a period of approximately 1–3 minutes, the cells absorbed the FDA and began to fluoresce. FIG. 43 shows the cells shortly after the addition of FDA, while FIG. 44 shows the same cells after a few minutes of exposure to FDA. In contrast to FIG. 42, the cells can now be clearly seen because of their high level of fluorescence.

FIGS. 45–46 show the reverse process. In this case, the cells were applied to the carrier in a solution containing FDA, and then an FDA-free bathing solution was applied to the carrier through tube 164. In the presence of this FDA-free bathing solution, the fluorescence of the cells gradually decreased indicating that the fluorescein in the cells was diffusing into the bathing medium and was not being replaced by new FDA. This decrease in fluorescence can be seen in FIGS. 45 and 46, where FIG. 45 shows the original, highly visible cells and FIG. 46 shows the barely visible cells produced after a period of approximately 1–3 minutes in the FDA-free bathing solution.

As discussed above, and in further detail below, it is important to be able to bring and remove specific substances from the captured cells in order to be able to perform a variety of analyses, including the Cercek SCM test. The results shown in FIGS. 42–46 demonstrate that such application and removal of substances can be readily done in accordance with the present invention.

In the examples described above, a pressure difference across carrier 1 has been used to drive the cells into the carrier apertures and then retain the cells in the apertures. Other forces can also be used for these purposes.

For example, FIG. 47 shows the use of an electric field to drive the cells against the carrier and into the apertures. The field is oriented perpendicular to the top surface of the carrier. As is known in the art, biological cells, including lymphocytes, normally carry a net electrical charge or, by adjusting the pH or other parameters, can be made to have a net charge. The electric field shown in FIG. 47 will accordingly cause cells, e.g., positively charged cells, to move towards the carrier and into the apertures, as desired. Of course, if it is negatively charged cells which one wants to capture on the carrier, one only needs to reverse the direction of the electric field.

The use of an electric field as the driving force can lead to electrolysis problems with uncoated metallic carriers. One solution to this problem is to coat the carrier with a non-conductor, as described above. Another solution, illustrated in FIG. 47, is to give the carrier a shape which localizes most of the electrolysis effects at points distant from the apertures where the cells are captured. In particular, in FIG. 47, the carrier is provided with ears or projections 172 which concentrate the electric field and thus the ionic current and electrolysis effects in regions away from the main body of the carrier. Such ears will also attract cells, but in general there will be an abundant excess of cells so that even if there is some concentration of cells in the regions of the ears, there will still be enough cells near the body of the carrier to fill the apertures.

As an alternative to using an electric field oriented perpendicular to the surface of the carrier, crossed electric and magnetic fields parallel to the surface of the carrier can be used to drive the cells into the apertures. As shown in FIG. 48, in this case, the electric field causes the charged cells to move across the top of the carrier, while the magnetic field produces a $v \times B$ force towards the surface of the carrier for positively charged cells. Again, negatively charged cells can be selected by reversing the direction of the B field. The use of a B field to drive the cells into the apertures has the advantage that once the cell comes to rest in the aperture, the force on the cell due to the driving force ceases because v is now equal to zero. In contrast, a pressure differential driving force continues to exert a force on the cells even after they have been captured in apertures, although in general this force is too small to cause damage to the cells.

In addition to using E and B fields to apply cells to the carrier, these fields can be used to enhance the rate of fluid exchange around individual cells and to select specific cells captured on the carrier based on such parameters as the cell's charge to mass ratio.

Figure 50:
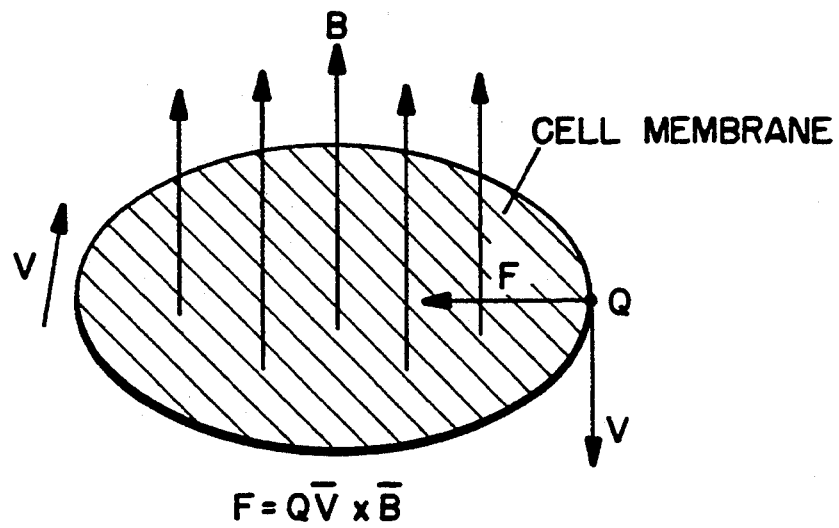
FIGS. 49–50 show the use of a time varying magnetic field to enhance fluid exchange about cells captured in a carrier.
Figure 49:
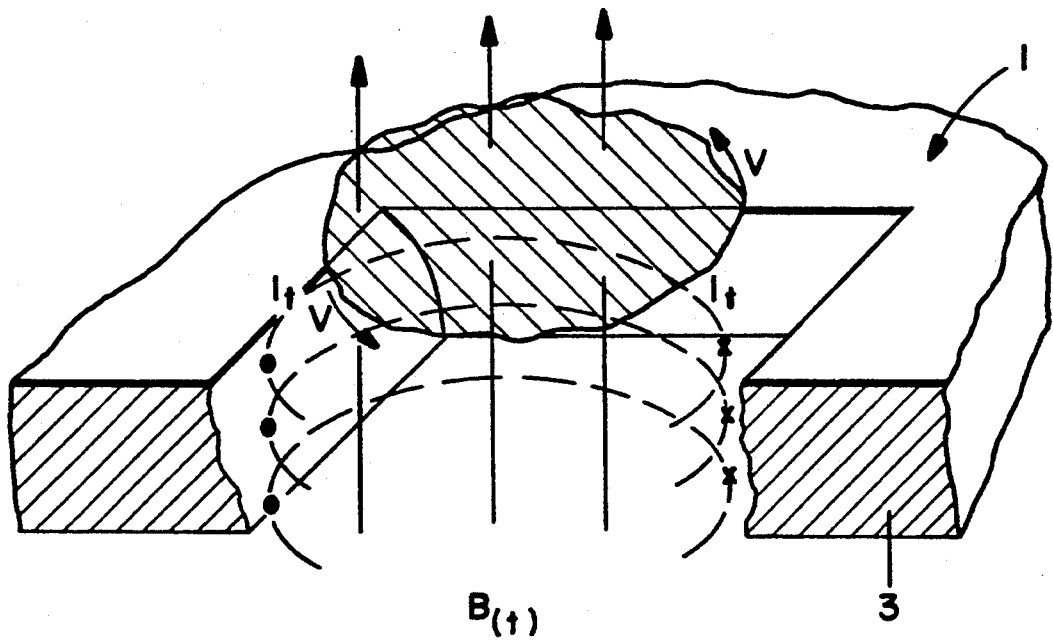

With regard to fluid exchange, FIG. 49 shows the use of a time varying magnetic field normal to the surface of the carrier to cause cells to rotate about their axes inside apertures. More specifically, the time varying magnetic field generates a circular or tangential electric field parallel to the plane of the carrier. The magnitude and direction of such a field is described by Maxwell-Faraday law, also known as Lenz's law. This field acts on the fixed charges on the surface of the cell membrane and thus causes the cells to rotate about an axis parallel to the magnetic field. It should be noted that once the cells begin to rotate their cell membrane will experience either an inward or outward squeezing force resulting from the $v \times B$ (Lorentz) interaction between the charges on the membrane and the applied B field (see FIG. 50). Whether the force is inward or outward will depend on the sign of the cell's surface charge and the orientation of the B field. In essence, the time varying magnetic field, in addition to rotating the cells, will also have a massaging effect on them. Furthermore, there will be a tendency for the rotating cell, which in effect is a magnetic depole, to move parallel to the magnetic field. In addition to the effects on the cells, the field also interacts with the charged ions in the bathing medium causing them to move in circular paths.

With regard to selecting particular types of cells from among the population captured on the carrier, FIG. 51 shows an arrangement for selecting those cells having a particular charge to mass ratio. As shown in that figure, a time varying, e.g., sinusoidal, electric field is applied across the carrier and a constant magnetic field is applied parallel to the top surface of the carrier. The response of individual cells to the electric field will depend on the frequency of the field and the cell's charge to mass ratio. Accordingly, by varying the frequency of the electric field, specific subgroups of cells can be made to move sufficiently far out of their apertures so that the force due to the magnetic field acting on the moving cell will cause it to move in the plane of the surface of the carrier. By means of surface washing during this process, these selected cells can be removed.

In addition to the foregoing, electric fields can be used to select individual cells. As discussed above, carrier 1 can include embedded conductors 101 (see FIG. 17). By varying the potential of these conductors, individual apertures can be given a potential which will tend to eject a cell captured in the aperture because the charge on the cell has the same sign as the aperture's potential. The potentials of neighboring apertures can be adjusted using others of the conductors to a value below the value which will result in cell ejection. Along these same lines, individual cells can be removed from the carrier by a local electric field created by bringing a charged probe into the vicinity of a particular cell's aperture. Groups of cells can be similarly removed from the carrier and moved to a desired location by using a movable array of probes, where selected probes in the array can be charged to a value sufficient to attract and move a cell from its aperture.

Once the carrier is filled with cells, either by a pressure differential, or by the magnetic or electrical forces described above, or by some other force, e.g., a chemically based force, each carrier with its group of cells of interest, e.g., with lymphocytes, is placed in a carrier holder of a flow chamber such as holder 10 (FIG. 2D)

to provide the necessary environment for the testing or measuring cycles, which will be described later.

In a first embodiment shown in FIGS. 2A-2D, 3A and 3B a plurality of matrices or cell carriers 1 are placed on holder 10 (FIGS. 2D and 3A). Only one orientation of the carriers is possible so that the perforations (holes) of the carriers are aligned relative to defined axes, such as X and Y (see FIG. 1A). The holder 10, which is the top of the flow chamber, is removably mounted upon a central part 11 (FIG. 2A) of the flow chamber. The central part 11 defines a plurality of channels 12, each being connected at both ends to one of a plurality of tubes 13 for supplying and discharging a desired solution. The central part is fixed at its bottom by a lower part 14 (FIG. 2B) of the flow chamber comprising a transparent wall 15 which is necessary when using incident and transmitted light techniques for analyzing the cells on the carrier.

As can be seen from FIG. 3A, which is a view on a section perpendicular to the direction of a channel 12 (the solution therefore flowing "into the page"), a flow director 16 ensures that the solution contacts the cell carrier 1. In FIG. 3B a side view of this arrangement is illustrated schematically.

On the holder 10 the carriers 1 of several different individuals (patients) are placed in one row extending along the channels, while a column of carriers of the same person extend perpendicular to the channels. Each channel 12 is related to one type of test so that the number of tests to be run determines the number of channels 12 in the flow chamber.

Any solution, which flows through any one of the channels therefore wets all the cells in the carriers above that channel, each belonging to another patient. The cell carriers 1 may be covered by a glass plate 17 to make possible the use of immersion liquid for the optical scanning system, if necessary.

In FIG. 2A the flow chamber is shown comprising seven channels 12. In such a case cells from each patient are carried on seven carriers, one per channel, while along each channel are supported carriers with cells of different patients, as shown in FIG. 2D. Such an arrangement enables one to stimulate cells of different patients to different stimuli via each channel either simultaneously or successively and then test or analyze the response of each cell to the particular stimulus. Other embodiments to be described also comprise of a plurality of channels. Thus in each multi-channel embodiment the number of cell carrying carriers from each patient is typically equal to the number of channels. However, as will become apparent from the following description the invention is not limited to multichannel arrangements. It was found that cells after being stimulated by certain stimuli and examined can be cleansed and thus returned to their pre-stimulated state to be stimulated subsequently by a different stimulant. Consequently if desired only one cell-supporting carrier per patient can be used. The cells thereon can be successively stimulated and after each stimulation and analysis be rinsed for the next stimulation and analysis.

Now, before describing other embodiments of flow chambers, it is considered desirable to describe particulars of one preferred method and system for individually analyzing the cells placed at defined locations on said carrier and introduced into said flow chamber. To this end reference is made again to the SCM-test as described by L. and B. Cercek et al. in the mentioned publications. According to L. and B. Cercek there are at least two characteristic properties of a subgroup of lymphocytes which are suitable for the SCM test. Acknowledgement of the specific antigen causes a lymphocyte to pass from a rest to a stimulated stage. When fluorescein molecules are imbedded in the lymphocytes, by utilizing a well known phenomenon, called fluorochromasia, the transition from the rest phase to the stimulated phase results in critical changes in the polarization of the fluorescence of the fluorescein in said lymphocytes. The lymphocytes, in which stimulation procedures may evoke such critical changes, differ in at least two characteristic properties from the other lymphocytes; the specific density, and the fact that for these cells a relatively high (control) value, e.g., 0.20, of fluorescence polarization is observed only for a very narrow band of emission spectrum around 510 nm.

This second property is taken advantage of to mark out, or identify the proper lymphocytes among the whole population of lymphocytes and thus avoid the necessity of their physical separation. It is thus the group of lymphocytes which exhibits this particular spectral behaviour on which then all further stimulation effects are examined, while all other lymphocytes will henceforth be neglected by the evaluation technique of the system. Alternately stated, in accordance with the invention, first the carrier is used to separate lymphocytes in a person's drop of blood from other types of cells by means of the sizes of holes in the carrier. The holes are filled substantially by lymphocytes, one cell per hole. Smaller cells passing through the holes and larger cells are washed off the carrier's top surface. Thereafter the lymphocytes on the carrier are rinsed with FDA+PBS, which by fluorochromasia is converted within the cells to fluorescein. Then the fluorescence polarization within a narrow hand of the emission spectrum around 510 nm from each cell, is measured and recorded. Only those lymphocyte cells, each of which exhibits a relatively high value of fluorescence polarization, defineable as P are regarded as belonging to the particular subgroup of interest. Since the address of each cell on the carrier hole array is known the address of each cell in the subgroup is known. Thus one the cells belonging to the subgroup are known, all subsequent measurements and/or observations which may be performed, are performed only on the cells in the subgroup, whereas all the other lymphocyte cells on the carrier which do not belong to the subgroup may be ignored in that neither measurements nor observations are performed on any of them. The limiting of subsequent measurements or observations to only the cells in the subgroup greatly reduces analysis time which is of great significance. Furthermore and possible more important, since the address of each cell is known, the cell's unique response to each stimulant can be recorded to provide unique information, heretofore unattainable due to the fact that measurements and observations were performed on batches of cells or those employing flow systems. Also even when observing a particular cell under a microscope one could not thereafter stimulate it with another stimulant and observe the cell's response thereto. This is due to the fact that heretofore individual cells were not placed in a fixed array with the address of each cell known, so that the measurement and/or observation instrumentation could be directed repeatedly to the same address to observe the same cell.

A suitable criterion may be determined, of the minimum ratio of polarizations measured at two fluorescence emission wavelengths, namely 510 nm and at 515 nm. Therefore, as a first step, the cells of the critical subgroup of lymphocytes are identified by testing said criterion for every single cell on the carrier. Upon transition to a state of stimulation the degree of polarization of the stimulated members of said subgroup decreases to a value of about 0.14 for said emission wavelength of 510 nm. This change of the degree of polarization is examined only for the identified cells of said subgroup.

A system for carrying out these tests for each cell on the carrier will now be described in connection with FIG. 4. The cells on carrier 1 are first typically rinsed with a solution of phosphate-buffered saline (PBS) and fluorescein diacetate (FDA). The latter due to the phenomenon of fluorochromasia is converted within each lymphocyte cell to fluorescein. Then the fluorescein is excited by radiation of wavelength 470 nm upon which it emits its characteristic emission spectrum. The determination of which of the lymphocyte cells on the carrier belong to the subgroup of interest is made by stepwisely scanning each and every cell on the carrier by means of the optical analyzer 20, shown in FIG. 4.

It includes a zirconium lamp (or laser) 21 which serves as a light source peaking at 470.1 nm and 468 nm, thus eliminating the need for an excitation filter to filter any light in the range of interest, i.e. 510 nm and 515 nm. The light is plane polarized perpendicular to the plane of FIG. 4 by a polarizer 22, after passing a focusing lens 21a. The plane polarization is represented by the small circles. The plane polarized light beam strikes a mirror 23 which acts as a beam splitter in that it transmits light of $\lambda > 500$ nm and reflects light below such wavelength. Thus the light from source 21 is reflected to the carrier 1, through a lens 24.

The fluorescence emitted by each cell on the carrier is separately measured and recorded. The fluorescence from a cell passes through mirror 23 and lens 24a to a Glenn-Thompson polarizer 25. Basically, polarizer 25 divides the fluorescence into two parts: One polarized parallel to the plane of the paper (indicated by the dashes in FIG. 4) which proceeds at the original direction of incidence, and the other polarized normally to the plane of the paper (indicated by the circles in FIG. 4) which is deflected normally to the direction of incidence. Each of the polarized beams is divided into two equal and perpendicular beams by a beam splitter (26, 27). Each of these four newly formed beams passes through an interference filter of 510 nm or 515 nm (28, 29, 28', 29', respectively) and their intensities are measured simultaneously by four photo multiplier tubes (30, 31).

Figure 16:
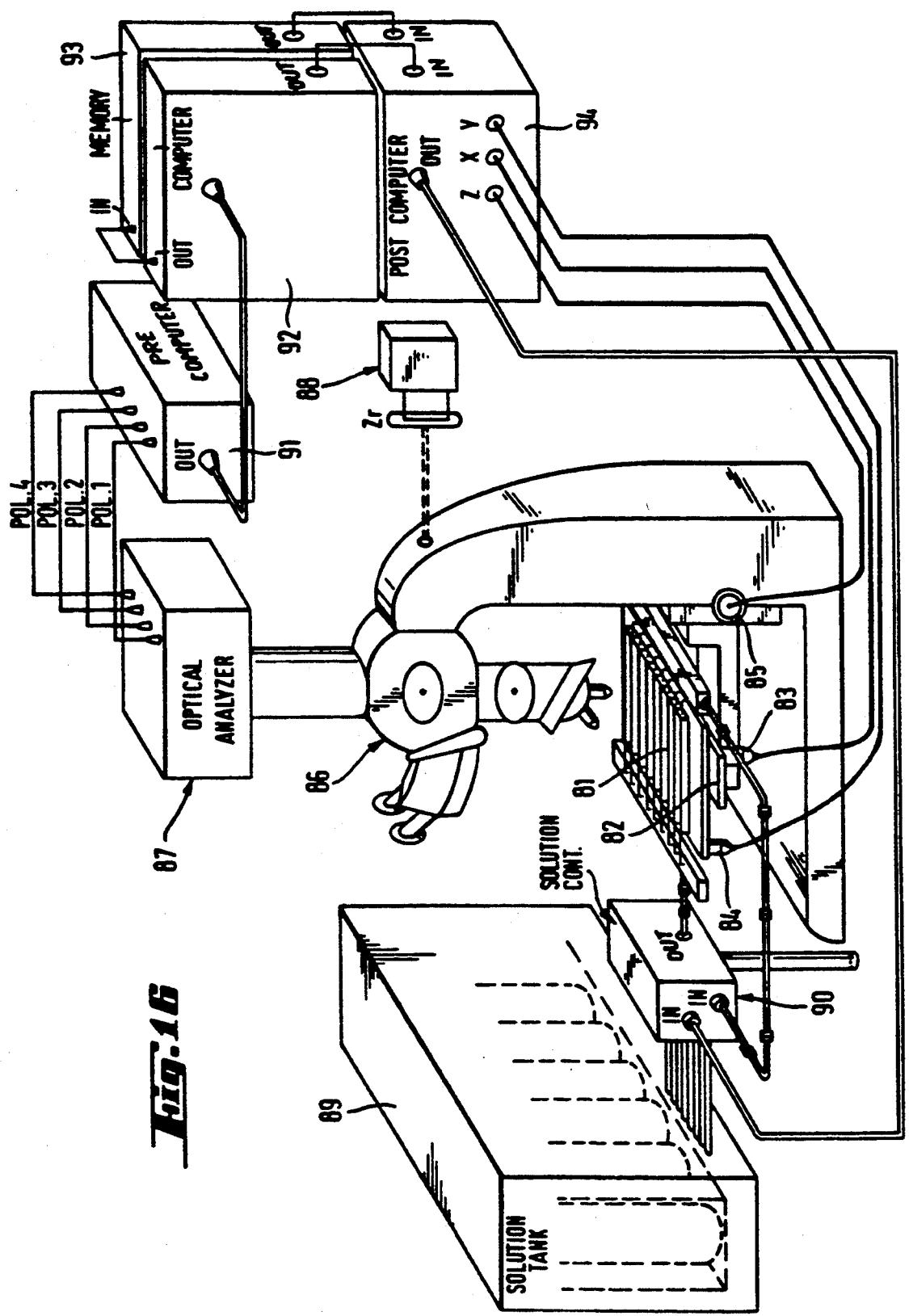
FIG. 16 is an overall schematic representation of an optical diagnosis system using the present cell carriers.

These four measured intensities are stored in a computer system such as that shown in FIG. 16, and the degree of polarization for each wavelength, i.e. $\lambda = 510$ nm and $\lambda = 515$ nm is calculated. The degree of polarization is defined as $$P = (I_{11} - I_1)/(I_{11} + I_1)$$

After calculation of $P_{510}$ and $P_{515}$ their ratio, i.e., $P_{510}/P_{515}$ representing the control value is calculated in real time. The address of each cell in terms of its X and Y coordinates is known and is stored together with its control value. After all the cells have been examined and their control values determined and stored it is very simple to determine the cells having a control value of not less than 1.3. It is these cells that belong to the subgroup of interest. Once this determination is made all subsequent measurements or observations of the response of the cells to various stimulating agents are performed on the cells in the subgroup only and all other cells are ignored. For example, only the cells in the subgroup are re-examined to determine which of them exhibit a change in the degree of polarization sufficient to identify them as active and thus capable of identifying a particular antigen.

It should be apparent that to test each cell individually the optical analyzer 20 (FIG. 4) has to have an optical resolution in the range of one cell diameter which is achievable with a microscope objective. The carrier with the cells is stepwise displaced under the microscope from one perforation to the neighboring one, e.g., through the use of stepping motors having displacements in the micron range (see FIG. 16).

Figure 52:
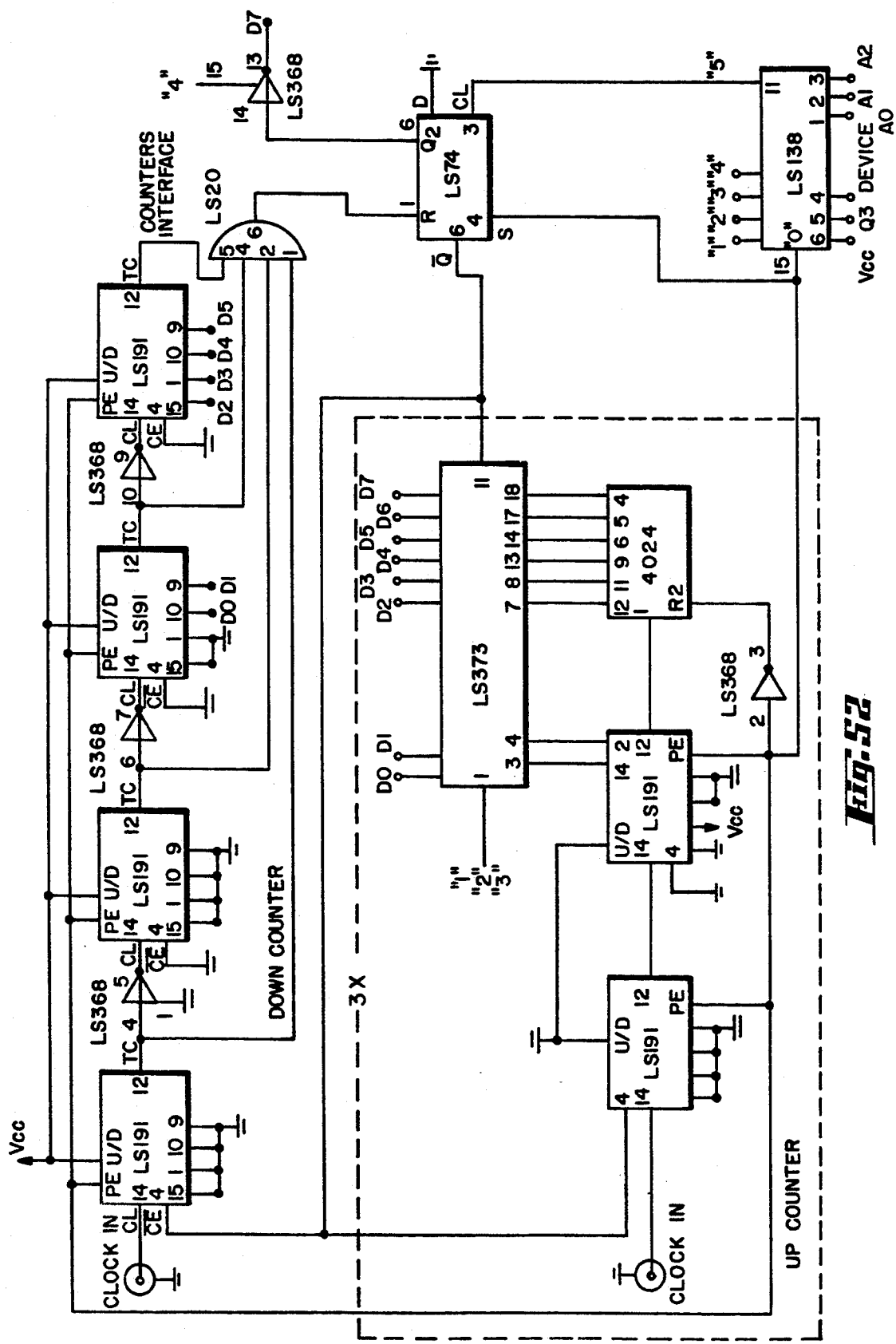
FIG. 52 illustrates a circuit for receiving and processing input data from the photomultiplier tubes of FIG. 4.
Figure 53:
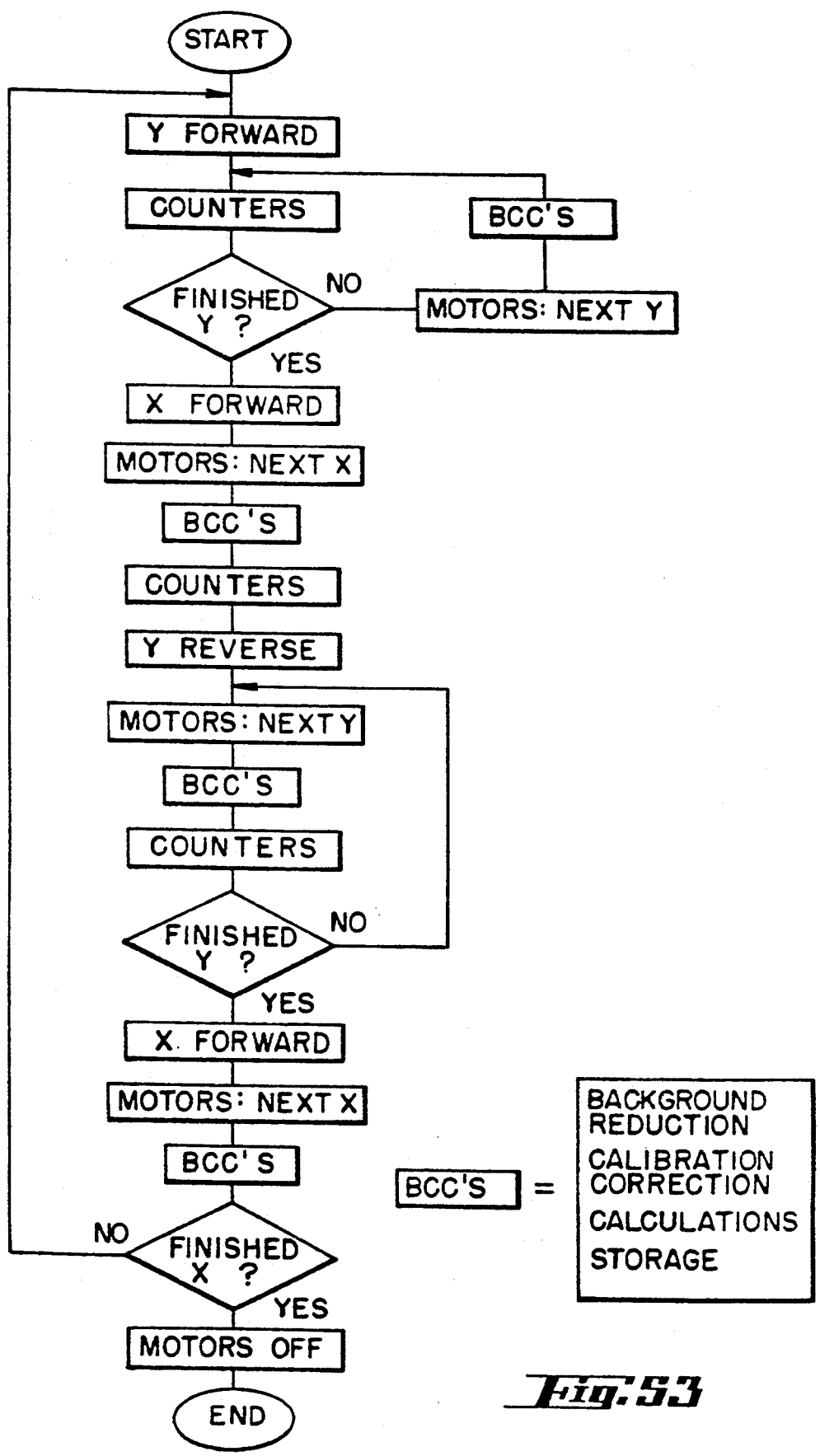
FIG. 53 illustrates a flow diagram of a routine for scanning a carrier to identify cells having fluorescence polarization control values within a desired range.

A microfiche appendix of a computer program listing is included in U.S. Pat. No. 4,729,949 from which this application claims priority. That computer program can be used with the apparatus of FIG. 4 to identify lymphocytes having polarization control values within the desired range of above 1.3. The program is designed to run on an Apple II or similar computer to which has been added a card having the components shown in FIG. 52 for receiving and processing input data from the photomultiplier tubes and a second card of standard design for handling parallel input/output. A flow diagram of the scanning approach employed in this program is shown in FIG. 53. As shown in this diagram, at each carrier location the output of the photomultiplier tubes is recorded on a group of counters and these values are then subjected to background (B) and optical calibration (C) adjustments, after which the polarization control value is calculated (C) and then stored (S). The background procedure involves submerging the carrier in water and measuring the amount of light reaching each of the four photomultipliers, i.e., the dark current of the photomultipliers. The calibration procedure involves adding fluorscein to the water and determining the degree of polarization of the emitted light at 510 nm and 515 nm. Theoretically, the degree of polarization for water should be zero, so that any deviation from zero is used to correct the measured values obtained from the cells. To minimize movement of the carrier during scanning, the program is designed to scan succeeding carrier rows in opposite directions, that is, the first row (y=o to n) is scanned from left to right, the second row (y=n to o) is scanned right to left, and so forth.

Figure 5:
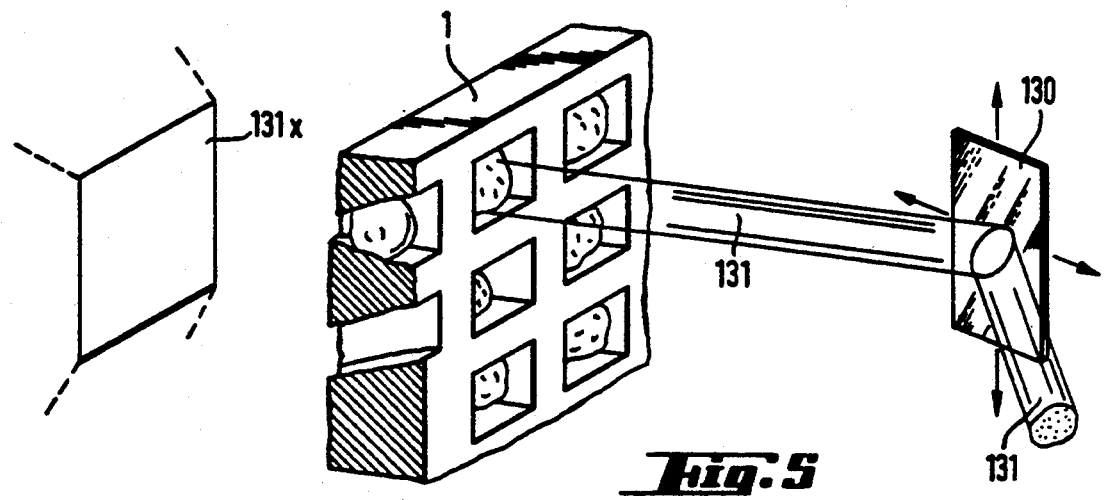
FIG. 5 shows schematically a second embodiment of an optical analyzer.

In another embodiment of the optical analyzer, the need to stepwise displace the cell carrier is avoided by using a laser as the excitation light source. In FIG. 5 this embodiment is schematically illustrated. A laser beam 131 of appropriate wavelength passes through a controlled deflecting optical element such as, e.g., a rotating mirror 130. The laser beam 131 has a cross-section which corresponds substantially to the size of a cell. By means of the deflecting element 130, the beam 131 scans the cells in the holes sequentially, thereby exciting each cell, one after the other. At any given time only one cell is hit by the laser beam and therefore only this cell emits fluorescence light at that moment. The optical analyzer 131X, disposed on the other side of the carrier 1 has a visual field, covering the whole surface of the carrier 1. At the moment of the receipt of an emission signal, the intensity of this signal is correlated with the position of the scanning laser beam 131, hence each received and analyzed light signal is correlated with the position of the respective cell from which it has been emitted. As can be seen from FIG. 5 the excitation is made from the large side of the holes 2 in the carrier 1. For the optical analysis, on the other hand, emission light leaving each hole through the narrow end is preferably used for reasons which will be explained below.

Having explained preferred analyzing systems using the invention, it should be well understood that analogous systems for measuring other parameters may be used, provided that focusing on each single cell on the carrier is possible. Examples of measurable parameters include light intensity, optical density, index of refraction, electromagnetic properties, absorption and scattering. Furthermore, the scanning procedure is not limited to beams such as visible light, U.V., I.R. and electron optical systems, but may also include probing via physical contact at each cell. Other examples of measurable or observable properties include nuclear magnetic resonance (NMR), pH value as well as cell morphology and changes thereof in response to different stimulants. For example, one can direct the output of a microscope pointed at any cell to a pattern recorder to produce a two-dimensional record of the cell's pattern. Cell temperature measurements and/or temperature changes may be performed and recorded. In summary, any one or more measureable or observable property of a cell may be performed on a cell by cell basis. Since the address of each cell is known one can always return to the same cell for additional measurements and/or observations. All measurements and observations for each cell can be recorded to obtain unique information for each individual cell. This information can be correlated to provide insight and diagnosis, heretofore unattainable.

An embodiment of the invention for practical clinical use will now be explained in connection with FIGS. 6A-6C which show a modified holder 40 for a plurality of cell carriers 1. The holder 40 is wave-formed to enable its troughs 41 to be immersed in the solutions flowing through the channels 12 at a higher level. The cell carriers which are mounted on the bottom of the troughs 41, can be wetted to rinse or otherwise stimulate the cells both from the upper and the bottom sides. Therefore, in this embodiment there is no need for flow directors, as previously explained in connection with FIGS. 2A, 3B. As has been described in connection with FIGS. 2A-2D, the cell carriers positioned on the same trough 41 belong to different patients. In spite of this there is no danger of any mixed lymphocyte stimulation effect because there is no physical connection between carriers. Even if a cell would disconnect from one carrier, the chances of it being rinsed out are much higher than that of it being deposited on another carrier. In FIG. 6A carriers are shown only in one trough. However, in practice for each patient a carrier is present in each trough.

In FIG. 6C the carrier 1 is shown as being removable from holder 40. However to define its hole array in X and Y, it includes ears 8 locatable in identations 9.

Since the cell carriers 1 of the present embodiment are immersed in the solution flowing through each channel 12, the microscope of the optical system for cell scanning is provided with a quartz sleeve 42 (FIG. 6B) dressed on its objective cylinder. The channels 12 and the troughs 41 have dimensions which enable the relative movements of the objective and the carriers necessary for scanning the whole surface of each of the carriers.

As indicated above, to select the subgroup of cells based on the above described control value the channels are first supplied with a PBS+FDA solution during the control measuring cycle for identifying the proper cells on each carrier belonging to the subgroup. Thereafter, for determining the reaction of the selected cells to different stimulating agents each channel is supplied by a different stimulating agent, e.g., phytohemagglutinin (PHA), EF, CaBP, tumor extracts, or any other desired mitogen or antigen. Then the responses of only the selected cells are examined and recorded.

For the above stimulators it was discovered that stimulation of cells by one stimulator, does not affect any following stimulation if the stimulator is rinsed to reset the cells before the next stimulation test, in order to prevent any direct interaction or any competitive effect between them. Furthermore, it has been found that bonding the cells to the carrier has no appreciable effect on their activities. As a consequence, the stimulation procedures can be repeated on the same cell at the same location on the carrier, and this with different activating agents. Thus, an exact profile of the response of each individual cell of the subgroup to activation can be received as a function of time and it is therefore now possible to know the exact number and response of the activated cells and their places on the matrix which remains the same during and after the above described measuring cycles.

Most of the carrier holder systems, described above, were designed for top scanning, i.e., for analyzing the emitted fluorescence light from the large upper side of the holes in the carrier, which allows the use of the same optical system for optical examination and analysis of the cells. In alternative embodiments, which will be described herebelow, the optical analyzer is placed to receive the emission light passing through the narrow side or bottom of the holes 2. Thus, disturbing effects, caused by light emission of fluorescein, which leaks out of the cells and is present in their surroundings can be eliminated. The light emitted by the surrounding fluorescein represents an undesired optical background. Looking at the cells from the narrow sides or bottoms of the holes permits the reduction of this background substantially, since the narrowing conus acts as a shield against undesired emission light. Moreover, in the case of the excitation light entering the holes through their large sides, or tops, reflections at the conical walls may occur, whereby incident light as well as fluorescence light is reflected back. Another advantageous effect, caused by carrying out the optical analysis in the mentioned way is that at every location on the carrier only the emission light of the cell trapped within the respective hole is received, whereas other cells which may in exceptional cases be present at the upper surface of the carrier do not significantly influence the measuring results. Still another advantage resides in the fact that due to the smaller size of the openings it is much easier in practice to analyze the emission light of each cell separately, without the danger of cross-talking between adjacent cells if the adjusting mechanism of the optical system relative to the holes is not of extreme precision.

Figure 7A:
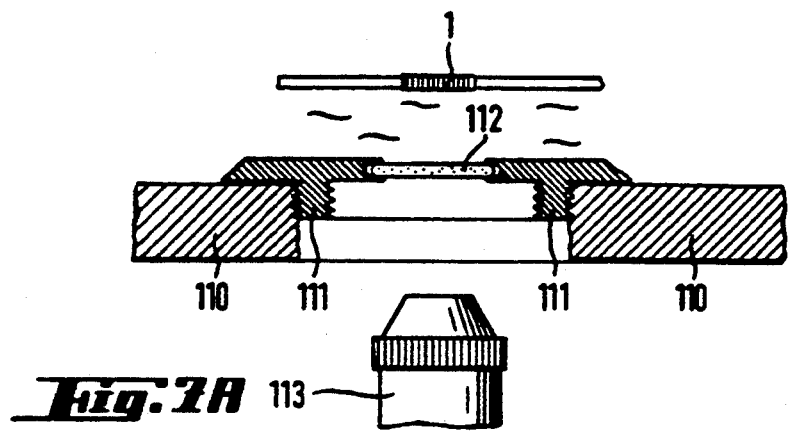
FIGS. 7A and 7B show an embodiment of a flow chamber for a bottom side analyzing system.
Figure 7B:
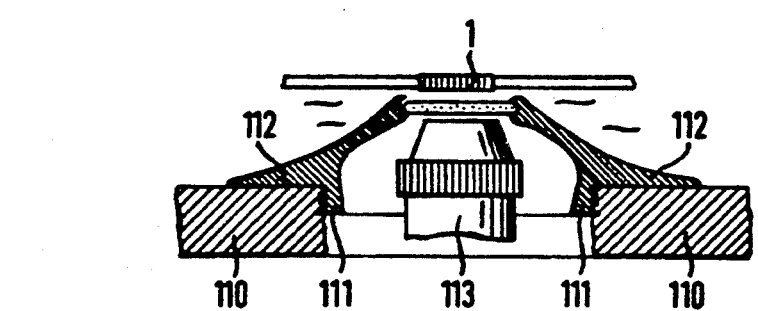

By means of the FIGS. 7A, 7B, 8 and 9, various embodiments are illustrated which enable the optical analysis to be carried out as explained above. In a first embodiment for use with a microscope optical analyzer (FIGS. 7A and 7B) the bottom wall 110 of the flow chamber comprises elastic (rubber) glass holders 111, each carrying a glass plate 112 adjusted relative to an above located cell carrier 1. The elastic glass holder 111 provides a fluid-tight seal between the glass plate 112 and the bottom wall 110 of the flow chamber and enables the objective 113 of a microscope to be moved close enough to the cell carrier 1 for scanning its individual locations or holes from below (FIG. 7B). If the objective 113 of the microscope is in its lower position, the channel of the flow chamber then is opened to its initial height. In a modification (FIG. 8) of this embodiment the bottom and side walls of the flow chamber are integrally made of rubber.

In a second embodiment (FIG. 9) the optical analysis is made from the upper side. However, the holder 114 for the cell carriers 1 is placed upside down on a bottom portion 115 of the flow chamber, after being provided with cells in a special unit (which will be described in connection with FIGS. 12A and 12B), such that the conical holes in the carriers 1 flare downwardly. In order to hold the cells in place and to effectively bond them to the carrier a pressure difference is applied between the bottom portion 115 (FIG. 9) and an upper portion 116 of the flow chamber, the fluid in the bottom portion 115 having a slightly higher pressure than in the upper portion 116. Sealing ledges 117 prevent the two portions of the flow chamber from leaking. Using this embodiment the optical analyzer of FIG. 4 can be used for scanning the cells on carriers 1 without giving up the above-described advantages.

Returning now to the problem of providing the cell carriers with cells of a certain desired population or group, which in principle could be done in substantially the conventional manner described above, FIGS. 6, 7A and 7B illustrate a system for simultaneously separating said cell population from other groups of cells other than by the conventional disadvantageous methods of cell separation. The present embodiment is also described with regard to the separation of lymphocytes from the other blood cells, for use in the above described SCM-tests.

Figure 10:
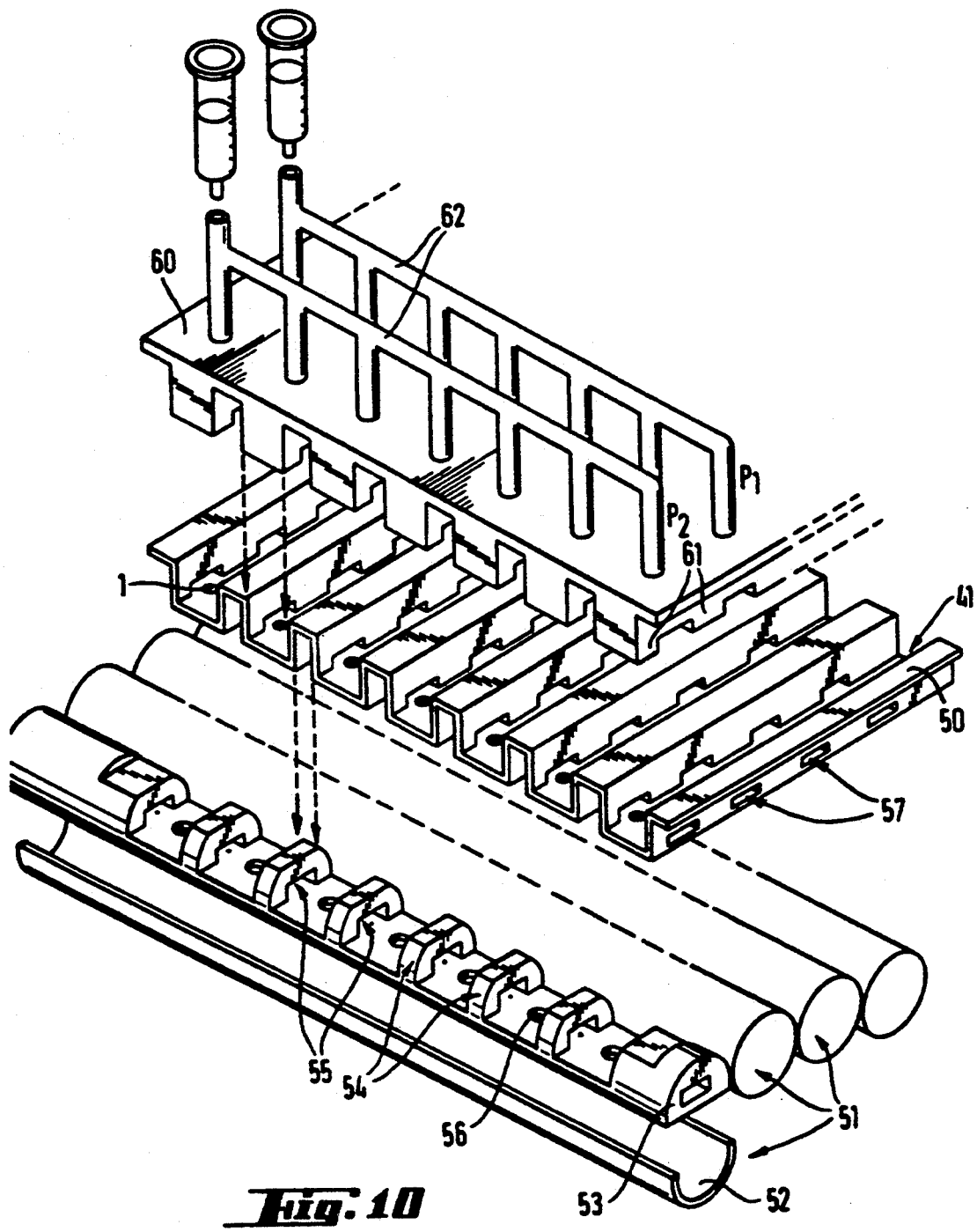
FIG. 10 shows a separation unit adapted to receive the holder of FIG. 6 for providing the cell carriers with cells.
Figure 11:
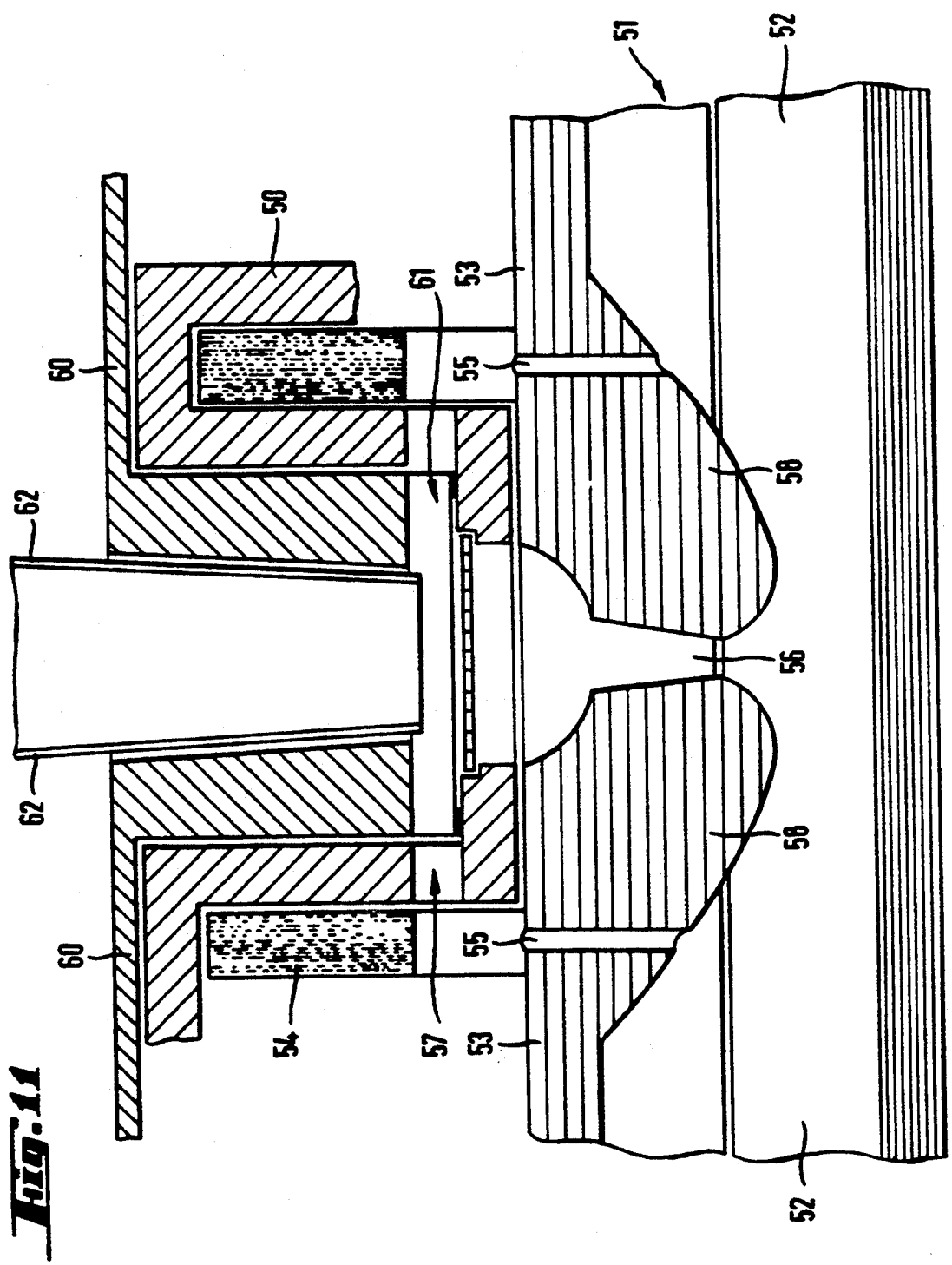
FIG. 11 shows a sectional view of parts of the embodiment illustrated in FIG. 10.

As can be seen from FIG. 10 and FIG. 11 the holder 50, which is insertable onto the flow chamber of FIG. 6A rests on an arrangement of pipes 51, each being subdivided lengthwise in an upper part 53 and a lower part 52. The lower part 52 forms a fluid (air or liquid) conduit of lower pressure to drain liquids and improper blood cells from the upper part 53. The upper part comprises bridges 54, under which there are drainage holes 55, and between which there are suction holes 56, aligned with the carriers 1 on the holder 50. In FIG. 10 carriers for supporting cells from only one patient are shown. The upper and the lower parts 53 and 52 are supplied by a fluid, say a PBS-solution. As becomes clear from the sectional view of FIG. 11, the fluid in the upper part passes under the bridges 54 and through appropriate slots 57 in the holder 50. The fluid in the lower part 52 is forced by projections 58 to flow with a higher speed in the region of the draining holes 55 and the suction holes 56, thereby creating a local subpressure in those holes. Therefore the fluid initially flowing through the upper part 53 is partly drawn to the lower part through said holes.

A blood supply element 60, removably placed upon the holder 50, is provided for supplying the carriers 1 with blood. Legs 61 of supply element 60 prevent fluid from passing from one row of slots 57 in the holder 50 to another.

As a theoretical basis for understanding the cell separation by the above unit, the following facts are emphasized:

a) the size of the responding lymphocytes is $7\mu$;
b) the size of macrophages, granulocytes is $20\mu$–$35\mu$;
c) the size of erythrocytes can reach $3\mu$–$5\mu$;
d) there are large lymphocytes-$15\mu$;
e) the size of the platelets-negligible;
f) cells can burst when left in distilled water;
g) the life span of an erythrocyte in distilled water is much less than that of a lymphocyte.

The cell carrier holder 50 is first placed on the pipe arrangement, such that the carriers of the first row (normal to the channels) are placed above the holes. The supply element 60 is placed with its legs 61 being on either side of the cell carriers. The whole system is assembled, as shown in FIG. 11. A syringe with full blood from a patient is placed in a syringe holder 62. In FIG. 10 two such holders are shown for two different patients. The blood flow in each of the pipes is controlled by applying suitable pressure on the syringe. Blood arrives at all the exits of pipes P1 and P2 (from 2 different patients) after the first few pressure pulses.

At a certain stage a pressure pulse will cause a drop of blood to fall on each cell carrier. The size of the holes in the carrier will not allow the blood to pass from one side of the cell carrier to the other. To this end a subpressure is formed in the lower half of the separation pipe, as described above, by running PBS through this part of the pipe. The blood is sucked immediately under the carrier.

The smaller cells will pass through the carrier and will be rinsed away with the PBS flow. Those with a size similar to that of the top of the holes of the carrier, e.g. $7$ $\mu$m, will stop on the carrier and the biggest will rest above the carrier. In order to prevent blocking of the carrier, the blood supply is stopped and PBS flows across the upper part of the matrix for washing away the bigger cells. Most of them are sucked into the drainage holes 55 (FIG. 11). The minority of the cells get to the next carrier (in the direction of the stream) and pass out. As previously pointed out, all cell carriers, placed perpendicularly to the extension of the channels are filled with the blood of one donor. Therefore there is no problem of blood being mixed from different donors.

In the next stage the upper flow is stopped and another drop of blood is dripped and the cycle is repeated as often as necessary. After a few drops of blood a so-called "upper bursting wash" is carried out. The process is continued until the carrier is sufficiently filled. A rough test of this can be made by testing the electrical resistivity of the carrier after each drop. Distilled water flows for any desired time and causes the erythrocytes to burst. The distilled water causes cells to swell, and therefore, the erythrocytes burst, while the lymphocytes strengthen their hold in the carrier holes. At the end of the desired time interval PBS is introduced. The substances set free from the bursted erythrocytes cannot influence the lymphocytes since there is a permanent flow of solution washing these substances away. Electrically charging or recharging the matrix, or applying or terminating electromagnetic fields is analogous to vibrating the matrix via ultrasonic or other techniques which can also be used. This procedure can be added and correlated with the stages of washing. Less than 1 cc. of blood will be necessary from each patient $P_1$, $P_2$, etc.

This separation process lasts about 5 minutes at the most. There is no limit to the number of blood samples from which cells can be simultaneously separated. The holder 50 is then removed from the separating system and inserted into the flow chamber of FIG. 4 for the optical scanning operation as described above.

Figure 13A:
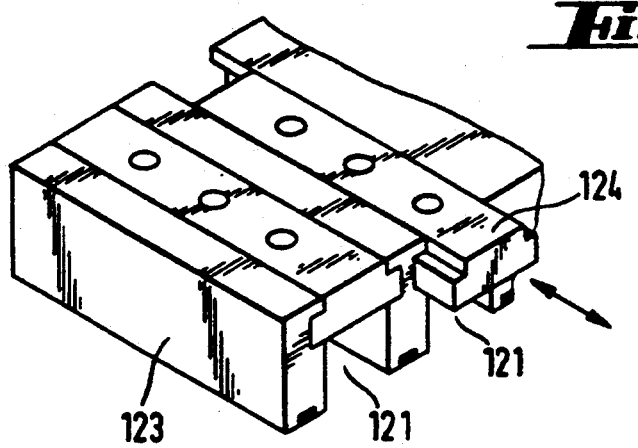
FIGS. 13A–13C show details of a blood supply element adapted for use with the separation unit of FIG. 12.
Figure 13B:
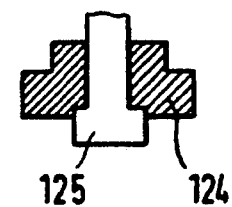
Figure 13C:
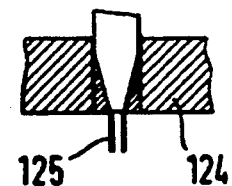

A similar separating system but adapted to the holder 114 of FIG. 9 will be explained by means of FIGS. 12A and 12B. A base plate 120 is provided with channels 121 for fluid flow, causing the necessary local subpressure in the region beneath the carriers 1 and draining holes 55. To this end projections 122 are formed on the base of the channels 121. The holder 114 is removably placed on the base plate 120 so that its carriers 1 are aligned with the projections 122 as can be seen from FIG. 12B, such that their conical holes open upwardly, i.e. towards an overlying removable supply element 123 which is similar in function to the supply element 60 of FIG. 10. The supply element 123 may supply the cell carriers with cells merely by the action of pressure as has been explained in connection with FIG. 10. It is, however, possible to enhance the efficiency of blood supply by providing smearing elements which are displaceable with respect to the carriers, as illustrated in the FIGS. 13A, 13B, 13C and 14. In FIGS. 13A, 13B and 13C an embodiment is shown, having slide plates 124 extending in the supply element 123 aligned with the channels 121.

At each outlet of a supply conduit a resilient smearing element 125 is arranged as can be seen from FIGS. 13B and 13C. In FIG. 13B a cross-section of the smearing element 125, perpendicular to the direction of a slide plate 124 is shown, whereas FIG. 13C illustrates a cross-section along the extension of said plate 124. The width of the resilient smearing element 125 substantially correspond to the side length of a carrier and it forms a small outlet for linearly sweeping over the carrier surface, when moving the slide plate 124, such that each carrier is coated by a thin layer of cells. Thereafter the above described washing steps are performed.

Figure 14:
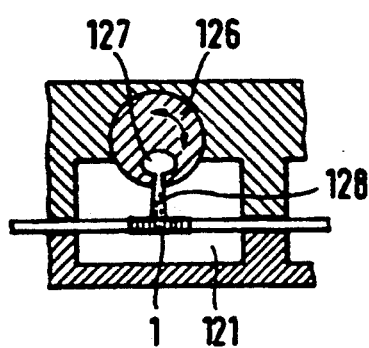
FIG. 14 shows in section another embodiment of a blood supply element for use with the separation unit of FIG. 12.

In FIG. 14 another embodiment of the smearing element is shown in a cross-section, perpendicular to a channel 121. A swiveling bar 126 extending along each channel 121 a blood conduit 127 is formed, which at each carrier 1, is provided with an outlet, having a distributing brush 128. When supplying blood to the carrier, the swiveling bar 126 is swivelled several times, thereby brushing the cells onto the carrier 1.

Figure 15:
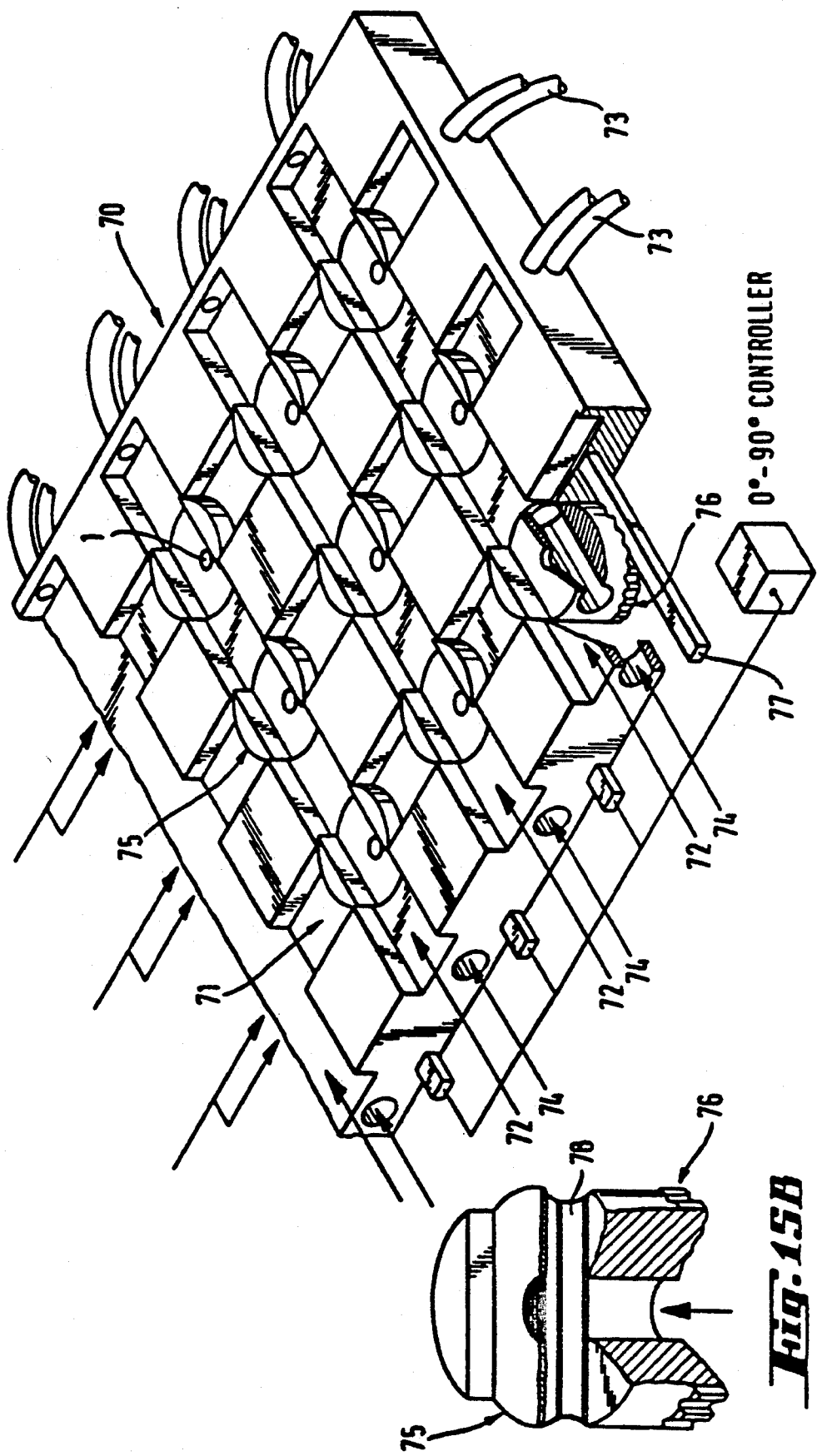
FIGS. 15A and 15B illustrate an embodiment of a multi-carrier system for clinical use, wherein the separation and measuring steps are combined.

While in the above embodiment blood supply and "rough" separation is performed by means of a special separation unit whereafter the holders 40, 50 and 114, respectively, have to be placed on a flow chamber for optical scanning, in some cases it may be desirable to eliminate this step. In a further embodiment of the invention which is shown in FIGS. 15A and 15B the cell separation and the optical scanning operation are therefore combined in one apparatus.

A supporting system 70 is provided with surface channels 71, 72 extending transversely to each other and inner conduits 73, 74 also extending transversely to each other. At every junction a carrier 1 is arranged on a rotatable holder 75, a section of which is shown in FIG. 15B. At its base a pinion 76 is formed which cooperates with a respective rack 77, extending through the supporting member 70. One rack 77 drives all the holders 75 of the respective column. Linear movement of this rack 77 causes rotation of the holders 75. The direction of introducing blood for rough separation, i.e., for separating the group of lymphocytes from the other group of blood cells, is perpendicular to the plane in which the cell carrier is scanned under the microscope. Thus, after separation of the lymphocytes from other blood cells the holders 75 are rotated 90° for the scanning operation.

In order to make possible the technique of "transmitted light" (measuring light exiting the bottom end of a hole) in the above embodiment, the portion of the channel which crosses the holder 75 under the cell carriers is a pipe of glass 78 which is divided lengthwise. This pipe is arranged so that its open side is directed towards the carrier (see FIG. 15B). In this way horizontal liquid flow through the holder is made possible, while at the same time light is transmitted in a vertical direction. The subpressure in this system is caused by making the inner conduits 73, 74 closed and thinner, while the upper channels 71, 72 are wider and open. The same effect can be achieved by other techniques, such as increasing the flow rate in the inner conduits with respect to that of the upper channels.

The procedure can be summarized as follows: With the aid of a 0°–90° controller the position of the holders 75 is determined. In a first stage, when the "rough separation" is carried out, the channels 71 and conduits 73 are in operation. Upon completion of this stage, the holders 75 are rotated by 90°. Thus the channels 71 and conduits 73 are blocked or closed and the channels 72 and conduits 74 are opened.

In this embodiment a blood drip-head may be attached to the scanning head, e.g. microscope. Then in response to command signals from a controller, e.g. a computer, the separation and the optical scanning are performed automatically and without need for a trained operator. The operator need only place the syringes, as shown in FIG. 6 and to change the holders 75, after completion of the tests.

In FIG. 16 to which attention is directed, an overall system of cell separation, scanning and analysis (diagnosis) is shown. A flow chamber 81, as described above, is mounted on a table 82 which is displaceable in three axes X, Y, Z by respective computer controlled step motors 83, 84, 85. The optical system includes a microscope 86 with an optical analyzer 87, as described in FIG. 4. An excitation light source 88, e.g. a zirconium lamp, uses the same optical system in reverse direction. In a solution tank 89 all the solutions necessary for cell separation and testing are stored. By a solution control unit 90 the supply of the respective solution is controlled. In order to stabilize the fluorescein concentration in the cells, which may influence the absolute polarization values, an electro-optical mechanical feedback control is used, wherein the intensity of the fluorescence emission light is periodically measured and compared with a reference value. Any deviation of the measured value from the reference value may be used to cause a change in the concentration of FDA in the PBS solution. The analysis of the measured value may be carried out by any well known computer system. A precomputer interface 91 serves to transform the measured values into computer-readable information which is typically digital. In a computer 92 the necessary calculations and identification steps are performed and stored in a memory 93. A post computer controller 94 generates the control signals for the step motors and the solution control unit.

The operation of the above system may be summarized as follows: After the rough separation procedure, the flow chamber is fixed on the table 82. The microscope is adjusted. Henceforth the test proceeds automatically. A PBS+FDA solution is introduced through the channels and conduits. Part of it penetrates through the carriers from the upper channels to the lower conduits and part of it continues to flow through the upper channels, washing the cells from above. After a chosen pause, e.g. 20 minutes, the scan begins. The polarization of every single cell is measured at the desired wavelengths. There is no danger of over-exposure of the cell to the exciting light, e.g. 470 nm, because scanning is performed very rapidly.

The optical information—after conversion into an electric current pulse—is fed into the computer, evaluated and stored in the memory. Every single cell is identified in the memory according to its coordinates, i.e. address on the carrier. From this stage on, everything that can be learned about each single cell will be stored in the computer relating to its address.

The collection of data may be summarized as follows: The control values of cells of all patients whose carriers are aligned in one channel will first be determined. Then the scanning head will be transferred to the next channel (by lowering the table and moving it aside) and will be used in the determination of the control values of all the cells on the carriers aligned in the second channel. Simultaneously with the data collection from the second channel a stimulating solution will be introduced into the first channel. Upon termination of the data collection from the second channel the scanning head is transferred to the third channel and a second stimulating solution is introduced into the second channel etc.

After data collection from all the carriers the scanning head will be returned to its first position. Then the scanning operation is repeated on the stimulated cells. This time the data collection will be selective and only cells which meet the described optical criterion, i.e. those belonging to the particular subgroup, will be re-read. Therefore, the information which will be accumulated in the computer will be cell position, control values, values of polarization after stimulation with PHA, values of polarization after stimulation with CaBP, SCM-response ratio, (See L. Cercek et al, in Europ. J. Cancer, Vol. 17, pp. 167–171, 1981), polarization values after stimulation with specific tumor stimulators, and the like.

The distinction between the cell carriers of different patients may be made by magnetic or optical coding which can be fixed on the holders during the rough separation stage. A magnetic or optical reader can be attached to the optical scanning head which will read the patient's code and transfer it to the computer. All the information pertaining to each patient may be transferred to a predetermined place in the computer memory.

By this system the exact number of activated lymphocytes can be determined for every stimulating agent. To one familiar with the art, the present invention permits cancer diagnosis at a very early stage. Although the present invention has been described primarily in conjunction with cancer diagnosis it is obvious that the inventive method and system are not limited thereto. Generically they provide a method and means for rapidly conducting biological assays leading to new clinical diagnosis and treatment as well as to new applications in the field of biotechnology and bioengineering.

As mentioned above, the exact position of each activated cell on a carrier is determined and stored. Therefore it is possible to isolate a desired group or subgroup of cells on the carrier by selectively removing all other cells from the carrier, so that only the subgroup of cells remains thereon, or by releasing and removing only the cells of the subgroup from the carrier. To this end use may be made of the known fact that cells are not electrically neutral but possess electrical surface charges. This fact may be used in the above described embodiments for bonding or otherwise securing the cells to the carrier. The same effect may be used to selectively release or hold desired cells. This may be achieved by a modified embodiment of the cell carrier of FIG. 1A, which will now be explained in connection with FIG. 17. The outer shape of the carrier 100 is the same as shown in FIG. 1A. However, carrier 100 is provided with electrical conductors 101 extending between the holes 102 in grid-like configuration and being electrically isolated from each other. At the periphery of the carrier the conductors are connected in a known manner (IC-technique) to a computer controlled switching arrangement for selectively influencing the electrical potential of every conductor 101. For securing the cells to the carrier all conductors 101 may be held at the same potential opposite the cells' charge potential, resulting in electrical attraction of the cells. For releasing any cell, say the one in the hole marked A in FIG. 17, the neighboring conductors $V_{x2}$, $V_{x3}$, $V_{y1}$, $V_{y2}$ may be set to an appropriate potential to cause the ejection of the cell in hole A from the carrier while the potentials at other holes is adjusted to prevent the cells captured in those holes from being ejected.

The cell carrier 100 may be produced by a multilayer technique, known from IC-production. In case an ionic solution, such as PBS, is used, measures should be taken to avoid undesired influences of possible surface charges on the holder. For this purpose it may be isolatedly coated and provided with conducting elements ending in the channel. This would cause ions to be attracted and neutralized, thus preventing the formation of an ion cover over the holder surface which may affect the potential of the carrier. Another possibility is to use non-ionic, organic solutions such as lipids for flowing the carrier in this stage of the procedure.

The separation of particular cells in accordance with the invention from all other cells is uniquely applicable in the field of clinical treatment in the production of clones. Clones may be produced from particular cells which were selected from other cells in accordance with the present invention based on any chosen property. For example, it is well known that the body of a person, afflicted with certain diseases, e.g. skin cancer, produces identifiable cells to combat or kill the disease. However, to be successful, a large number of such cells, hereafter referred to as killer cells, may have to be present in the body. With the present invention, blood, lymph nodes and different body tissue, containing some killer cells, may be used as the source of such cells. After separating them, as heretofore described, from all other cells, the killer cells may be multiplied by appropriate cell growing techniques, and then introduced into the patient, from which the original cells were received to fight the disease. In such a case, no cell rejection is expected since the cells originated from the patient's body. Thus, the present invention can be used to provide a person's body with enough cells to fight its own affliction.

It should be pointed out that whereas heretofore the separation between cells of interest on the carrier and other cells can be accomplished by expelling or removing either the cells of interest from the carrier so that only the other cells remain on it, or by removing the cells which are not of interest and leaving only the selected cells on the carrier, if desired one can produce such separation by destroying, i.e., killing, the cells which are not of interest while they are in apertures of the carriers so that the only live cells remaining on the carrier are the cells of interest. The killing of cells in the apertures, i.e., in-situ, may be achieved by directing a laser beam to each cell at its known address as well as by similar or analogous means. A killed cell, i.e., a dead cell, even though on the carrier can thus be regarded as being separated or removed therefrom since for all practical purposes, once killed it is disregarded. as used herein the term "expelling" of a cell is intended to include removing a cell from the carrier or killing it in-situ.

As to multiplying cells of interest it should thus be apparent that it can be done after: a) the cells to be multiplied were removed from the carrier bearing live cells which are not of interest on it; b) removing the cells which are not of interest from the carrier and thereafter multiplying the cells of interest for growth purposes; and c) killing the cells which are not of interest when they are still in the apertures and multiplying the cells of interest in-situ, i.e., while they are in their apertures of the carrier.

While the principles of the invention have been described in connection with specific systems, applications and methods, it is to be understood that this description is provided for explanatory purposes only and is not intended as a limitation of the scope of the invention.

Many new applications in biological research, clinical treatment and industrial production are opened by the present invention. It is expected, and has been established to a satisfactory extent, that there are optical parameters related to the cyclic phase of the cells. By this invention it is possible to differentiate a cell population according to the cells' age, their cycle stage and their inherent function, and to conduct respective examinations. A clinical application of the above resides in early detection of leukemia which is characterized by the presence of a high number of young cells of a certain type or types in the blood, and in the bone marrow.

As another clinical application immunoreactivity tests for organ transplantations may be performed. To this end a preparation of the transplant is used as stimulating agent in the invention.

A general and major feature and advantage of the invention is the fact that the time required for biological experiments and tests is substantially shortened since cell identification and testing is carried out in a substantially shorter time than in conventional biological methods wherein natural developments often have to be reproduced under artificial conditions, leading to uncertain results, necessitating extensive statistical evaluations. The invention reduces the influences of the surroundings allowing numerical analysis with a minimum of statistics. The time requirement to perform measurements with the present invention is very short in absolute terms as compared to the prior art, thereby reducing the effect of changes in the environmental conditions of the surroundings, such as temperature, humidity, etc.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. Apparatus for holding living cells at identifiable locations comprising an apertured cell carrier having a configuration defining first and second outer surfaces, said carrier comprising an ordered array of holes including a plurality of different sub-groups therethrough, the positions on the carrier of the holes being identifiable and the holes being sized to have the ability to contain individual living cells having a generally spherical shape therewithin, one cell only per hole, in that the holes have (i) a first cross section at the first outer surface of the carrier of such dimensions that living cells can pass through the first cross section without suffering substantial damage, (ii) a second cross section at a level intermediate between said first and second outer surfaces and of such dimensions that said living cells cannot pass through the second cross section, and (iii) a height between the first outer surface and the level of the second cross section such that either such an entire living cell or substantially such an entire living cell is containable within the hole, and wherein said ordered array comprises a first sub-group of uniformly shaped holes and at least one other sub-group of uniformly shaped holes, wherein the cross sectional dimensions of said first sub-group are different from the cross sectional dimensions of said at least one other sub-group, whereby the holes in said first sub-group are adapted to accommodate individual living cells of a preselected first size therewithin, one cell only per hole, and the holes in said at least one other sub-group are adapted to accommodate individual living cells of at least one preselected other size therewithin, one cell only per hole, which cells are different from the cells of said preselected first size.

2. The apparatus for holding living cells at identifiable locations of claim 1 wherein said first and second outer surfaces each define a plane and said planes are parallel to each other 3. The apparatus for holding living cells at identifiable locations of claim 2 wherein the second cross section defines a plane and said plane is parallel with the planes defined by said first and second outer surfaces.

4. The apparatus for holding living cells at identifiable locations of claim 1 in combination with a holder for the carrier.

5. The apparatus for holding living cells at identifiable locations of claim 4 which includes alignment means on the carrier, the holder including complementary alignment means, whereby on alignment of the alignment means on the carrier with the complementary alignment means, the identification of individual addresses of holes in the carrier by a set of x and y coordinates is facilitated.

6. The apparatus for holding living cells at identifiable locations of claim 1, in combination with a holder for the carrier, wherein the carrier is formed integrally with said holder.

7. Apparatus for holding living cells at identifiable locations comprising an apertured cell carrier having a configuration defining first and second outer surfaces, said carrier comprising an ordered array of holes therethrough, the positions on the carrier of the holes being identifiable and the holes being sized to have the ability to contain individual living cells having a generally spherical shape therewithin, one cell only per hole, in that the holes have (i) a first cross section at the first outer surface of the carrier of such dimensions that living cells can pass through the first cross section without suffering substantial damage, (ii) a second cross section at a level intermediate between said first and second outer surfaces and of such dimensions that said living cells cannot pass through the second cross section, and (iii) a height between the first outer surface and the level of the second cross section such that either such an entire living cell or substantially such an entire living cell is containable within the hole;

said apparatus being in cooperative combination with means for producing force acting on cells when these are present in individual holes on the carrier, wherein said means for producing force comprises electromagnetic means arranged for the production of at least one field selected from electric and magnetic fields in a predetermined pattern with respect to the holes.

8. The apparatus for holding living cells at identifiable locations of claim 7 wherein the predetermined pattern is such that there is produced an electric field oriented perpendicular to the first outer surface of the carrier.

9. The apparatus for holding living cells at identifiable locations of claim 7 wherein the predetermined pattern is such that there is produced an electric field parallel to the first outer surface of the carrier in conjunction with a crossed magnetic field parallel to the first outer surface of the carrier.

10. The apparatus for holding living cells at identifiable locations of claim 9 wherein the electric field is a time varying electric field and the magnetic field is a constant magnetic field.

11. The apparatus for holding living cells at identifiable locations of claim 7 wherein the predetermined pattern is such that there is produced a time varying magnetic field oriented perpendicular to the first outer surface of the carrier.

12. Apparatus for holding living cells at identifiable locations comprising an apertured cell carrier having a configuration defining first and second outer surfaces, said carrier comprising an ordered array of holes therethrough, the positions on the carrier of the holes being identifiable and the holes being sized to have the ability to contain individual living cells having a generally spherical shape therewithin, one cell only per hole, in that the holes have (i) a first cross section at the first outer surface of the carrier of such dimensions that living cells can pass through the first cross section without suffering substantial damage, (ii) a second cross section at a level intermediate between said first and second outer surfaces and of such dimensions that said living cells cannot pass through the second cross section, and (iii) a height between the first outer surface and the level of the second cross section such that either such an entire living cell or substantially such an entire living cell is containable within the hole;

said apparatus including additionally electrical conductors embedded in the carrier in such manner that the said configuration is maintained, and said apparatus also being in cooperative combination with means for applying differentially variable potentials to different ones of said embedded conductors.

13. Apparatus for holding living cells at identifiable locations comprising an apertured cell carrier having a configuration defining first and second outer surfaces, said carrier comprising an ordered array of holes therethrough, the positions on the carrier of the holes being identifiable and the holes being sized to have the ability to contain individual living cells having a generally spherical shape therewithin, one cell only per hole, in that the holes have (i) a first cross section at the first outer surface of the carrier of such dimensions that living cells can pass through the first cross section without suffering substantial damage, (ii) a second cross section at a level intermediate between said first and second outer surfaces and of such dimensions that said living cells cannot pass through the second cross section, and (iii) a height between the first outer surface and the level of the second cross section such that either such an entire living cell or substantially such an entire living cell is containable within the hole, and the carrier containing at least one entire living cell or at least one substantially entire living cell, held within at least one individual hole therein, one cell only per hole;

and wherein said ordered array comprises at least one sub-group of uniformly shaped holes of such cross sectional dimensions that individual living cells of a particular identical size are held therewithin, one cell only per hole, and said at least one sub-group of uniformly shaped holes comprises a first sub-group of uniformly shaped holes and said carrier comprises additionally at least one other sub-group of uniformly shaped holes, wherein the cross sectional dimensions of said first sub-group are different from the cross sectional dimensions of said at least one other sub-group, whereby the holes in said first sub-group hold individual living cells of a preselected first size therewithin, one cell only per hole, and the holes in said at least one other sub-group hold individual living cells of at least one preselected other size therewithin, one cell only per hole, which cells are different from the cells of said preselected first size.

* * * * *

UNITED STATES PATENT AND TRADEMARK OFFICE
CERTIFICATE OF CORRECTION

PATENT NO. : 5,310,674

DATED : May 10, 1994

INVENTOR(S) : Arye Weinreb and Mordechai Deutsch

It is certified that error appears in the above-identified patent and that said Letters Patent is hereby corrected as shown below:

Column 2/line 59 "that" should read "in that"

Column 5/line 36 "microgram" should read "micrographs"

Column 7/line 47 "configuration" should read "configurations"

Column 7/line 52 "bottom" should read "bottoms"

Column 8/line 5 "most of not" should read "most if not"

Column 8/line 28 "bottom" should read "bottom sides"

Column 9/line 40 "Figs. 18≥20" should read "Figs. 18-20"

Column 13/line 51 "The makes" should read "This makes"

Column 14/line 13 "320X" should read "3200X"

Column 16/line 14 "cell membrane" should read "cell membranes"

Column 18/line 35 "narrow hand" should read "narrow band"

Column 29/line 10 "the carriers" should read "the carrier"

UNITED STATES PATENT AND TRADEMARK OFFICE
CERTIFICATE OF CORRECTION

PATENT NO. : 5,310,674
DATED : May 10, 1994
INVENTOR(S) : Arye Weinreb and Mordechai Deutsch It is certified that error appears in the above-indentified patent and that said Letters Patent is hereby corrected as shown below:

Column 29/line 17 "as used" should read "As used"

Signed and Sealed this

Twenty-seventh Day of December, 1994

Attest:

BRUCE LEHMAN

*Attesting Officer*     *Commissioner of Patents and Trademarks*